(12) United States Patent
Kim et al.

(10) Patent No.: US 8,362,012 B2
(45) Date of Patent: Jan. 29, 2013

(54) BENZOXAZINE BENZIMIDAZOLE DERIVATIVE, A PHARMACEUTICAL COMPOSITION COMPRISING THE SAME, AND A USE THEREOF

(75) Inventors: Ji Duck Kim, Yongin-si (KR); Hong-Chul Yoon, Incheon-si (KR); Seong Hee Cho, Seoul (KR); Inwoo Kim, Sungnam-si (KR); Min Jae Cho, Euijeongbu-si (KR); In Young Lee, Yongin-si (KR); Hyae Jung Hyun, Seoul (KR); Eunkyung Park, Suwon-si (KR)

(73) Assignee: Daewoong Pharmaceutical Co., Ltd., Sungnam-si (KR)

( * ) Notice: Subject to any disclaimer, the term of this patent is extended or adjusted under 35 U.S.C. 154(b) by 108 days.

(21) Appl. No.: 12/934,638

(22) PCT Filed: Apr. 16, 2009

(86) PCT No.: PCT/KR2009/001977
§ 371 (c)(1),
(2), (4) Date: Dec. 20, 2010

(87) PCT Pub. No.: WO2009/128661
PCT Pub. Date: Oct. 22, 2009

(65) Prior Publication Data
US 2011/0086849 A1    Apr. 14, 2011

(30) Foreign Application Priority Data

Apr. 18, 2008 (KR) .................. 10-2008-0036301

(51) Int. Cl.
C07D 413/14 (2006.01)
A61K 31/538 (2006.01)
(52) U.S. Cl. .................. 514/230.5; 544/105
(58) Field of Classification Search .................. 544/105; 514/230.5
See application file for complete search history.

(56) References Cited

U.S. PATENT DOCUMENTS
8,026,235 B1 *  9/2011 Kim et al. .................. 514/230.5
2006/0116368 A1  6/2006 Calvo et al.

FOREIGN PATENT DOCUMENTS
WO    2004/035549 A1    4/2004
WO    2006/080821 A1    8/2006
WO    2008/007900 A1    1/2008

OTHER PUBLICATIONS

Chalmers (TiPS vol. 17, pp. 166-172 Apr. 1996).*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Ognyanov et al., "Design of Potent, Orally Available Antagonists of the Transient Receptor Potential Vanilloid 1. Structure—Activity Relationships of 2-Piperazin-1-yl-1H-benzimidazoles," *J. Med. Chem.* 49:3719-3742, 2006.
Shao et al., "4-(2-Pyridyl)piperazine-1-benzimidazoles as potent TRPV1 antagonists," *Bioorganic & Medicinal Chemistry Letters* 15:719-723, 2005.

* cited by examiner

*Primary Examiner* — Kahsay T Habte
(74) *Attorney, Agent, or Firm* — Seed IP Law Group PLLC

(57) ABSTRACT

The present invention relates to a novel benzoxazine benzimidazole derivative of formula (1) as an antagonist against a vanilloid receptor-1, a pharmaceutical composition comprising the same as an active ingredient, and a use thereof. The benzoxazine benzimidazole derivative of the present invention may be useful for preventing or treating a disease associated with antagonistic activity of vanilloid receptor-1:

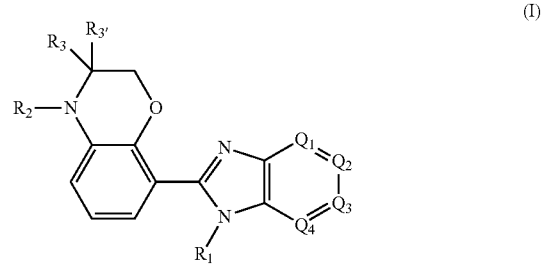

(I)

wherein, $R^1$, $R^2$, $R^3$, R3', $Q^1$, $Q^2$, $Q^3$ and $Q_4$ have same meanings as defined in the specification.

7 Claims, No Drawings

BENZOXAZINE BENZIMIDAZOLE DERIVATIVE, A PHARMACEUTICAL COMPOSITION COMPRISING THE SAME, AND A USE THEREOF

CROSS-REFERENCES TO RELATED APPLICATIONS

This application is a U.S. national stage application filed under 35 U.S.C. §371 of International Patent Application No. PCT/KR2009/001977 accorded an international filing date of Apr. 16, 2009, which application claims priority to Korean (KR) Patent Application No. 10-2008-0036301, filed Apr. 18, 2008, all which applications are incorporated herein by reference in their entirety.

FIELD OF THE INVENTION

The present invention relates to a novel benzoxazine benzimidazole derivative as an antagonist against a vanilloid receptor-1, a pharmaceutical composition comprising the same as an active ingredient, and a use thereof.

BACKGROUND OF THE INVENTION

A vanilloid receptor, a receptor for capsaicin (trans-8-methyl-N-vanillyl-6-nonenamide), has been cloned in 1997 and called vanilloid receptor subtype 1 (hereinafter referred to as "VR-1") by Caterina et al. (Caterina et al., Nature, 389, 816 (1997)). Located on small unmyelinated nerve fibers (C-fibers) and also on large myelinated nerve fibers (A-fibers), VR-I is an ion channel which plays an important role in sensitizing pain stimuli by introducing a strong influx of cations such as calcium and sodium ions into the nerve endings upon activation in response to external or internal stimuli. External stimuli capable of activating VR-I are reported to include heat and acids as well as vanilloid compounds (Tominaga et al., Neuron, 21, 531 (1998)). The internal stimuli to VR-1, on the other hand, are leukotriene metabolites such as 12-hydroperoxyeicosa tetraenoic acid (12-HPETE) (Hwang at al., PNAS, 97, 3655 (2000)), and arachidonic acid derivatives such as anandamide (Premkumar et al., Nature, 408, 985 (2000)).

On the basis of these physiological activities, VR-1 has attracted intensive attention as an integral controller playing a pivotal role in transferring various external stimuli into nerve cells. According to a report, VR-1 knock-out mice respond like normal mice to general stimuli, but showed greatly reduced pain response to heat or thermal hyperalgesia (Caterina et al., Science, 288, 306 (2000)).

VR-1 is expressed mainly in primary sensory neurons (Caterina et al., Nature, 389, 816 (1997)), which are responsible for controlling the functions of the skin, bone, and internal organs such as the bladder, the gastrointestinal tract, the lungs, and so on. In addition, VR-1 is also distributed in other neurons on the central nervous system, the kidney, the stomach, and T-cells (Nozawa et al., Neuroscience Letter, 2001, 309, 33; Yiangou et al., Lancet (North America Edition), 357, 1338 (2001); Birder et al., PNAS, 98, 13396 (2001)) and throughout the entire body, and plays important roles in cell division and cellular signal control.

Also, associated with the control mechanism of the activity of VR-1 are acute pain, chronic pain, neuropathic pain, post-operative pain, migraines, arthralgia, neuropathy, neuronal damages, diabetic neuropathy, neurological disorders, neuro-dermatitis, stroke, bladder hypersensitivity, irritable bowel syndrome, respiratory disorders such as asthma, chronic obstructive pulmonary disease, irritation to the skin, eye, and mucous membranes, itching, fever, reflux esophagitis, gastricduodenal ulcer, inflammatory intestinal diseases, and urge incontinence (Korean Laid-Open Publication No. 2004-0034804), obesity (Pharmacol. Rev., 38, 179 (1986)), and gluacoma (WO07/090134).

As compounds capable of modulating VR1 activity, agonists such as a capsaicin derivative (DA-5018) and resiniferatoxin are used as pain-relief drugs or are under clinical study (Szallasi, J. Med chem., 47, 2717 (2004)), while various VR-1 antagonists including capsazepine and iodoresiniferatoxin are under pre-clinical studies (WO02/008221, WO03/062209, WO04/055003, WO04/055004, WO04/002983, WO02/016317, WO04/035549, WO04/014871, WO03/099284, WO03/022809, WO02/090326, WO02/072536, WO03/068749, WO04/033435, WO02/076946, WO03/055484, WO03/014064, WO03/080578, WO03/097586, WO03/070247, WO03/029199, WO05/002551, WO05/007648, WO05/016890, WO05/047279, WO06/006740, WO06/006741, WO06/063178, WO06/124753, WO06/063178, WO07/067619, WO07/067,757, WO07/073,303, WO08/006481, WO08/007,211, and WO08/018,827).

SUMMARY OF THE INVENTION

Accordingly, it is a primary object of the present invention to provide a novel benzoxazine benzimidazole derivative, which is effective for inhibiting the activity of VR-1.

It is another object of the present invention to provide a pharmaceutical composition comprising said benzoxazine benzimidazole derivative as an active ingredient.

It is another object of the present invention to provide a method for preventing or treating a disease associated with antagonistic activity of vanilloid receptor-1 using said benzoxazine benzimidazole derivative.

In accordance with one aspect of the present invention, there is provided a compound of formula (I) or a pharmaceutically acceptable salt, hydrate, solvate or isomer thereof:

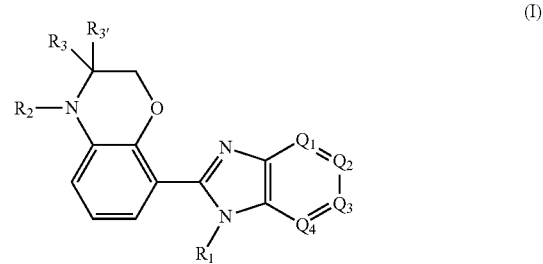

(I)

wherein, $R^1$ is hydrogen or $(CR^aR^{a'})_mR^b$, $R^a$ and $R^{a'}$ being each independently hydrogen; $C_1$-$C_8$ alkyl; $C_2$-$C_8$ alkenyl; halogen; nitro; hydroxy; cyano; azido; amino; phenyl; benzyl; $C_1$-$C_8$ alkoxy; $C_1$-$C_6$ alkylamino; or substituted $C_1$-$C_6$ alkyl, phenyl or benzyl having one or more $R^c$ groups; and $R^b$ being hydrogen; hydroxy; or substituted $C_1$-$C_6$ alkyl, phenyl or benzyl having one or more $R^c$ groups; in which $R^c$ is halogen; cyano; nitro; azido; phenyl; benzyl; $C(=O)R^d$; $C(=O)OR^d$; $C(=O)NR^dR^d$; $OR^d$; $OC(=O)R^e$; $OC(=O)OR^e$; $OC(=O)NR^dR^d$; $OC_1$-$C_6$alkylOR$^d$; $OC_1$-$C_6$alkylNR$^dR^d$; $SR_d$; $S(=O)R^e$; $S(=O)_2R^e$; $S(=O)_2NR^dR^d$; $CR^d=NR^d$; $NR^dR^d$; $NR^dC(=O)R^e$; $NR^dC(=O)OR^e$; $NR^dC(=O)NR^dR^d$; $NR^dC(=NR^d)NR^dR^d$; $NR^dS(=O)_2R^e$; $NR^dOR^d$; $NR^dC_1$-$C_6$alkylNR$^dR^d$; or $NR^dC_1$-$C_6$alkylOR$^d$; in which $R^d$ is hydrogen or $R^c$; $R^c$ being phenyl; benzyl; $C_1$-$C_6$ alkyl; phosphoryl; or substituted phenyl, benzyl or $C_1$-$C_6$ alkyl having one or more hydroxy, halogen, $C_1$-$C_4$ alkyl, $C_1$-$C_3$ haloalkyl, $C_1$-$C_4$ alkoxy, amino, $C_1$-$C_4$ alkylamino or di($C_1$-$C_4$ alkyl)amino groups; and m is 0, 1, or 2;

$R^2$ is hydrogen; $C_1$-$C_8$ alkyl; $C_2$-$C_6$ alkenyl; $C_1$-$C_8$ alkoxy; $C_1$-$C_6$ haloalkyl; $C_1$-$C_6$ haloalkoxy; halogen; nitro; hydroxy; $C_1$-$C_6$ hydroxyalkyl; cyano; amino; amido; substituted amino or amido having one or two $C_1$-$C_6$ alkyl, $C_2$-$C_6$ alkenyl, $C_1$-$C_8$ alkoxy, $C_1$-$C_6$ haloalkyl, $C_1$-$C_6$ haloalkoxy, halogen, nitro, hydroxy, or cyano groups; non-substituted or substituted cycloalkyl, pyridinyl, pyrimidinyl, pyrazolyl, pyrazinyl, phenyl, benzyl, imidazolyl, morpholinyl, benzodioxolyl, benzothiazolyl, benzimidazolyl, indolyl, pyrazolonyl, thiophenyl, furanyl, thiazolyl, isothiazolyl, oxazolyl, isoxazolyl, triazolyl, oxodiazolyl, thiadiazolyl, indazolyl, pyrrolidinyl, chromonyl, piperidinyl, morpholmethyl, dihydropyrazolyl or $(CH_2)pU$ having one, two or three sulfonamido groups, in which p is 0, 1, or 2; and U is morpholinyl,

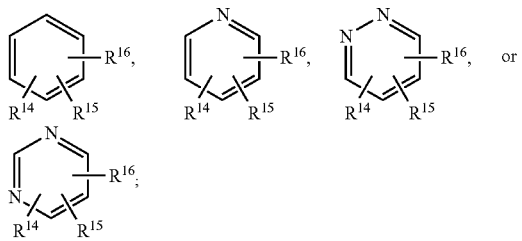

$R^{14}$, $R^{15}$ and $R^{16}$ are independently hydrogen; $C_1$-$C_8$ alkyl; cycloalkyl; $C_2$-$C_6$ alkenyl; $C_1$-$C_6$ alkoxy; $C_1$-$C_6$ haloalkyl; $C_1$-$C_6$ haloalkoxy; halogen; nitro; hydroxy; $C_1$-$C_6$ hydroxyalkyl; cyano; sulfanyl; sulfonyl; sulfinyl; sulfonamido; urea; carbamate; carbonate; carbonyl; amino; amido; carboxyl; carboxylester; substituted amino, amido, carboxyl or carboxylester having one or two $C_1$-$C_3$ alkyl groups; or any two of $R^{14}$, $R^{15}$ and $R^{16}$ being fused together to form a saturated or unsaturated heteromonocyclic or heterobicyclic ring;

$R^3$ and $R^{3'}$ are independently hydrogen; $C_1$-$C_{10}$ alkyl; $C_2$-$C_{10}$ alkenyl; $C_2$-$C_{10}$ alkynyl; $C_3$-$C_{10}$ cycloalkyl; $C_8$-$C_{14}$ bicycloalkyl; $C_3$-$C_{10}$ cycloalkenyl; $C_8$-$C_{14}$ bicycloalkenyl; $C_3$-$C_7$ heterocycloalkyl; $C_7$-$C_{10}$ heterobicycloalkyl; $C_1$-$C_6$ hydroxyalkyl; $C_1$-$C_8$ alkoxy; $C_1$-$C_6$ haloalkyl; $C_1$-$C_6$ haloalkoxy; halogen; nitro; hydroxy; cyano; azido; amino; substituted $C_1$-$C_6$ hydroxyalkyl, $C_1$-$C_{10}$ alkyl, $C_2$-$C_{10}$ alkenyl, $C_2$-$C_{10}$ alkynyl, $C_3$-$C_{10}$ cycloalkyl, $C_8$-$C_{14}$ bicycloalkyl, $C_3$-$C_{10}$ cycloalkenyl, $C_8$-$C_{14}$ bicycloalkenyl, $C_3$-$C_7$ heterocycloalkyl or $C_7$-$C_{10}$ heterobicycloalkyl having one or more $R^f$ substituents; phenyl; naphtyl; benzyl; $C_5$-$C_{10}$ heteroaryl; or substituted phenyl, naphtyl, benzyl or $C_5$-$C_{10}$ heteroaryl having one or more $R^f$ substituents; wherein $Q^1$ is N or $CR^4$;
$Q^2$ is N or $CR^5$;
$Q^3$ is N or $CR^6$;
$Q^4$ is N or $CR^7$;
$R^4$, $R^5$, $R^6$, and $R^7$ are independently hydrogen; $C_1$-$C_{10}$ alkyl; $C_2$-$C_{10}$ alkenyl; $C_2$-$C_{10}$ alkynyl; $C_3$-$C_{10}$ cycloalkyl; $C_8$-$C_{14}$ bicycloalkyl; $C_3$-$C_{10}$ cycloalkenyl; $C_8$-$C_{14}$ bicycloalkenyl; $C_3$-$C_7$ heterocycloalkyl; $C_7$-$C_{10}$ heterobicycloalkyl; $C_1$-$C_8$ alkoxy; $C_1$-$C_6$ haloalkyl; $C_1$-$C_6$ haloalkoxy; halogen; nitro; hydroxy; cyano; azido; amino; substituted $C_3$-$C_{10}$ alkyl, $C_2$-$C_{10}$ alkenyl, $C_2$-$C_{10}$ alkynyl, $C_3$-$C_{10}$ cycloalkyl, $C_8$-$C_{14}$ bicycloalkyl, $C_3$-$C_{10}$ cycloalkenyl, $C_8$-$C_{14}$ bicycloalkenyl, $C_3$-$C_7$ heterocycloalkyl or $C_7$-$C_{10}$ heterobicycloalkyl having one or more $R^h$ groups; phenyl; naphtyl; benzyl; $C_5$-$C_{10}$ heteroaryl; substituted phenyl, naphtyl, benzyl or $C_5$-$C_{10}$ heteroaryl having one or more $R^h$ substituents; $C(=O)R^i$; $C(=O)OR^i$; $C(=O)NR^iR^i$; $OR^i$; $OC(=O)R^j$; $OC(=O)OR^j$; $OC(=O)NR^iR^i$; $OC_1$-$C_6$alkylOR$^i$; $OC_1$-$C_6$alkylNR$^iR^i$; $SR^i$; $S(=O)R^i$; $S(=O)_2R^i$; $S(=O)_2NR^iR^i$; $CR^i=NR^i$; $NR^iR^i$; $NR^iC(=O)R^j$; $NR^iC(=O)OR^j$; $NR^iC(=O)NR^iR^i$; $NR^iC(=NR^i)NR^iR^i$; $NR^iS(=O)_2R^j$; $NR^iOR^i$; $NR^iC_1$-$C_6$alkylNR$^iR^i$; or $NR^iC_1$-$C_6$alkylOR$^i$; or any two of $R^4$, $R^5$, $R^6$ and $R^7$ are fused together to form a saturated, partially saturated or unsaturated 5-, 6- or 7-membered heteromonocyclic ring or a saturated, partially saturated, or unsaturated 6-, 7-, 8-, 9-, 10- or 11-membered heterobicyclic ring which is optionally mono-, di-, tri- or tetra-substituted with a nitrogen, an oxygen or a sulfur groups; in which $R^f$ and $R^h$ are each independently $C_1$-$C_6$ alkyl; $C_2$-$C_6$ alkenyl; $C_2$-$C_6$ alkynyl; $C_3$-$C_s$ cycloalkyl; $C_5$-$C_8$ cycloalkenyl; $C_3$-$C_5$ heterocycloalkyl; $C_1$-$C_6$ haloalkyl; $C_1$-$C_6$ haloalkoxy; halogen; azido; nitro; cyano; phenyl; benzyl; $C(=O)R^i$; $C(=O)OR^i$, $C(=O)NR^iR^i$; $OR^i$; $OC(=O)R^j$; $OC(=O)OR^j$; $OC(=O)NR^iR^i$; $OC_1$-$C_6$alkylOR$^i$; $OC_1$-$C_6$alkylNR$^iR^i$; $SR^i$; $S(=O)R^i$; $S(=O)_2R^i$; $S(=O)_2NR^iR^i$; $CR^i=NR^i$; $NR^iR^i$; $NR^iC(=O)R^j$; $NR^iC(=O)OR^j$; $NR^dC(=O)NR^iR^i$; $NR^iC(=NR^i)NR^iR^i$; $NR^iS(=O)_2R^j$; $NR^iOR^i$; $NR^iC_1$-$C_6$alkylNR$^iR^i$; or $NR^iC_1$-$C_6$alkylOR$^i$; and $R^i$ is hydrogen or $R^j$; $R^j$ being phenyl; benzyl; $C_1$-$C_6$ alkyl; $C_2$-$C_6$ alkenyl; $C_2$-$C_6$ alkynyl; $C_3$-$C_8$ cycloalkyl; $C_5$-$C_8$ cycloalkenyl; $C_3$-$C_5$ heterocycloalkyl; phosphoryl; or substituted phenyl, benzyl or $C_1$-$C_6$ alkyl having one or more hydroxy, halogen, $C_1$-$C_4$ alkyl, $C_1$-$C_3$ haloalkyl, $C_1$-$C_4$ alkoxy, amino, $C_1$-$C_4$ alkylamino or di($C_1$-$C_4$ alkyl)amino groups.

In accordance with another aspect of the present invention, there is provided a pharmaceutical composition comprising the compound of formula (1), or the pharmaceutically acceptable salt, hydrate, solvate, or isomer thereof as an active ingredient for the prevention and treatment of a disease associated with antagonistic activity of the vanilloid receptor.

In accordance with a further aspect of the present invention, there is provided a method for preventing or treating a disease associated with antagonistic activity of vanilloid receptor in a mammal, which comprises administering the compound of formula (1), or the pharmaceutically acceptable salt, hydrate, solvate, or isomer thereof to the mammal.

DETAILED DESCRIPTION OF THE INVENTION

Preferably, the compound of formula (1) according to the present invention may be a compound, wherein $R^1$ is hydrogen;
$R^2$ is $(CH_2)pU$, in which p is 0, 1, or 2, and U is morpholinyl or

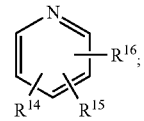

$R^{14}$, $R^{15}$ and $R^{16}$ are each independently hydrogen, $C_1$-$C_2$ alkyl, $C_2$-$C_3$ alkenyl, $C_1$-$C_2$ alkoxy, $C_1$-$C_2$ haloalkyl, $C_1$-$C_2$ haloalkoxy, halogen, hydroxy, or $C_1$-$C_6$ hydroxyalkyl;

$R^3$ and $R^{3'}$ are each independently hydrogen, $C_1$-$C_3$ hydroxyalkyl, or $C_1$-$C_3$ alkoxy; and $Q^1$ is $CR^4$, $Q^2$ is $CR^5$, $Q^3$ is $CR^6$, and $Q^4$ is $CR^7$, $R^4$, $R^5$, $R^6$, and $R^7$ are each independently hydrogen, $C_1$-$C_4$ alkyl, $C_1$-$C_2$ alkoxy, $C_1$-$C_2$ haloalkyl, $C_1$-$C_2$ haloalkoxy, halogen, hydroxy, or cyano.

More preferably, the compound of formula (1) according to the present invention may be a compound, wherein
$R^1$ is hydrogen;
$R^2$ is $(CH_2)pU$, in which p is 0, and U is

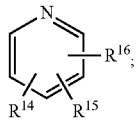

$R^{14}$, $R^{15}$ and $R^{16}$ are each independently hydrogen, $C_1$-$C_2$ alkyl, $C_2$-$C_3$ alkenyl; $C_1$-$C_2$ alkoxy; or halogen;
$R^3$ and $R^{3'}$ are each independently hydrogen, $C_1$-$C_2$ hydroxyalkyl, or $C_1$-$C_2$ alkoxy; and
$Q^1$ is $CR^4$, $Q^2$ is $CR^5$, $Q^3$ is $CR^6$, $Q^4$ is $CR^7$, $R^4$, $R^5$, $R^6$, and $R^7$ are each independently hydrogen, $C_1$-$C_4$ alkyl, $C_1$-$C_2$ alkoxy, $C_1$-$C_2$ haloalkyl, $C_1$-$C_2$ haloalkoxy, halogen, hydroxy, or cyano.

Preferred compounds useful in the present invention are selected from the group consisting of:
1) 8-(5-tert-butyl-1H-benzo[d]imidazol-2-yl)-3,4-dihydro-2H-benzo[b][1,4]oxazine,
2) 8-(6-(trifluoromethyl)-1H-benzo[d]imidazol-2-yl)-3,4-dihydro-2H-benzo[b][1,4]oxazine,
3) 8-(6-bromo-1H-benzo[d]imidazol-2-yl)-3,4-dihydro-2H-benzo[b][1,4]oxazine,
4) 8-(6-chloro-1H-benzo[d]imidazol-2-yl)-3,4-dihydro-2H-benzo[b][1,4]oxazine,
5) 8-(5,6-dichloro-1H-benzo[d]imidazol-2-yl)-3,4-dihydro-2H-benzo[b][1,4]oxazine,
6) 8-(6-tert-butyl-1H-benzimidazol-2-yl)-4-(3-chloro-pyridin-2-yl)-3,4-dihydro-2H-benzo[1,4]oxazine,
7) 8-(6-tert-butyl-1H-benzimidazol-2-yl)-4-(3-trifluoromethyl-pyridin-2-yl)-3,4-dihydro-2H-benzo[1,4]oxazine,
8) 8-(6-tert-butyl-1H-benzimidazol-2-yl)-4-(5-trifluoromethyl-pyridin-2-yl)-3,4-dihydro-2H-benzo[1,4]oxazine,
9) 8-(6-tert-butyl-1H-benzimidazol-2-yl)-4-(3-chloro-5-trifluoromethyl-pyridin-2-yl)-3,4-dihydro-2H-benzo[1,4]oxazine,
10) 8-(5-tert-butyl-1H-benzimidazol-2-yl)-4-(5-methyl-pyridin-2-yl)-3,4-dihydro-2H-benzo[1,4]oxazine,
11) 8-(5-tert-butyl-1H-benzimidazol-2-yl)-4-(3,5-dichloro-pyridin-2-yl)-3,4-dihydro-2H-benzo[1,4]oxazine,
12) 8-(5-tert-butyl-1H-benzimidazol-2-yl)-4-pyridin-2-yl-3,4-dihydro-2H-benzo[1,4]oxazine,
13) 4-(5-bromo-pyridin-2-yl)-8-(5-tert-butyl-1H-benzimidazol-2-yl)-3,4-dihydro-2H-benzo[1,4]oxazine,
14) 8-(5-tert-butyl-1H-benzimidazol-2-yl)-4-(5-chloro-pyridin-2-yl)-3,4-dihydro-2H-benzo[1,4]oxazine,
15) 6-[8-(5-tert-butyl-1H-benzimidazol-2-yl)-2,3-dihydro-benzo[1,4]oxazin-4-yl]-pyridin-3-yl-methanol,
16) 4-(3-chloro-pyridin-2-yl)-8-(6-trifluoromethyl-1H-benzimidazol-2-yl)-3,4-dihydro-2H-benzo[1,4]oxazine,
17) 8-(6-trifluoromethyl-1H-benzimidazol-2-yl)-4-(3-trifluoromethyl-pyridin-2-yl)-3,4-dihydro-2H-benzo[1,4]oxazine,
18) 4-(3,5-dichloro-pyridin-2-yl)-8-(6-trifluoromethyl-1H-benzimidazol-2-yl)-3,4-dihydro-2H-benzo[1,4]oxazine,
19) 4-(5-bromo-pyridin-2-yl)-8-(6-trifluoromethyl-1H-benzimidazol-2-yl)-3,4-dihydro-2H-benzo[1,4]oxazine,
20) 4-(5-chloro-pyridin-2-yl)-8-(6-trifluoromethyl-1H-benzimidazol-2-yl)-3,4-dihydro-2H-benzo[1,4]oxazine,
21) 8-(6-bromo-1H-benzimidazol-2-yl)-4-(3-chloro-pyridin-2-yl)-3,4-dihydro-2H-benzo[1,4]oxazine,
22) 8-(6-chloro-1H-benzimidazol-2-yl)-4-(3-chloro-pyridin-2-yl)-3,4-dihydro-2H-benzo[1,4]oxazine,
23) 8-(5,6-dichloro-1H-benzimidazol-2-yl)-4-(2-morpholine-4-yl-ethyl)-3,4-dihydro-2H-benzo[1,4]oxazine,
24) 8-(5,6-dichloro-1H-benzimidazol-2-yl)-4-pyridin-3-yl-methyl-3,4-dihydro-2H-benzo[1,4]oxazine,
25) 4-(5-methyl-pyridin-2-yl)-8-(6-trifluoromethyl-1H-benzimidazol-2-yl)-3,4-dihydro-2H-benzo[1,4]oxazine,
26) 8-(6-bromo-1H-benzimidazol-2-yl)-4-(5-methyl-pyridin-2-yl)-3,4-dihydro-2H-benzo[1,4]oxazine,
27) 8-(5-chloro-1H-benzimidazol-2-yl)-4-(5-methyl-pyridin-2-yl)-3,4-dihydro-2H-benzo[1,4]oxazine,
28) 8-(5,6-dichloro-1H-benzimidazol-2-yl)-4-(5-methyl-pyridin-2-yl)-3,4-dihydro-2H-benzo[1,4]oxazine,
29) 8-(4-chloro-6-trifluoromethyl-1H-benzimidazol-2-yl)-4-(5-methyl-pyridin-2-yl)-3,4-dihydro-2H-benzo[1,4]oxazine,
30) 8-(4,6-bis-trifluoromethyl-1H-benzimidazol-2-yl)-4-(5-methyl-pyridin-2-yl)-3,4-dihydro-2H-benzo[1,4]oxazine,
31) 8-(4-bromo-6-trifluoromethyl-1H-benzimidazol-2-yl)-4-(5-methyl-pyridin-2-yl)-3,4-dihydro-2H-benzo[1,4]oxazine,
32) 8-(4,6-dibromo-1H-benzimidazol-2-yl)-4-(5-methyl-pyridin-2-yl)-3,4-dihydro-2H-benzo[1,4]oxazine,
33) 8-(6-bromo-4-fluoro-1H-benzimidazol-2-yl)-4-(5-methyl-pyridin-2-yl)-3,4-dihydro-2H-benzo[1,4]oxazine,
34) [(S)-8-(6-tert-butyl-1H-benzimidazol-2-yl)-4-(5-methyl-pyridin-2-yl)-3,4-dihydro-2H-benzo[1,4]oxazin-3-yl]-methanol,
35) [(S)-4-(5-methyl-pyridin-2-yl)-8-(6-trifluoromethyl-1H-benzimidazol-2-yl)-3,4-dihydro-2H-benzo[1,4]oxazin-3-yl]-methanol,
36) [(S)-8-(6-bromo-1H-benzimidazol-2-yl)-4-(5-methyl-pyridin-2-yl)-3,4-dihydro-2H-benzo[1,4]oxazin-3-yl]-methanol,
37) [(S)-8-(6-chloro-1H-benzimidazol-2-yl)-4-(5-methyl-pyridin-2-yl)-3,4-dihydro-2H-benzo[1,4]oxazin-3-yl]-methanol,
38) [(S)-8-(5,6-dichloro-1H-benzimidazol-2-yl)-4-(5-methyl-pyridin-2-yl)-3,4-dihydro-2H-benzo[1,4]oxazin-3-yl]-methanol,
39) [(S)-8-(4-chloro-6-trifluoromethyl-1H-benzimidazol-2-yl)-4-(5-methyl-pyridin-2-yl)-3,4-dihydro-2H-benzo[1,4]oxazin-3-yl]-methanol,
40) [(S)-8-(4,6-bis-trifluoromethyl-1H-benzimidazol-2-yl)-4-(5-methyl-pyridin-2-yl)-3,4-dihydro-2H-benzo[1,4]oxazin-3-yl]-methanol,
41) [(S)-8-(4-bromo-6-trifluoromethyl-1H-benzimidazol-2-yl)-4-(5-methyl-pyridin-2-yl)-3,4-dihydro-2H-benzo[1,4]oxazin-3-yl]-methanol,
42) [(S)-8-(4,6-dibromo-1H-benzimidazol-2-yl)-4-(5-methyl-pyridin-2-yl)-3,4-dihydro-2H-benzo[1,4]oxazin-3-yl]-methanol,
43) [(S)-8-(6-bromo-4-fluoro-1H-benzimidazol-2-yl)-4-(5-methyl-pyridin-2-yl)-3,4-dihydro-2H-benzo[1,4]oxazin-3-yl]-methanol,
44) [(S)-8-(5,6-difluoro-1H-benzimidazol-2-yl)-4-(5-methyl-pyridin-2-yl)-3,4-dihydro-2H-benzo[1,4]oxazin-3-yl]-methanol,
45) [(S)-8-(6-chloro-5-fluoro-1H-benzimidazol-2-yl)-4-(5-methyl-pyridin-2-yl)-3,4-dihydro-2H-benzo[1,4]oxazin-3-yl]-methanol, 46) [(S)-8-(6-bromo-4-methyl-1H-benzimidazol-2-yl)-4-(5-methyl-pyridin-2-yl)-3,4-dihydro-2H-benzo[1,4]oxazin-3-yl]-methanol,
47) [(S)-4-(5-methyl-pyridin-2-yl)-8-(6-trifluoromethoxy-1H-benzimidazol-2-yl)-3,4-dihydro-2H-benzo[1,4]oxazin-3-yl]-methanol,
48) [(S)-8-(6-methoxy-1H-benzimidazol-2-yl)-4-(5-methyl-pyridin-2-yl)-3,4-dihydro-2H-benzo[1,4]oxazin-3-yl]-methanol,
49) [(S)-8-(6-fluoro-1H-benzimidazol-2-yl)-4-(5-methyl-pyridin-2-yl)-3,4-dihydro-2H-benzo[1,4]oxazin-3-yl]-methanol,
50) [(S)-8-(4-methyl-1H-benzimidazol-2-yl)-4-(5-methyl-pyridine-2-yl)-3,4-dihydro-2H-benzo[1,4]oxazin-3-yl]-methanol,
51) [(S)-8-(5-methyl-1H-benzimidazol-2-yl)-4-(5-methyl-pyridin-2-yl)-3,4-dihydro-2H-benzo[1,4]oxazin-3-yl]-methanol,
52) [(S)-8-(4,5-dimethyl-1H-benzimidazol-2-yl)-4-(5-methyl-pyridin-2-yl)-3,4-dihydro-2H-benzo[1,4]oxazin-3-yl]-methanol,
53) [(S)-8-(1H-benzimidazol-2-yl)-4-(5-methyl-pyridin-2-yl)-3,4-dihydro-2H-benzo[1,4]oxazin-3-yl]-methanol,
54) [(S)-8-(4-bromo-6-trifluoromethoxy-1H-benzimidazol-2-yl)-4-(5-methyl-pyridine-2-yl)-3,4-dihydro-2H-benzo[1,4]oxazin-3-yl]-methanol,
55) [(S)-8-(4,6-difluoro-1H-benzo[d]imidazol-2-yl)-4-(5-methyl-pyridin-2-yl)-3,4-dihydro-2H-benzo[b][1,4]oxazin-3-yl]-methanol,
56) (S)-2-(3-(hydroxymethyl)-4-(5-methyl-pyridin-2-yl)-3,4-dihydro-2H-benzo[b][1,4]oxazin-8-yl)-1H-benzo[d]imidazol-6-carbonitrile,
57) [(S)-8-(6-tert-butyl-1H-benzimidazol-2-yl)-4-(5-vinyl-pyridin-2-yl)-3,4-dihydro-2H-benzo[1,4]oxazin-3-yl]-methanol,
58) [(S)-8-(6-trifluoromethyl-1H-benzimidazol-2-yl)-4-(5-vinyl-pyridin-2-yl)-3,4-dihydro-2H-benzo[1,4]oxazin-3-yl]-methanol,
59) [(S)-8-(6-chloro-1H-benzimidazol-2-yl)-4-(5-vinyl-pyridin-2-yl)-3,4-dihydro-2H-benzo[1,4]oxazin-3-yl]-methanol,
60) [(S)-8-(6-bromo-1H-benzimidazol-2-yl)-4-(5-vinyl-pyridin-2-yl)-3,4-dihydro-2H-benzo[1,4]oxazin-3-yl]-methanol,
61) [(S)-8-(6-fluoro-1H-benzimidazol-2-yl)-4-(5-vinyl-pyridin-2-yl)-3,4-dihydro-2H-benzo[1,4]oxazin-3-yl]-methanol,
62) [(S)-8-(6-bromo-4-fluoro-1H-benzimidazol-2-yl)-4-(5-vinyl-pyridin-2-yl)-3,4-dihydro-2H-benzo[1,4]oxazin-3-yl]-methanol,
63) [(S)-8-(4,6-difluoro-1H-benzimidazol-2-yl)-4-(5-vinyl-pyridin-2-yl)-3,4-dihydro-2H-benzo[1,4]oxazin-3-yl]-methanol,
64) [(S)-8-(4-bromo-6-trifluoromethyl-1H-benzimidazol-2-yl)-4-(5-vinyl-pyridin-2-yl)-3,4-dihydro-2H-benzo[1,4]oxazin-3-yl]-methanol,
65) [(S)-8-(4-chloro-6-trifluoromethyl-1H-benzimidazol-2-yl)-4-(5-vinyl-pyridin-2-yl)-3,4-dihydro-2H-benzo[1,4]oxazin-3-yl]-methanol,
66) [(S)-8-(6-bromo-4-methyl-1H-benzimidazol-2-yl)-4-(5-vinyl-pyridin-2-yl)-3,4-dihydro-2H-benzo[1,4]oxazin-3-yl]-methanol,
67) [(S)-8-(6-trifluoromethoxy-1H-benzimidazol-2-yl)-4-(5-vinyl-pyridin-2-yl)-3,4-dihydro-2H-benzo[1,4]oxazin-3-yl]-methanol,
68) [(S)-8-(5,6-dichloro-1H-benzimidazol-2-yl)-4-(5-vinyl-pyridin-2-yl)-3,4-dihydro-2H-benzo[1,4]oxazin-3-yl]-methanol,
69) [(S)-8-(5,6-difluoro-1H-benzimidazol-2-yl)-4-(5-vinyl-pyridin-2-yl)-3,4-dihydro-2H-benzo[1,4]oxazin-3-yl]-methanol,
70) [(S)-8-(6-chloro-5-fluoro-1H-benzimidazol-2-yl)-4-(5-vinyl-pyridin-2-yl)-3,4-dihydro-2H-benzo[1,4]oxazin-3-yl]-methanol,
71) ((S)-8-(4,6-bis(trifluoromethyl)-1H-benzo[d]imidazol-2-yl)-4-(5-vinyl-pyridin-2-yl)-3,4-dihydro-2H-benzo[b][1,4]oxazin-3-yl)-methanol,
72) (S)-(8-(6-methoxy-1H-benzo[d]imidazol-2-yl)-4-(5-vinyl-pyridin-2-yl)-3,4-dihydro-2H-benzo[b][1,4]oxazin-3-yl)methanol,
73) (S)-2-(3-(hydroxymethyl)-4-(5-vinyl-pyridin-2-yl)-3,4-dihydro-2H-benzo[b][1,4]oxazin-8-yl)-1H-benzo[d]imidazol-6-carbonitrile,
74) (S)-(8-(6-methyl-1H-benzo[d]imidazol-2-yl)-4-(5-vinyl-pyridin-2-yl)-3,4-dihydro-2H-benzo[b][1,4]oxazin-3-yl)methanol,
75) (S)-(8-(1H-benzo[d]imidazol-2-yl)-4-(5-vinyl-pyridin-2-yl)-3,4-dihydro-2H-benzo[b][1,4]oxazin-3-yl)methanol,
76) (S)-(8-(4-methyl-1H-benzo[d]imidazol-2-yl)-4-(5-vinyl-pyridin-2-yl)-3,4-dihydro-2H-benzo[b][1,4]oxazin-3-yl)methanol,
77) (S)-(8-(4,5-dimethyl-1H-benzo[d]imidazol-2-yl)-4-(5-vinyl-pyridin-2-yl)-3,4-dihydro-2H-benzo[b][1,4]oxazin-3-yl)methanol,
78) [(S)-8-(6-tert-butyl-1H-benzimidazol-2-yl)-4-(5-ethyl-pyridin-2-yl)-3,4-dihydro-2H-benzo[1,4]oxazin-3-yl]-methanol,
79) [(S)-4-(5-ethyl-pyridin-2-yl)-8-(6-trifluoromethyl-1H-benzimidazol-2-yl)-3,4-dihydro-2H-benzo[1,4]oxazin-3-yl]-methanol,
80) [(S)-8-(4-chloro-6-trifluoromethyl-1H-benzimidazol-2-yl)-4-(5-ethyl-pyridin-2-yl)-3,4-dihydro-2H-benzo[1,4]oxazin-3-yl]-methanol,
81) [(S)-8-(4-bromo-6-trifluoromethyl-1H-benzimidazol-2-yl)-4-(5-ethyl-pyridin-2-yl)-3,4-dihydro-2H-benzo[1,4]oxazin-3-yl]-methanol,
82) [(S)-4-(5-ethyl-pyridin-2-yl)-8-(6-trifluoromethoxy-1H-benzimidazol-2-yl)-3,4-dihydro-2H-benzo[1,4]oxazin-3-yl]-methanol,
83) [(S)-8-(5,6-difluoro-1H-benzimidazol-2-yl)-4-(5-ethyl-pyridin-2-yl)-3,4-dihydro-2H-benzo[1,4]oxazin-3-yl]-methanol,
84) [(S)-8-(6-chloro-5-fluoro-1H-benzimidazol-2-yl)-4-(5-ethyl-pyridin-2-yl)-3,4-dihydro-2H-benzo[1,4]oxazin-3-yl]-methanol,
85) [(S)-8-(6-bromo-4-fluoro-1H-benzimidazol-2-yl)-4-(5-ethyl-pyridin-2-yl)-3,4-dihydro-2H-benzo[1,4]oxazin-3-yl]-methanol,
86) [(S)-8-(4,6-difluoro-1H-benzimidazol-2-yl)-4-(5-ethyl-pyridin-2-yl)-3,4-dihydro-2H-benzo[1,4]oxazin-3-yl]-methanol,
87) 2-[(S)-4-(5-ethyl-pyridin-2-yl)-3-hydroxymethyl-3,4-dihydro-2H-benzo[1,4]oxazin-8-yl]-3H-benzimidazol-5-carbonitrile,
88) (S)-8-(6-tert-butyl-1H-benzimidazol-2-yl)-3-methoxymethyl-4-(5-methyl-pyridin-2-yl)-3,4-dihydro-2H-benzo[1,4]oxazine,
89) (S)-8-(6-bromo-1H-benzimidazol-2-yl)-3-methoxymethyl-4-(5-methyl-pyridin-2-yl)-3,4-dihydro-2H-benzo[1,4]oxazine, 90) (S)-3-methoxymethyl-4-(5-methyl-pyridin-2-yl)-8-(6-trifluoromethyl-1H-benzimidazol-2-yl)-3,4-dihydro-2H-benzo[1,4]oxazine,
91) (S)-3-methoxymethyl-4-(5-methyl-pyridin-2-yl)-8-(6-chloro-1H-benzimidazol-2-yl)-3,4-dihydro-2H-benzo[1,4]oxazine,
92) (S)-8-(4-chloro-6-trifluoromethyl-1H-benzimidazol-2-yl)-3-methoxymethyl-4-(5-methyl-pyridin-2-yl)-3,4-dihydro-2H-benzo[1,4]oxazine,
93) (S)-8-(4-bromo-6-trifluoromethyl-1H-benzimidazol-2-yl)-3-methoxymethyl-4-(5-methyl-pyridin-2-yl)-3,4-dihydro-2H-benzo[1,4]oxazine,
94) (S)-8-(6-bromo-4-fluoro-1H-benzimidazol-2-yl)-3-methoxymethyl-4-(5-methyl-pyridin-2-yl)-3,4-dihydro-2H-benzo[1,4]oxazine,
95) (S)-8-(5,6-dichloro-1H-benzimidazol-2-yl)-3-methoxymethyl-4-(5-methyl-pyridin-2-yl)-3,4-dihydro-2H-benzo[1,4]oxazine,
96) (S)-8-(4,6-bis-trifluoromethyl-1H-benzimidazol-2-yl)-3-methoxymethyl-4-(5-methyl-pyridin-2-yl)-3,4-dihydro-2H-benzo[1,4]oxazine,
97) (S)-8-(4,6-dibromo-1H-benzimidazol-2-yl)-3-methoxymethyl-4-(5-methyl-pyridin-2-yl)-3,4-dihydro-2H-benzo[1,4]oxazine,
98) (S)-8-(6-fluoro-1H-benzimidazol-2-yl)-3-methoxymethyl-4-(5-methyl-pyridin-2-yl)-3,4-dihydro-2H-benzo[1,4]oxazine,
99) (S)-3-methoxymethyl-4-(5-methyl-pyridin-2-yl)-8-(6-trifluoromethoxy-1H-benzimidazol-2-yl)-3,4-dihydro-2H-benzo[1,4]oxazine,
100) (S)-8-(6,7-dimethyl-1H-benzimidazol-2-yl)-3-methoxymethyl-4-(5-methyl-pyridin-2-yl)-3,4-dihydro-2H-benzo[1,4]oxazine,
101) 2-[(S)-3-methoxymethyl-4-(5-methyl-pyridin-2-yl)-3,4-dihydro-2H-benzo[1,4]oxazin-8-yl]-3H-benzimidazol-5-carbonitrile,
102) (S)-8-(5,6-difluoro-1H-benzimidazol-2-yl)-3-methoxymethyl-4-(5-methyl-pyridin-2-yl)-3,4-dihydro-2H-benzo[1,4]oxazine,
103) (S)-8-(5-chloro-6-fluoro-1H-benzimidazol-2-yl)-3-methoxymethyl-4-(5-methyl-pyridin-2-yl)-3,4-dihydro-2H-benzo[1,4]oxazine,
104) (S)-8-(6-bromo-4-methyl-1H-benzimidazol-2-yl)-3-methoxymethyl-4-(5-methyl-pyridin-2-yl)-3,4-dihydro-2H-benzo[1,4]oxazine,
105) (S)-8-(4-bromo-6-trifluoromethoxy-1H-benzimidazol-2-yl)-3-methoxymethyl-4-(5-methyl-pyridin-2-yl)-3,4-dihydro-2H-benzo[1,4]oxazine,
106) (S)-8-(6-methoxy-1H-benzo[d]imidazol-2-yl)-3-(methoxymethyl)-4-(5-methyl-pyridin-2-yl)-3,4-dihydro-2H-benzo[b][1,4]oxazine,
107) (S)-8-(4,6-difluoro-1H-benzo[d]imidazol-2-yl)-3-(methoxymethyl)-4-(5-methyl-pyridin-2-yl)-3,4-dihydro-2H-benzo[b][1,4]oxazine,
108) (S)-3-(methoxymethyl)-8-(4-methyl-1H-benzo[d]imidazol-2-yl)-4-(5-methyl-pyridin-2-yl)-3,4-dihydro-2H-benzo[b][1,4]oxazine,
109) (S)-3-(methoxymethyl)-8-(5-methyl-1H-benzo[d]imidazol-2-yl)-4-(5-methyl-pyridin-2-yl)-3,4-dihydro-2H-benzo[b][1,4]oxazine, and
110) (S)-8-(1H-benzo[d]imidazol-2-yl)-3-(methoxymethyl)-4-(5-methyl-pyridin-2-yl)-3,4-dihydro-2H-benzo[b][1,4]oxazine, More preferred compounds useful in the present invention are selected from the group consisting of:

[(S)-8-(6-bromo-1H-benzimidazol-2-yl)-4-(5-methyl-pyridin-2-yl)-3,4-dihydro-2H-benzo[1,4]oxazin-3-yl]-methanol;
[(S)-8-(4-bromo-6-trifluoromethyl-1H-benzimidazol-2-yl)-4-(5-methyl-pyridin-2-yl)-3,4-dihydro-2H-benzo[1,4]oxazin-3-yl]-methanol;
[(S)-8-(6-bromo-4-fluoro-1H-benzimidazol-2-yl)-4-(5-methyl-pyridin-2-yl)-3,4-dihydro-2H-benzo[1,4]oxazin-3-yl]-methanol;
(S)-8-(4-bromo-6-trifluoromethyl-1H-benzimidazol-2-yl)-3-methoxymethyl-4-(5-methyl-pyridin-2-yl)-3,4-dihydro-2H-benzo[1,4]oxazine;
[(S)-8-(5,6-difluoro-1H-benzimidazol-2-yl)-4-(5-methyl-pyridin-2-yl)-3,4-dihydro-2H-benzo[1,4]oxazin-3-yl]-methanol; and
[(S)-8-(6-chloro-5-fluoro-1H-benzimidazol-2-yl)-4-(5-methyl-pyridin-2-yl)-3,4-dihydro-2H-benzo[1,4]oxazin-3-yl]-methanol.

The following synthetic schemes 1 to 4 are merely illustrative of the methods by which the compounds of formula (1) of the invention may be prepared and are not intended to limit the scope of the invention.

Particularly, a compound of formula (1a) may be prepared according to the method shown in Reaction Scheme 1. Hereinafter, the steps of the inventive method are described in detail as follows.

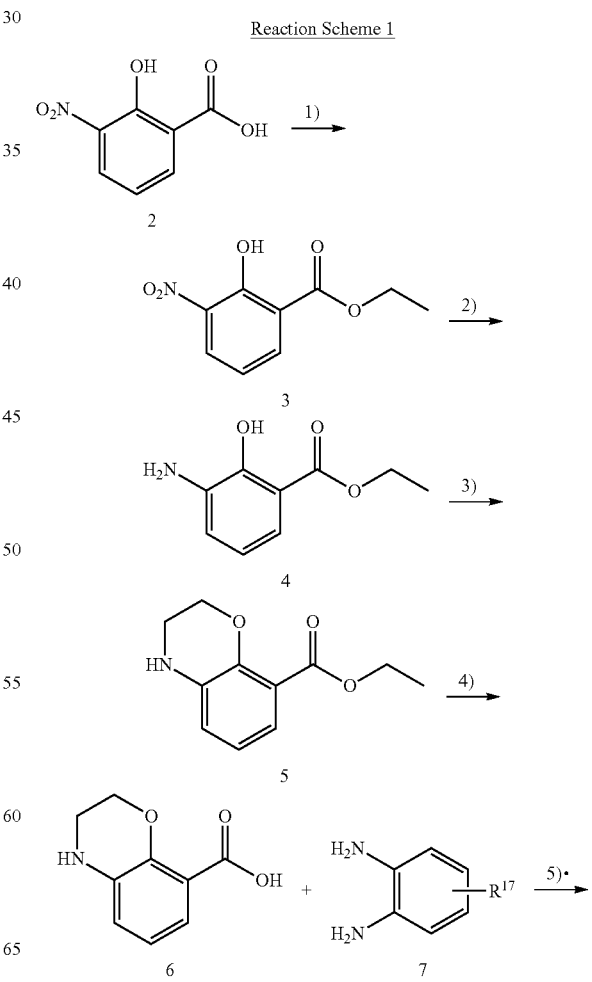

Reaction Scheme 1

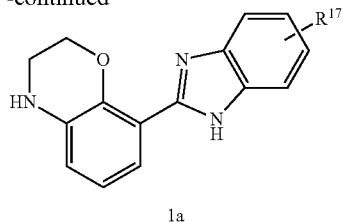

1a

In Reaction Scheme 1, $R^{17}$ is one or two substituents selected from halogen, $C_1$-$C_6$ alkyl, $C_1$-$C_6$ alkyl, $C_1$-$C_6$ alkoxy, $C_1$-$C_6$haloalkyloxy, $C_1$-$C_6$ haloalkyl and cyano, and $R^{18}$ is one or two substituents selected from hydrogen, halogen, $C_1$-$C_6$ alkyl, $C_1$-$C_6$ alkyl, $C_1$-$C_6$ alkoxy, $C_1$-$C_6$ hydroxyalkyl and $C_1$-$C_6$ haloalkyl.

As shown in Reaction Scheme 1, in step 1), the compound of formula (3) may be prepared by reacting the compound of formula (2) in an organic solvent in the presence of a hydrochloric acid. Examples of the organic solvent used in the step 1 include methanol, ethanol, etc. The above reaction may be conducted for 16 to 24 hours under reflux with heat.

In step 2), the compound of formula (4) may be prepared by reducing the compound of formula (3) in an organic solvent in the presence of a Pd/C catalyst in a hydrogen reactor. Examples of the organic solvent used in the step 2) include methanol, ethanol, etc. The Pd/C catalyst may be employed in an amount ranging from 5 to 10% by weight, based on the total weight of the compound of formula (3). The above reaction may be conducted for 2 to 5 hours at room temperature.

In step 3), the compound of formula (5) may be prepared by reacting the compound of formula (4) with dibromoethane under a base such as $K_2CO_3$. The dibromoethane may be employed in an amount ranging from 1.1 to 1.2 moles per 1 mole of the compound of formula (4). The above reaction may be conducted for 2 to 3 hours under reflux with heat.

In step 4), the compound of formula (6) may be prepared by reacting the compound of formula (5) with lithium hydroxide monohydrate. Lithium hydroxide monohydrate may be employed in an amount ranging from 2 to 3 moles per 1 mole of the compound of formula (5). The above reaction may be conducted for 6 to 8 hours at room temperature.

In step 5), the compound of formula (1a) may be prepared by condensating the compound of formula (6) with the compound of formula (7) and O-(7-azabenzotriazol-1-yl)-N,N,N',N'-tetramethyluronium hexafluorophosphate in a solvent under a base to obtain an amide compound as a intermediate, and cyclizing the resulting amide compound under an acetic acid, without further purification, to obtain the compound of formula (1a). The compound of formula (7) may be prepared according to the conventional method or obtained from commercial suppliers. The compound of formula (7) may be employed in an amount of 1 mole per 1 mole of the compound of formula (6). Examples of the base used in the step 5) include diisopropylethylamine, and examples of the solvent include dimethylformamide. The condensation may be conducted for 16 to 24 hours at room temperature, and the cyclization may be conducted for 2 to 4 hours at the temperature of 70 to 75° C.

A compound of formula (1b) may be prepared according to the method shown in Reaction Scheme 2.

Reaction Scheme 2

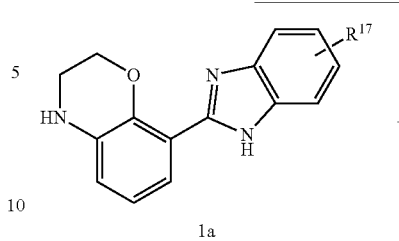

1a

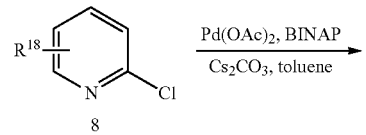

8

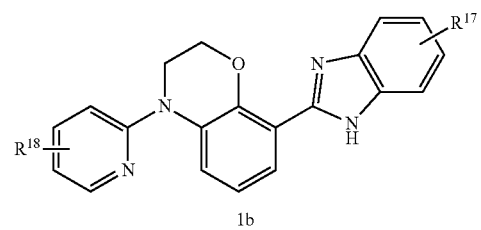

1b

In Reaction Scheme 2, $R^{17}$ and $R^{18}$ have the same meaning as defined above.

As shown in Reaction Scheme 2, the compound of formula (1b) may be prepared by reacting the compound of formula (1a) obtained from the Reaction Scheme 1 with the compound of formula (8) in an organic solvent in the presence of a catalyst and a ligand under a base.

The compound of formula (8) may be prepared according to the conventional method or may be obtained from commercial suppliers. The compound of formula (8) may be employed in an amount of 1 mole per 1 mole of the compound of formula (1a). Examples of the catalyst used include $Pd(OAc)_2$. Examples of the ligand used include 2,2'-bis(diphenylphosphino)-1,1'-binaphtyl. Examples of the base used include $CS_2CO_3$. Examples of the organic solvent used include toluene, 1,4-dioxane, etc. The reaction may be conducted for 12 to 18 hours at the temperature of 90 to 110° C. (Mark M. Hooper et. al., Journal of Organic Chemistry, 68, 2861 (2003)).

A compound of formula (1c) may be prepared according to the method shown in Reaction Scheme 3.

Reaction Scheme 3

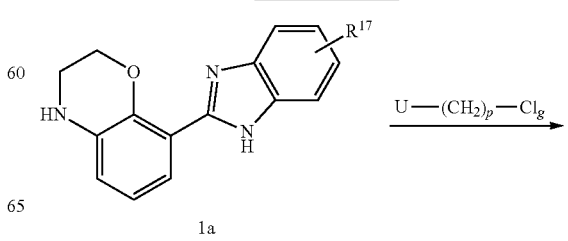

1a

-continued

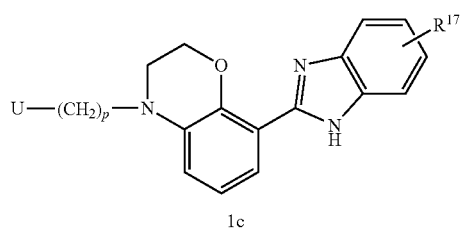

1c

In Reaction Scheme 3, U is morpholinyl or pyridinyl, p is 1 or 2, and $R^{17}$ has the same meaning as defined above.

As shown in Reaction Scheme 3, the compound of formula (1c) may be prepared by reacting the compound of formula (1a) obtained from the reaction scheme 1 with the compound of formula (9) in a organic solvent in the presence of a potassium iodide under a base such as $K_2CO_3$ using a microwave (Juan L. Romera et. al., Tetrahedron Letter, 45, 8797 (2004)). Examples of the organic solvent include dimethylformamide. The reaction may be conducted for 5 to 30 minutes at the temperature of 100 to 120° C.

A compound of formula (1d) may be prepared according to the method shown in Reaction Scheme 4.

Reaction Scheme 4

-continued

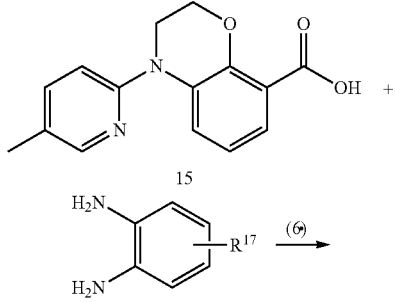

15

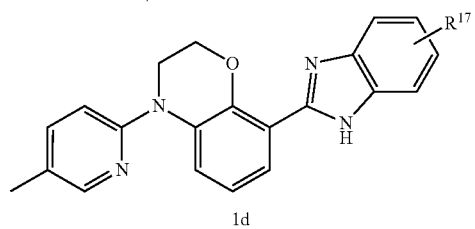

1d

In Reaction Scheme 4, $R^{17}$ has the same meaning as defined above.

As shown in Reaction Scheme 4, in step (1), the compound of formula (10) may be prepared by reacting the compound of the formula (2) in an organic solvent in the presence of a sulfuric acid. Examples of the organic solvent include methanol, ethanol, etc. The reaction may be conducted for 16 to 24 hours under reflux with heat.

In step (2), the compound of formula (11) may be prepared by reducing the compound of formula (10) in an organic solvent under a Pd/C catalyst using a hydrogen reactor. The reduction may be conducted in the same condition as described in step 2) of the Reaction Scheme 1.

In step (3), the compound of formula (12) may be prepared by reacting the compound of the formula (11) with dibromoethane under a base such as $K_2CO_3$. The reaction may be conducted for 2 to 3 hours under reflux with heat.

In step (4), the compound of formula (14) may be prepared by reacting the compound of formula (12) with the compound of formula (13) in an organic solvent in the presence of a catalyst and a ligand, under a base. The compound of formula (13) may be prepared according to the conventional method or may be obtained from commercial suppliers. The compound of formula (13) may be employed in an amount of 1 mole per 1 mole of the compound of formula (12). As examples of the catalyst and ligand used in the step 4), $Pd(OAc)_2$ and 2,2'-bis(diphenylphosphino)-1,1'-binaphtyl can be enumerated respectively. Examples of the base used include $CS_2CO_3$. Examples of the organic solvent used include toluene, 1,4-dioxane, etc. The reaction may be conducted for 12 to 18 hours at the temperature of 90 to 110° C.

In step (5), the compound of formula (15) may be prepared by reacting the compound of formula (14) with sodium hydroxide in an organic solvent such as methanol, Sodium hydroxide may be employed in an amount ranging from 1.5 to 3 mole per 1 mole of the compound of formula (14). The above reaction may be conducted for 3 hours at 60° C.

In step (6), the compound of formula (1d) may be prepared by condensating the compound of formula (15) with the compound of formula (7) and O-(7-azabenzotriazol-1-yl)-N,N, N',N'-tetramethyluronium hexafluorophosphate in a solvent under a base to obtain an amide compound as a intermediate, and cyclizing the resulting amide compound, without further purification, to obtain the compound of formula (1d). The compound of formula (7) may be employed in an amount of 1.1 moles per 1 mole of the compound of formula (15). The condensation and the cyclization may be conducted under the same condition as described in step 5) of the Reaction Scheme 1.
A compound of formula (1e) may be prepared according to the method shown in Reaction Scheme 5.
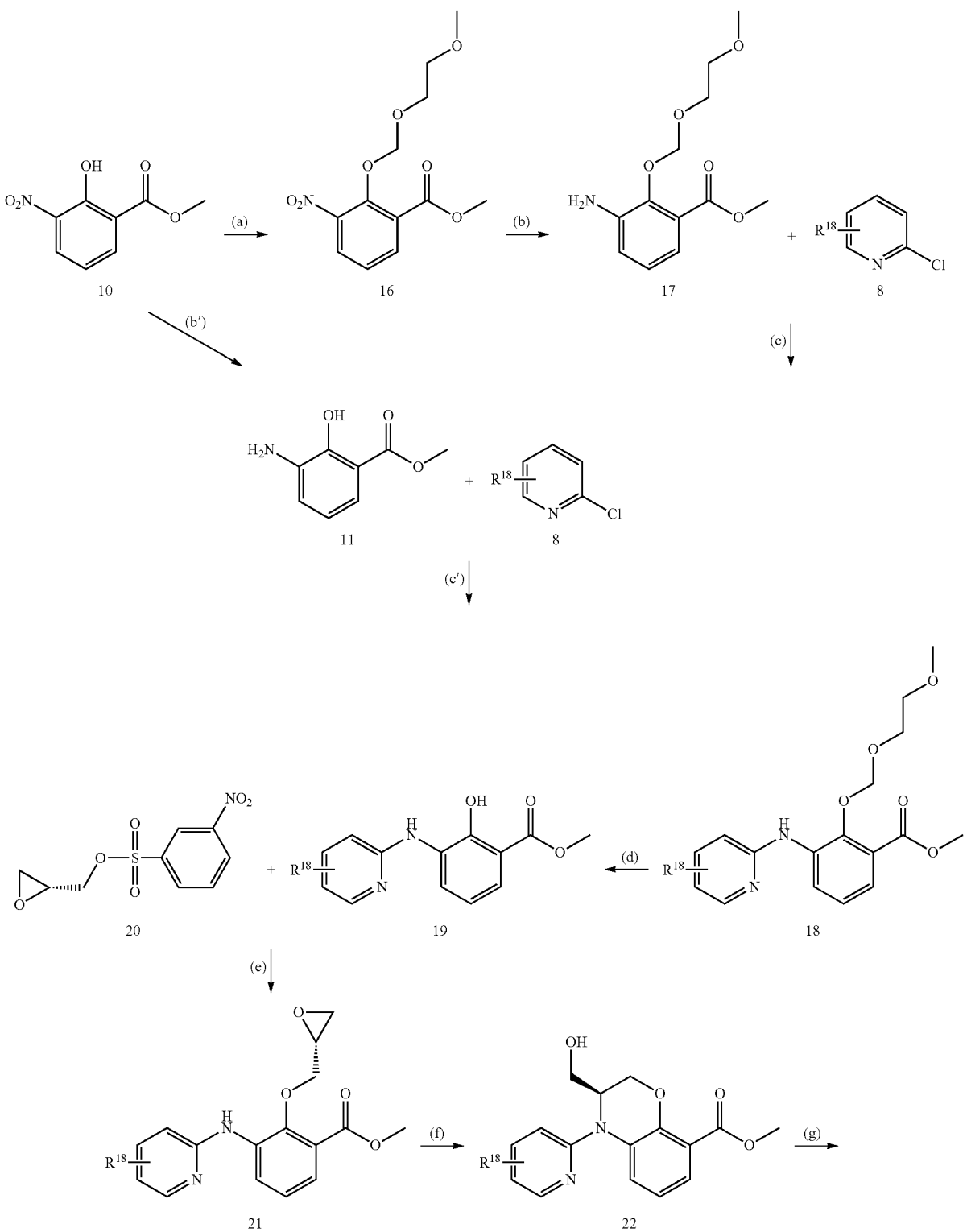

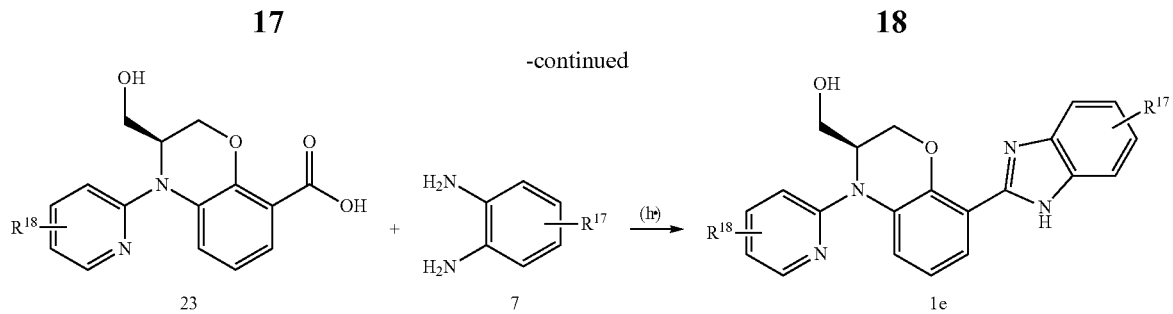

In reaction scheme 5, $R^{17}$ and $R^{18}$ have the same meaning as defined above.

As shown in Reaction Scheme 5, in step (a), the compound of formula (16) may be prepared by reacting the compound of formula (10) in an organic solvent in the presence of a chloromethoxyethoxymethane under a base such as $K_2CO_3$. Example of the organic solvent includes dimethylformamide. The reaction may be conducted for 2 hours at room temperature In steps (b) and (b'), the compounds of formula (11) and (17) may be obtained by reducing the compounds of formula (10) and (16) respectively under the same condition as described in the step 2) of the Reaction Scheme 1.

In steps (c) and (c'), the compounds of formula (18) and (19) may be prepared by reacting the compounds of formula (11) and (17) respectively with compound of formula (8) in an organic solvent in the presence of a catalyst and a ligand under a base such as $CS_2CO_3$. As examples of the catalyst and ligand used in step (c), $Pd(OAc)_2$ and 2,2'-bis(diphenylphosphino)-1,1'-binaphtyl can be enumerated respectively. Examples of the organic solvent include toluene, 1,4-dioxane, etc. The compounds of formula (11) and (17) may be employed in an amount of 1 to 1.2 mole per 1 mole of the compound of formula (8). The reaction may be conducted for 12 to 18 hours at the temperature of 90 to 110° C.

In step (d), the compound of formula (19) may be prepared by reacting the compound of formula (18) in an organic solvent in the presence of a hydrochloric acid. Examples of the organic solvent used in the step 1 include methanol, etc. The above reaction may be conducted for 24 hours at room temperature.

In step (e), the compound of formula (21) may be prepared by reacting the compound of formula (19) with the compound of formula (20) in an organic solvent under a base. The compound of formula (20) may be prepared according to the conventional method or obtained from commercial suppliers. The compound of formula (20) may be employed in an amount of 1 to 1.2 mole per 1 mole of the compound of formula (19). Examples of the base used in the step (e) include $K_2CO_3$, and examples of the solvent include dimethylformamide. The reaction may be conducted for 12 to 16 hours at room temperature In step (f), the compound of formula (22) may be prepared by further reacting the compound of formula (21) in an organic solvent under a base at 100° C., for 2 to 5 hours. Examples of the base include $K_2CO_3$, and example of the solvent includes dimethylformamide.

In step (g), the compound of formula (24) may be prepared by reacting the compound of formula (22) in an organic solvent such as methanol in the presence of a sodium hydroxide at 60° C., for 3 hours.

In step (h), the compound of formula (1e) may be prepared by condensating the compound of formula (23) with the compound of formula (7) under the same condition as described in the step 5) of the Reaction Scheme 1 to obtain an amide compound, and cyclizing the resulting amide compound to obtain the compound of formula (1e).

A compound of formula (1f) may be prepared according to the method shown in Reaction Scheme 6.

Reaction Scheme 6

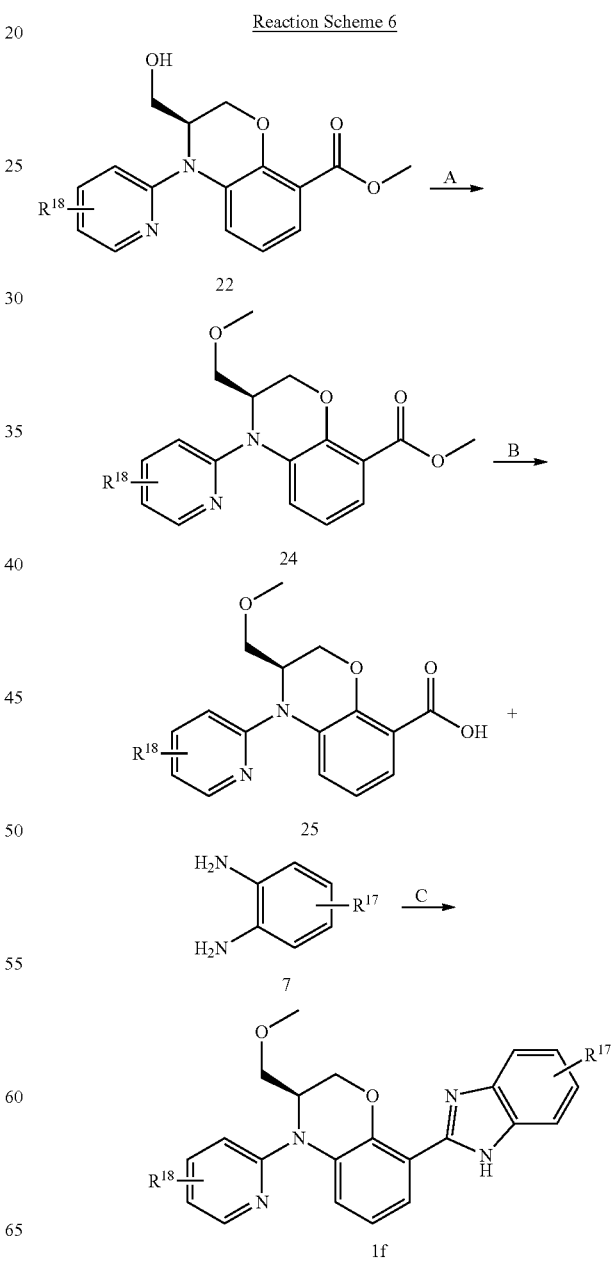

In Reaction Scheme 6, $R^{17}$ and $R^{18}$ have the same meaning as defined above.

As shown in Reaction Scheme 6, in step A, the compound of formula (24) may be prepared by reacting the compound of formula (22) in organic solvent such as tetrahydrofuran, in the presence of a methyl iodide under a base condition. Examples of the base include NaH. The reaction may be conducted for 2 hours at room temperature after addition of the base at 0° C.

In step B, the compound of formula (24) may be prepared by reacting the compound of formula (22) in an organic solvent such as methanol in the presence of a sodium hydroxide at 60° C., for 3 hours.

In step C, the compound of formula (1f) may be prepared by condensating the compound of formula (23) with the compound of formula (7) under the same condition as described in the step 5) of the Reaction Scheme 1 to obtain an amide compound, and cyclizing the resulting amide compound to obtain the compound of formula (1f).

As shown above, the compounds of formula (1) may be in the form of salts, particularly pharmaceutically acceptable salts. The pharmaceutically available salts suitable for use in the present invention are those typically used in the art, such as acid addition salts, and include those disclosed in the literature (J. Pharm. Sci., 66, 1 (1977)). Examples of the pharmaceutically acceptable acid addition salts suitable for use in the present invention include salts of inorganic acids, such as hydrochloric acid, hydrobromic acid, phosphoric acid, orthophosphoric acid, sulfuric acid, and so on; and salts of organic acids, such as methanesulfonic acid, benzenesulfonic acid, toluenesulfonic acid, acetic acid, propionic acid, lactic acid, citric acid, fumaric acid, malic acid, succinic acid, salicylic acid, maleic acid, glycerophosphoric acid, acetylsalicylic acid, and so on.

In addition, pharmaceutically acceptable metal salts may be prepared using bases according to a conventional method. Alkali metal salts or alkaline earth metal salts, for example, may be obtained by dissolving compounds of formula (1) in an excess of an alkali metal hydroxide or alkaline earth metal hydroxide solution, filtering off non-dissolved compound salts, and vaporizing and drying the filtrate. In this regard, sodium, potassium or calcium salts are pharmaceutically suitable metal salts. In addition, silver salts corresponding to the metal salts can be obtained by reacting alkaline metal or alkali earth metal with suitable silver salts (e.g., nitrate).

Pharmaceutically unacceptable salts or solvates of compounds of formula (1) may be useful as intermediates for the preparation of pharmaceutically acceptable salts or solvates of compounds of formula (1), or for the preparation of the compounds themselves of formula (1).

The benzoxazine benzimidazol derivatives of the present invention include a pharmaceutically acceptable salt as well as a solvate and hydrate preparable from them, and a stereoisomer. The solvate, hydrate and stereoisomer may be prepared from the compound of formula (1) according to a conventional method.

The compounds of formula (1) may be prepared in crystalline or non-crystalline forms. If crystalline, the compounds may be optionally hydrated or solvated. Compounds with various amounts of water as well as stoichiometric hydrates of formula (1) fall into the scope of the present invention. Solvates of formula (1) according to the present invention comprise both stoichiometric and non-stoichiometric solvates.

It is believed that, because they possess antagonistic activity against the vanilloid receptor-1, benzoxazine benzimidazol derivatives of formula (1) have potential to be used for the prevention and treatment of indications relevant thereto.

Thus, the present invention also provides a pharmaceutical composition comprising the compound of formula (1), or the pharmaceutically acceptable salt, hydrate, solvate, or isomer thereof as an active ingredient, which is useful for the prevention and treatment of a disease associated with antagonistic activity of vanilloid receptor-1.

The present invention provides a method for preventing or treating indications for which antagonism to the vanilloid receptor-1 is helpful in the therapy thereof in a mammal, which comprises administering the compound of formula (1), or the pharmaceutically acceptable salt, hydrate, solvate or isomer thereof, to the mammal.

Further, the present invention provides a method for inhibiting a vanilloid receptor-1 in a mammal, which comprises administering the compound of formula (1), or the pharmaceutically acceptable salt, hydrate, solvate, or isomer thereof, to the mammal.

As used herein, the term "a disease associated with antagonistic activity of vanilloid receptor-1" refer to acute or chronic disease that require treatment to inhibit activity of vanilloid receptor-1 and exemplary disease include pain such as acute pain, chronic pain, neuropathic pain, postoperative pain; migraine, arthralgia; neuropathy; neuronal damages; diabetic neuropathy; neurological illness; neurodermatitis; stroke; bladder hypersensitivity; obesity; irritable bowel syndrome; respiratory disorders such as cough, asthma, and chronic obstructive pulmonary disease; glaucoma; burns; psoriasis; itching; vomiting; irritation of the skin, eyes, and mucous membranes; and inflammatory diseases such as reflux esophagitis, gastricduodenal ulcers, and inflammatory intestinal diseases.

The pharmaceutical composition of the present invention is generally formulated for oral or peranteral administration according to standard pharmaceutical practice. And these formulations may comprise the above active ingredients, in combination with an additive such as a pharmaceutically acceptable carrier, adjuvant, or diluent. Illustrative, but non-limitative examples of the carrier include physiological saline, polyethylene glycol, ethanol, vegetable oil, and isopropylmyristate. Illustrative, but non-limitative examples of the diluent include lactose, dextrose, scrose, mannitol, sorbitol, cellulose, and/or glycin. For example, the compounds of formula (1), or the pharmaceutically acceptable salt, hydrate, solvate, or isomer thereof, may be dissolved in oils, propyleneglycol, or other solvents, which are usually used for the preparation of injections. For topical use, the compounds of the present invention, or the pharmaceutically acceptable salt, hydrate, solvate, or isomer thereof may be formulated into ointments or creams.

Below, a description will be given of formulation methods and expients, but this description is not intended to limit the present invention.

Although the compounds of formula (1) of the present invention or a pharmaceutically acceptable salt, hydrate, solvate or isomer thereof, themselves are VR1 antagonists, the possibility is not excluded that modified forms thereof in an intracellular environment or metabolites thereof act as effective principles responsible for the medicinal activity.

Pharmaceutical dosage forms of the compounds of formula (1) according to the present invention include pharmaceutically acceptable salts or solvates of the compounds of the present invention alone or in combination with other pharmaceutically active compounds suitably bound or assembled thereto.

For the preparation of injections, the compounds of formula (1) according to the present invention or a pharmaceutically acceptable salt, hydrate, solvate or isomer may be dissolved, suspended or emulsified in an aqueous solvent such as physiological saline, 5% dextrose, etc., or a nonaqueous solvent, such as synthetic fatty acid glyceride, higher fatty acid esters, propylene glycol, etc. The formulation of the present invention may comprise conventional additives such as dissolving agents, isotonic agents, suspensions, emulsifying agents, stabilizer, and preservatives.

Depending on a patient's state and weight, severity of disease, dosage form, and administration route and period, the administration dose of the compounds of formula (1) according to the present invention or the pharmaceutically acceptable salt, hydrate, solvate, or isomer thereof, may be suitably selected by those skilled in the art. For effective therapy, the compounds of formula (1) according to the present invention or the pharmaceutically acceptable salt, hydrate, solvate, or isomer thereof are administered in a dose from 0.0001 to 100 mg/weight kg a day and preferably in a dose from 0.001 to 100 mg/weight kg a day. Administration may be conducted orally or parenterally once or many times in a partitioned manner in a day.

According to the administration method, the pharmaceutical composition may comprise the compound of formula (1) according to the present invention, or the pharmaceutically acceptable salt, hydrate, solvate, or isomer thereof in an amount from 0.001 to 99% by weight, and preferably in an amount from 0.01 to 60% by weight.

The pharmaceutical composition of the present invention may be administered via various routes to mammalians such as mice, rats, livestock, humans, etc. All administration types may be expected, including, for example, an oral administration, a rectal administration, or an intravenous, intramuscular, subcutaneous, intra-endometrial or intracerebroventricular injection.

The present invention is further described and illustrated in preparation example and experimental examples provided below, which are, however, not intended to limit the scope of the present invention.

EXAMPLE 1

Preparation of 8-(5-tert-butyl-1H-benzo[d]imidazol-2-yl)-3,4-dihydro-2H-benzo[b][1,4]oxazine (compound 1a)

(1-1) Preparation of 2-hydroxy-3-nitrobenzoic acid ethyl ester (compound 3)

10.0 g (55 mmol) of 2-hydroxy-3-nitrobenzoic acid was dissolved in 100 mL of ethanol 2 mL of concentrated hydrochloric acid was added dropwise thereto and stirred for 24 hr under heat-reflux. The mixture was cooled to room temperature and concentrated under reduced pressure, followed by dilution with ethyl acetate. The diluted solution was washed with saturated sodium bicarbonate solution and saturated sodium chloride solution, then dried over magnesium sulfate and concentrated under reduced pressure. The resulting residue was subjected to column chromatography (ethyl acetate:hexane=1:4) to obtain the title compound (10.0 g, yield: 86%).
$^1$H NMR (CDCl$_3$) δ: 8.15(d, 2H, J=8.1 Hz), 7.00(t, 1H, J=8.1 Hz), 4.47(q, 2H, J=7.1 Hz), 1.45(t, 3H, J=7.1 Hz)

(1-2) Preparation of 3-amino-2-hydroxybenzoic acid ethyl ester (compound 4)

8.4 g (40 mmol) of 2-hydroxy-3-nitrobenzoic acid ethyl ester obtained in (1-1) was dissolved in 100 mL of methanol, 0.84 g of 5% Pd/C was added thereto and hydrogen gas was filled, followed by stirring for 5 hr at room temperature. 0.5 g of ammonium formate was added thereto, hydrogen gas was filled, and the mixture was further stirred for 24 hr at room temperature. The resulting product was filtered through diatomite to remove the catalyst and concentrated under reduced pressure to obtain the title compound (7.2 g, yield: 99%).

(1-3) Preparation of 3,4-dihydro-2H-benzo[b][1,4]oxazin-8-carboxylic acid ethyl ester (compound 5)

3.6 g (20 mmol) of 3-amino-2-hydroxybenzoic acid ethyl ester obtained in (1-2) was dissolved in 30 mL of dimethylformamide. 5.5 g (40 mmol) of K$_2$CO$_3$ was added thereto, followed by stirring for 10 min at room temperature. 1.9 mL (22 mmol) of dibromoethane was added dropwise to the reaction mixture and stirred for 3 hr under heat-reflux. The obtained product was cooled to room temperature and concentrated under reduced pressure, followed by dilution with ethyl acetate. The diluted solution was washed with saturated sodium bicarbonate solution and saturated sodium chloride solution. The resulting residue was dried over magnesium sulfate and concentrated under reduced pressure to obtain the title compound (3.7 g, yield: 89%).
$^1$H NMR (CDCl$_3$) δ: 7.15(dd, 1H, J=7.2, 2.2 Hz), 6.78-6.70(m, 2H), 4.43-4.30(m, 4H), 3.44(t, 2H, J=4.5 Hz), 1.36(t, 3H, J=7.1 Hz)

(1-4) Preparation of 3,4-dihydro-2H-benzo[b][1,4]oxazin-8-carboxylic acid (compound 6)

2.1 g (10 mmol) of 3,4-dihydro-2H-benzo[b][1,4]oxazin-8-carboxylic acid ethyl ester obtained in (1-3) was dissolved in a mixture of 10 mL of tetrahydrofuran and 10 mL of distilled water. 0.85 g (20 mmol) of lithium hydroxide monohydrate was added thereto and stirred for 8 hr at room temperature. The reaction mixture was concentrated under reduced pressure, followed by dilution with ethyl acetate. The diluted solution was washed with 1N hydrochloric acid solution and saturated sodium chloride solution, dried over magnesium sulfate. The resulting product was concentrated under reduced pressure and crystallized with ethyl acetate/hexane to obtain the title compound (1.6 g, yield: 89%).
$^1$H NMR (CDCl$_3$) δ: 7.52(dd, 1H, J=7.8, 1.6 Hz), 6.90(t, 1H, J=7.8 Hz), 6.81(dd, 1H, J=7.9, 1.6 Hz), 4.50(t, 2H, J=4.5 Hz), 3.55(t, 2H, J=4.5 Hz)

(1-5) Preparation of 8-(5-tert-butyl-1H-benzo[d]imidazol-2-yl)-3,4-dihydro-2H-benzo[b][1,4]oxazine (compound 1a)

3.6 g (20 mmol) of 3,4-dihydro-2H-benzo[b][1,4]oxazin-8-carboxylic acid obtained in (1-4) was dissolved in 50 mL of dimethylformamide. 3.3 g (20 mmol) of 4-tert-butylbenzene-1,2-diamine, 7 mL (40 mmol) of diisopropylethylamine and 11 g (30 mmol) of O-(7-azabenzotriazole-1-yl)-N,N,N',N'-tetramethyluronium hexafluorophosphate were added thereto, and stirred for 3 hr at room temperature. The reaction mixture was diluted with ethyl acetate and washed with saturated sodium bicarbonate solution and saturated sodium chloride solution, followed by drying over magnesium sulfate and concentrating under reduced pressure. The resulting residue was dissolved in acetate/toluene (45 mL/5 mL) and stirred for 4 hr at 70° C., followed by cooling to room temperature and concentrating under reduced pressure. The concentrate was dissolved in ethyl acetate and washed with saturated sodium bicarbonate solution and saturated sodium chloride solution, followed by drying over magnesium sulfate and concentrating under reduced pressure. The obtained residue was subjected to column chromatography (ethyl acetate:hexane=1:1) to obtain the title compound (5.2 g, yield: 85%).

$^1$H NMR (CDCl$_3$) δ: 7.87(dd, 1H, J=7.9, 1.5 Hz), 7.67(d, 1H, J=1.6 Hz), 7.58(d, 1H, J=8.4 Hz), 7.35(dd, 1H, J=8.6, 1.8 Hz), 6.86(t, 1H, J=7.7 Hz), 6.68(dd, 1H, J=7.8, 1.5 Hz), 4.53(t, 2H, J=4.5 Hz), 3.54(t, 2H, J=4.5 Hz), 1.39(s, 9H)

EXAMPLE 2

Preparation of 8-(6-(trifluoromethyl)-1H-benzo[d]imidazol-2-yl)-3,4-dihydro-2H-benzo[b][1,4]oxazine (compound 1a)

The procedure of Example 1 was repeated except for using 4-trifluoromethylbenzene-1,2-diamine instead of 4-tert-butylbenzene-1,2-diamine in (1-5) to obtain the title compound (5.75 g, yield: 90%).

$^1$H NMR (CDCl$_3$) δ: 7.88(dd, 1H, J=7.9, 1.5 Hz), 7.70-7.45(m, 2H), 7.27(dd, 1H, J=8.7, 1.8 Hz), 6.94(t, 1H, J=7.8 Hz), 6.70(dd, 1H, J=7.8, 1.5 Hz), 4.53(t, 2H, J=4.5 Hz), 3.55(t, 2H, J=4.5 Hz)

EXAMPLE 3

Preparation of 8-(6-bromo-1H-benzo[d]imidazol-2-yl)-3,4-dihydro-2H-benzo[b][1,4]oxazine (compound 1a)

The procedure of Example 1 was repeated except for using 4-bromobenzene-1,2-diamine instead of 4-tert-butylbenzene-1,2-diamine in (1-5) to obtain the title compound (6.1 g, yield: 92%).

$^1$H NMR (CDCl$_3$) δ: 7.89(dd, 1H, J=7.9, 1.5 Hz), 7.79(s, 1H), 7.50(s, 1H), 7.35(dd, 1H, J=8.7, 1.7 Hz), 6.94(t, 1H, J=7.8 Hz), 6.70(dd, 1H, J=7.8, 1.5 Hz), 4.54(t, 2H, J=4.5 Hz), 3.57(t, 2H, J=4.5 Hz)

EXAMPLE 4

Preparation of 8-(6-chloro-1H-benzo[d]imidazol-2-yl)-3,4-dihydro-2H-benzo[b][1,4]oxazine (compound 1a)

The procedure of Example 1 was repeated except for using 4-chlorobenzene-1,2-diamine instead of 4-tert-butylbenzene-1,2-diamine in (1-5) to obtain the title compound (5.1 g, yield: 89%).

$^1$H NMR (CDCl$_3$) δ: 7.89(dd, 1H, J=7.9, 1.5 Hz), 7.63-7.53(m, 2H), 7.21(dd, 1H, J=8.7, 2.0 Hz), 6.93(t, 1H, J=7.8 Hz), 6.70(dd, 1H, J=7.8, 1.5 Hz), 4.54(t, 2H, J=4.5 Hz), 3.57(t, 2H, J=4.5 Hz)

EXAMPLE 5

Preparation of 8-(5,6-dichloro-1H-benzo[d]imidazol-2-yl)-3,4-dihydro-2H-benzo[b][1,4]oxazine (compound 1a)

The procedure of Example 1 was repeated except for using 4,5-dichlorobenzene-1,2-diamine instead of 4-tert-butylbenzene-1,2-diamine in (1-5) to obtain the title compound (6.1 g, yield: 95%).

$^1$H NMR (CDCl$_3$) δ: 7.86(dd, 1H, J=7.9, 1.5 Hz), 7.72(s, 2H), 6.93(t, 1H, J=7.9 Hz), 6.71(dd, 1H, J=7.8, 1.5 Hz), 4.54(t, 2H, J=4.5 Hz), 3.57(t, 2H, J=4.5 Hz)

EXAMPLE 6

Preparation of 8-(6-tert-butyl-1H-benzimidazol-2-yl)-4-(3-chloro-pyridin-2-yl)-3,4-dihydro-2H-benzo[1,4]oxazine (compound 1b)

3.1 g (10 mmol) of 4-(5-tert-butyl-1H-benzo[d]imidazol-2-yl)benzenamine (compound 1a) obtained Example 1 was dissolved in 10 mL of toluene. 1.5 g (10 mmol) of 2,3-dichloropyridine (compound 8), 0.1 g (0.5 mmol) of Pd(OAc)$_2$, 0.5 g (0.8 mmol) of 2,2'-bis(diphenylphosphino)-1,1'-binaphthyl and 4.6 g (14 mmol) of Cs$_2$CO$_3$ were added thereto and stirred at 90° C. for 12 hr. The reaction mixture was cooled to room temperature and concentrated under reduced pressure, followed by dilution with ethyl acetate. The resulting product was washed with saturated sodium bicarbonate solution and saturated sodium chloride solution, followed by drying over magnesium sulfate and concentrating under reduced pressure. The resulting residue was subjected to column chromatography (ethyl acetate/hexane=2/3) to obtain the title compound (4.0 g, yield: 95%).

$^1$H NMR (CDCl$_3$) δ: 8.38(dd, 1H, J=4.8, 1.5 Hz), 8.15(dd, 1H, J=7.9, 1.5 Hz), 7.79(dd, 1H, J=7.9, 1.8 Hz), 7.36(dd, 1H, J=8.5, 1.8 Hz), 7.11(m, 1H), 6.93(t, 1H, J=8.0 Hz), 6.01(dd, 1H, J=8.0, 1.5 Hz), 4.68(t, 2H, J=4.5 Hz), 3.96(t, 2H, J=4.5 Hz), 1.41(s, 9H)

EXAMPLE 7

Preparation of 8-(6-tert-butyl-1H-benzimidazol-2-yl)-4-(3-trifluoromethyl-pyridin-2-yl)-3,4-dihydro-2H-benzo[1,4]oxazine (compound 1b)

The procedure of Example 6 was repeated except for using 2-chloro-3-trifluoromethylpyridine instead of 2,3-dichloropyridine in Example 6 to obtain the title compound (4.0 g, yield: 88%).

$^1$H NMR (CDCl$_3$) δ: 8.72(dd, 1H, J=4.8, 1.6 Hz), 8.16-8.11(m, 2H), 7.42-7.34(m, 2H), 6.88(t, 1H, J=8.1 Hz), 6.35(dd, 1H, J=8.1, 1.6 Hz), 4.67(t, 2H, J=4.5 Hz), 3.79(t, 2H, J=4.5 Hz), 1.41(s, 9H)

EXAMPLE 8

Preparation of 8-(6-tert-butyl-1H-benzimidazol-2-yl)-4-(5-trifluoromethyl-pyridin-2-yl)-3,4-dihydro-2H-benzo[1,4]oxazine (compound 1b)

The procedure of Example 6 was repeated except for using 2-chloro-5-trifluoromethyl-pyridine instead of 2,3-dichloropyridine in Example 6 to obtain the title compound (3.8 g, yield: 84%).

$^1$H NMR (CDCl$_3$) δ: 8.56(s, 1H), 8.35(d, 1H, J=7.9 Hz), 7.70(dd, 1H, J=8.9, 2.4 Hz), 7.45-7.33(m, 3H), 7.08(t, 1H, J=8.0 Hz), 4.60(t, 2H, J=4.5 Hz), 4.36(t, 2H, J=4.5 Hz), 1.41(s, 9H)

EXAMPLE 9

Preparation of 8-(6-tert-butyl-1H-benzimidazol-2-yl)-4-(3-chloro-5-trifluoromethyl-pyridin-2-yl)-3,4-dihydro-2H-benzo[1,4]oxazine (compound 1b)

The procedure of Example 6 was repeated except for using 2,3-dichloro-5-trifluoromethyl-pyridine instead of 2,3-dichloropyridine in Example 6 to obtain the title compound (4.6 g, yield: 94%).

¹H NMR (CDCl₃) δ: 8.58(s, 1H), 8.26(d, 1H, J=7.1 Hz), 7.97(d, 1H, J=2.2 Hz), 7.37(dd, 1H, J=8.5, 1.7 Hz), 6.98(t, 1H, J=8.0 Hz), 6.71(dd, 1H, J=8.0, 1.5 Hz), 4.70(t, 2H, J=4.5 Hz), 4.06(t, 2H, J=4.5 Hz), 1.41(s, 9H)

EXAMPLE 10

Preparation of 8-(5-tert-butyl-1H-benzimidazol-2-yl)-4-(5-methyl-pyridin-2-yl)-3,4-dihydro-2H-benzo [1,4]oxazine (compound 1b)

The procedure of Example 6 was repeated except for using 2-chloro-5-methyl-pyridine instead of 2,3-dichloropyridine in Example 6 to obtain the title compound (3.7 g, yield: 92%).
¹H NMR (CDCl₃) δ: 8.16(dd, 1H, J=7.9, 1.5 Hz), 8.17(d, 1H, J=2.2 Hz), 7.40-7.34(m, 3H), 7.17(d, 1H, J=8.5 Hz), 7.00(t, 1H, J=8.0 Hz), 4.55(t, 2H, J=4.5 Hz), 4.19(t, 2H, J=4.5 Hz), 2.28(s, 3H), 1.40(s, 9H)

EXAMPLE 11

Preparation of 8-(5-tert-butyl-1H-benzimidazol-2-yl)-4-(3,5-dichloro-pyridin-2-yl)-3,4-dihydro-2H-benzo[1,4]oxazine (compound 1b)

The procedure of Example 6 was repeated except for using 2,3,5-trichloropyridine instead of 2,3-dichloropyridine in Example 6 to obtain the title compound (4.1 g, yield: 90%).
¹H NMR (CDCl₃) δ: 8.32(d, 1H, J=2.3 Hz), 8.16(t, 1H, J=6.6 Hz), 7.80(d, 1H, J=2.4 Hz), 7.45-7.33(m, 2H), 6.94(t, 1H, J=8.1 Hz), 6.59(d, 1H, J=8.0 Hz), 4.70(t, 2H, J=4.5 Hz), 3.94(t, 2H, J=4.5 Hz), 1.41(s, 9H)

EXAMPLE 12

Preparation of 8-(5-tert-butyl-1H-benzimidazol-2-yl)-4-pyridin-2-yl-3,4-dihydro-2H-benzo[1,4]oxazine (compound 1b)

The procedure of Example 6 was repeated except for using 2-chloropyridine instead of 2,3-dichloropyridine in Example 6 to obtain the title compound (3.3 g, yield: 87%).
¹H NMR (CDCl₃) δ: 8.34(dd, 1H, J=4.9, 1.7 Hz), 8.25(dd, 1H, J=7.9, 1.6 Hz), 7.58-7.51(m, 2H), 7.41(dd, 1H, J=8.0, 1.5 Hz), 7.36(dd, 1H, J=8.5, 1.7 Hz), 7.26(d, 1H, J=8.6 Hz), 7.02(t, 1H, J=8.0 Hz), 6.84(m, 1H), 4.56(t, 2H, J=4.5 Hz), 4.25(t, 2H, J=4.5 Hz), 1.41(s, 9H)

EXAMPLE 13

Preparation of 4-(5-bromo-pyridin-2-yl)-8-(5-tert-butyl-1H-benzimidazol-2-yl)-3,4-dihydro-2H-benzo [1,4]oxazine (compound 1b)

The procedure of Example 6 was repeated except for using 5-bromo-2-chloropyridine instead of 2,3-dichloropyridine in Example 6 to obtain the title compound (4.2 g, yield: 91%).
¹H NMR (CDCl₃) δ: 8.35(d, 1H, J=2.4 Hz), 8.28(dd, 1H, J=1.5 Hz), 7.61(dd, 1H, J=11.5, 2.6 Hz), 7.39-7.35(m, 2H), 7.19(d, 1H, J=9.0 Hz), 7.04(t, 1H, J=8.0 Hz), 4.56(t, 2H, J=4.5 Hz), 4.23(t, 2H, J=4.5 Hz), 1.41(s, 9H)

EXAMPLE 14

Preparation of 8-(5-tert-butyl-1H-benzimidazol-2-yl)-4-(5-chloro-pyridin-2-yl)-3,4-dihydro-2H-benzo [1,4]oxazine (compound 1b)

The procedure of Example 6 was repeated except for using 2,5-dichloropyridine instead of 2,3-dichloropyridine in Example 6 to obtain the title compound (3.6 g, yield: 87%).
¹H NMR (CDCl₃) δ: 8.29-8.26(m, 2H), 7.49(dd, 1H, J=8.9, 2.6 Hz), 7.40-7.34(m, 2H), 7.23(d, 1H, J=8.7 Hz), 7.03(t, 1H, J=8.0 Hz), 4.56(t, 2H, J=4.5 Hz), 4.23(t, 2H, J=4.5 Hz), 1.41(s, 9H)

EXAMPLE 15

Preparation of 6-[8-(5-tert-butyl-1H-benzimidazol-2-yl)-2,3-dihydro-benzo[1,4]oxazin-4-yl]-pyridin-3-yl-methanol (compound 1b)

The procedure of Example 6 was repeated except for using (6-chloropyridin-3-yl)methanol instead of 2,3-dichloropyridine in Example 6 to obtain the title compound (3.9 g, yield: 93%).
¹H NMR (CDCl₃) δ: 8.33(d, 1H, J=2.2 Hz), 8.22(dd, 1H, J=7.9, 1.5 Hz), 7.68(s, 1H), 7.58(dd, 1H, J=8.6, 2.4 Hz), 7.40-7.33(m, 2H), 7.25(d, 1H, J=8.0 Hz), 7.01(t, 1H, J=8.0 Hz), 4.55(t, 2H, J=4.5 Hz), 4.23(t, 2H, J=4.5 Hz), 1.41(s, 9H)

EXAMPLE 16

Preparation of 4-(3-chloro-pyridin-2-yl)-8-(6-trifluoromethyl-1H-benzimidazol-2-yl)-3,4-dihydro-2H-benzo[1,4]oxazine (compound 1b)

The procedure of Example 6 was repeated except for using 8-(6-(trifloromethyl)-1H-benzo[d]imidazol-2-yl)-3,4-dihydro-2H-benzo[b][1,4]oxazine instead of 4-(5-tert-butyl-1H-benzo[d]imidazol-2-yl)benzenamine in Example 6 to obtain the title compound (4.0 g, yield: 94%).
¹H NMR (CDCl₃) δ: 8.39(dd, 1H, J=4.8, 1.7 Hz), 8.13(d, 1H, J=7.9 Hz), 7.80(dd, 1H, J=7.9, 1.7 Hz), 7.61-7.49(m, 1H), 7.13(m, 1H), 6.96(t, 1H, J=8.0 Hz), 6.65(d, 1H, J=8.0 Hz), 4.70(t, 2H, J=4.5 Hz), 3.98(t, 2H, J=4.5 Hz)

EXAMPLE 17

Preparation of 8-(6-trifluoromethyl-1H-benzimidazol-2-yl)-4-(3-trifluoromethyl-pyridin-2-yl)-3,4-dihydro-2H-benzo[1,4]oxazine (compound 1b)

The procedure of Example 6 was repeated except for using 8-(6-(trifloromethyl)-1H-benzo[d]imidazol-2-yl)-3,4-dihydro-2H-benzo[b][1,4]oxazine and 2-chloro-3-trifluoromethylpyridine instead of 445-tert-butyl-1H-benzo[d]imidazol-2-yl)benzenamine and 2,3-dichloropyridine in Example 6 respectively to obtain the title compound (4.2 g, yield: 91%).
¹H NMR (CDCl₃) δ: 10.82(s, 1H), 8.73(s, 1H), 8.19-8.08 (m, 3H), 7.84(d, 1H, J=8.4 Hz), 7.60-7.39(m, 3H), 6.91(t, 1H, J=8.0 Hz), 6.39(d, 1H, J=7.9 Hz), 4.70(t, 2H, J=4.5 Hz), 3.89(t, 2H, J=4.5 Hz)

EXAMPLE 18

Preparation of 4-(3,5-dichloro-pyridin-2-yl)-8-(6-trifluoromethyl-1H-benzimidazol-2-yl)-3,4-dihydro-2H-benzo[1,4]oxazine (compound 1b)

The procedure of Example 6 was repeated except for using 8-(6-(trifloromethyl)-1H-benzo[d]imidazol-2-yl)-3,4-dihydro-2H-benzo[b][1,4]oxazine and 2,3,5-trichloropyridine instead of 4-(5-tert-butyl-1H-benzo[d]imidazol-2-yl)benzenamine and 2,3-dichloropyridine in Example 6 respectively to obtain the title compound (4.1 g, yield: 89%).

$^1$H NMR (CDCl$_3$) δ: 8.33(d, 1H, J=2.3 Hz), 8.16(d, 1H, J=7.7 Hz), 8.10(s, 1H), 7.81(d, 1H, J=2.3 Hz), 7.61-7.50(m, 2H), 6.97(t, 1H, J=8.0 Hz), 6.64(d, 1H, J=8.4 Hz), 4.70(t, 2H, J=4.5 Hz), 3.96(t, 2H, J=4.5 Hz)

EXAMPLE 19

Preparation of 4-(5-bromo-pyridin-2-yl)-8-(6-trifluoromethyl-1H-benzimidazol-2-yl)-3,4-dihydro-2H-benzo[1,4]oxazine (compound 1b)

The procedure of Example 6 was repeated except for using 8-(6-(trifloromethyl)-1H-benzo[d]imidazol-2-yl)-3,4-dihydro-2H-benzo[b][1,4]oxazine and 5-bromo-2-chloropyridine instead of 4-(5-tert-butyl-1H-benzo[d]imidazol-2-yl)benzenamine and 2,3-dichloropyridine in Example 6 respectively to obtain the title compound (4.3 g, yield: 91%).

$^1$H NMR (CDCl$_3$) δ: 8.36(d, 1H, J=2.3 Hz), 8.28(dd, 1H, J=7.9, 1.4 Hz), 8.11(s, 1H), 7.63(dd, 1H, J=8.9, 2.5 Hz), 7.55-7.49(m, 2H), 7.44(dd, 1H, J=8.1, 1.4 Hz), 7.18(d, 1H, J=8.9 Hz), 7.07(t, 1H, J=8.0 Hz), 4.59(t, 2H, J=4.5 Hz), 4.24(t, 2H, J=4.5 Hz)

EXAMPLE 20

Preparation of 4-(5-chloro-pyridin-2-yl)-8-(6-trifluoromethyl-1H-benzimidazol-2-yl)-3,4-dihydro-2H-benzo[1,4]oxazine (compound 1b)

The procedure of Example 6 was repeated except for using 8-(6-(trifloromethyl)-1H-benzo[d]imidazol-2-yl)-3,4-dihydro-2H-benzo[b][1,4]oxazine and 2,5-dichloropyridine instead of 4-(5-tert-butyl-1H-benzo[d]imidazol-2-yl)benzenamine and 2,3-dichloropyridine in Example 6 respectively to obtain the title compound (4.0 g, yield: 92%).

$^1$H NMR (CDCl$_3$) δ: 8.29-8.24(m, 2H), 8.11(s, 1H), 7.96-7.91(m, 1H), 7.61-7.49(m, 2H), 7.43(dd, 1H, J=8.0, 1.4 Hz), 7.21(d, 1H, J=9.1 Hz), 7.07(t, 1H, J=8.0 Hz), 4.60(t, 2H, J=4.5 Hz), 4.24(t, 2H, J=4.5 Hz)

EXAMPLE 21

Preparation of 8-(6-bromo-1H-benzimidazol-2-yl)-4-(3-chloro-pyridin-2-yl)-3,4-dihydro-2H-benzo[1,4]oxazine (compound 1b)

The procedure of Example 6 was repeated except for using 8-(6-bromo-1H-benzo[d]imidazol-2-yl)-3,4-dihydro-2H-benzo[b][1,4]oxazine instead of 4-(5-tert-butyl-1H-benzo[d]imidazol-2-yl)benzenamine in Example 6 to obtain the title compound (3.9 g, yield: 88%).

$^1$H NMR (CDCl$_3$) δ: 8.39(dd, 1H, J=4.8, 1.6 Hz), 8.10(dd, 1H, J=7.9, 1.6 Hz), 7.80(dd, 1H, J=7.9, 1.6 Hz), 7.67(s, 1H), 7.37(m, 1H), 7.14(m, 1H), 6.94(t, 1H, J=8.1 Hz), 6.63(dd, 1H, J=8.1, 1.5 Hz), 4.69(t, 2H, J=4.5 Hz), 3.98(t, 2H, J=4.5 Hz)

EXAMPLE 22

Preparation of 8-(6-chloro-1H-benzimidazol-2-yl)-4-(3-chloro-pyridin-2-yl)-3,4-dihydro-2H-benzo[1,4]oxazine (compound 1b)

The procedure of Example 6 was repeated except for using 8-(6-chloro-1H-benzo[d]imidazol-2-yl)-3,4-dihydro-2H-benzo[b][1,4]oxazine instead of 445-tert-butyl-1H-benzo[d]imidazol-2-yl)benzenamine in Example 6 to obtain the title compound (3.7 g, yield: 94%).

$^1$H NMR (CDCl$_3$) δ: 8.38(dd, 1H, J=4.8, 1.7 Hz), 8.10(dd, 1H, J=7.9, 1.5 Hz), 7.79(dd, 1H, J=7.9, 1.6 Hz), 7.13-7.08(m, 1H), 6.94(t, 1H, J=8.0 Hz), 6.62(dd, 1H, J=8.2, 1.5 Hz), 4.68(t, 2H, J=4.5 Hz), 3.97(t, 2H, J=4.5 Hz)

EXAMPLE 23

Preparation of 8-(5,6-dichloro-1H-benzimidazol-2-yl)-4-(2-morpholine-4-yl-ethyl)-3,4-dihydro-2H-benzo[1,4]oxazine (compound 1c)

4.5 g (14 mmol) of 8-(5,6-dichloro-1H-benzo[d]imidazol-2-yl)-3,4-dihydro-2H-benzo[b][1,4]oxazine (compound 1a) obtained in Example 5 was dissolved in 100 mL of dimethylformamide. 1.3 g (7 mmol) of 4-(2-chloroethyl)morpholine, 0.58 g (3.5 mmol) of potassium iodide and 0.97 g (7 mmol) of K$_2$CO$_3$ were added thereto, followed by irradiation of microwave at 110° C. for 10 min. The reaction mixture was concentrated under reduced pressure, followed by dilution with ethyl acetate. The resulting product was washed with distilled water and saturated sodium chloride solution, followed by drying over magnesium sulfate and concentrating under reduced pressure. The resulting residue was subjected to column chromatography (ethyl acetate/hexane=1/1) to obtain the title compound (2.8 g, yield: 91%).

$^1$H NMR (CDCl$_3$) δ: 7.87(s, 1H), 7.82(dd, 1H, J=8.0, 1.6 Hz), 7.58(s, 1H), 7.00(t, 1H, J=8.2 Hz), 6.79(dd, 1H, J=8.2, 1.7 Hz), 4.50(t, 2H, J=4.5 Hz), 3.79-3.65(m, 4H), 3.57(t, 2H, J=4.5 Hz), 2.63-2.45(m, 6H), 2.30(t, 2H, J=4.7 Hz)

EXAMPLE 24

Preparation of 8-(5,6-dichloro-1H-benzimidazol-2-yl)-4-pyridin-3-yl-methyl-3,4-dihydro-2H-benzo[1,4]oxazine (compound 1c)

The procedure of Example 23 was repeated except for using 3-chloromethylpyridine instead of 4-(2-chloroethyl)morpholine in Example 23 to obtain the title compound (2.5 g, yield: 87%).

$^1$H NMR (CDCl$_3$) δ: 8.61-8.55(m, 2H), 7.87(dd, 1H, J=4.8, 1.5 Hz), 7.64(d, 1H, J=8.0 Hz), 7.32-7.27(m, 1H), 6.97(t, 1H, J=8.0 Hz), 6.77(dd, 1H, J=8.1, 1.4 Hz), 4.59-4.52(m, 4H), 3.53(t, 2H, J=4.5 Hz)

EXAMPLE 25

Preparation of 4-(5-methyl-pyridin-2-yl)-8-(6-trifluoromethyl-1H-benzimidazol-2-yl)-3,4-dihydro-2H-benzo[1,4]oxazine (compound 1c)

(25-1) Preparation of 2-hydroxy-3-nitrobenzoic acid methyl ester (compound 10)

20 g (109 mmol) of 2-hydroxy-3-nitrobenzoic acid was dissolved in 150 mL of methanol, 7 mL of strong sulfuric acid was added dropwise thereto. The mixture was stirred under heat-reflux for 24 hr. The mixture was cooled to 0° C., filtered and washed with distilled water, followed by drying under vacuum to obtain the title compound (20 g, yield: 93%)

$^1$H NMR (CDCl$_3$) δ: 8.14(d, 2H, J=8.0 Hz), 7.00(t, 1H, J=8.1 Hz), 3.89(s, 3H)

(25-2) Preparation of 3-amino-2-hydroxybenzoic acid methyl ester (compound 11)

10 g (51 mmol) of 2-hydroxy-3-nitrobenzoic acid methyl ester obtained in (25-1) was dissolved in 100 mL of methanol, 1.0 g of 5% Pd/C was added thereto, hydrogen gas was filled, and stirred at room temperature for 24 hr. The reaction mixture was filtered through diatomite to remove the catalyst, followed by concentration under reduced pressure to obtain the title compound (8.4 g, yield: 99%)

$^1$H NMR (CDCl$_3$) δ: 7.29(d, 1H, J=7.7 Hz), 6.93(d, 1H, J=7.7 Hz), 6.71(t, 1H, J=7.9 Hz), 3.88(s, 3H)

(25-3) Preparation of 3,4-dihydro-2H-benzo[b][1,4]oxazin-8-carboxylic acid methyl ester (compound 12)

1.8 g (10 mmol) of 3-amino-2-hydroxybenzoic acid methyl ester obtained in (25-2) was dissolved in 15 mL of dimethylformamide. 0.28 g (20 mmol) of K$_2$CO$_3$ was added thereto and stirred at room temperature for 10 min. 0.95 mL (11 mmol) of dibromoethane was added dropwise to the reaction mixture, followed by stirring for 3 hr under heat-reflux. The reaction mixture was cooled to room temperature and concentrated under reduced pressure, followed by dilution with ethyl acetate and washing with saturated sodium bicarbonate solution and saturated sodium chloride solution. The resulting residue was dried over magnesium sulfate and concentrated under reduced pressure to obtain the title compound (1.8 g, yield: 95%)

$^1$H NMR (CDCl$_3$) δ: 7.16(dd, 1H, J=7.2, 2.1 Hz), 6.77-6.70(m, 2H), 3.87(s, 3H)

(25-4) Preparation of 4-(5-methylpyridin-2-yl)-3,4-dihydro-2H-benzo[b][1,4]oxazin-8-carboxylic acid methyl ester (compound 14)

1.14 g (5.9 mmol) of 3,4-dihydro-2H-benzo[b][1,4]oxazin-8-carboxylic acid methyl ester obtained in (25-3) was dissolved in 7 mL of 1,4-dioxane. 0.64 mL (5.9 mmol) of 2-chloro-5-methylpyridine, 0.13 g (0.59 mmol) of Pd(OAc)$_2$, 0.37 g (0.59 mmol) of 2,2'-bis(diphenylphosphino)-1,1'-binaphtyl and 3.85 g (11.8 mmol) of Cs$_2$CO$_3$ was added thereto and stirred at 90° C. for 12 hr. The reaction mixture was cooled to room temperature and filtered to remove Cs$_2$CO$_3$. The filtrate was concentrated under reduced pressure, then diluted with ethyl acetate, and washed with saturated sodium bicarbonate solution and saturated sodium chloride solution, followed by drying over magnesium sulfate and concentrating under reduced pressure. The resulting residue was subjected to column chromatography (ethyl acetate/hexane=2/3) to obtain the title compound (1.5 g, yield: 91%).

$^1$H NMR (CDCl$_3$) δ: 8.15(s, 1H), 7.44-7.39(m, 2H), 7.36 (dd, 1H, J=5.7, 3.3 Hz), 7.06(d, 1H, J=8.5 Hz), 6.82(t, 1H, J=7.9 Hz), 4.36(t, 2H, J=4.5 Hz), 4.06(t, 2H, J=4.5 Hz), 3.90(s, 3H), 2.26(s, 3H)

(25-5) Preparation of 4-(5-methylpyridin-2-yl)-3,4-dihydro-2H-benzo[b][1,4]oxazin-8-carboxylic acid (compound 15)

1.3 g (4.6 mmol) of 4-(5-methylpyridin-2-yl)-3,4-dihydro-2H-benzo[b][1,4]oxazin-8-carboxylic acid methyl ester obtained in (25-4) was dissolved in 15 mL of methanol 2 mL of 4N sodium hydroxide was added dropwise thereto. The reaction mixture was stirred at 60° C. for 3 hr, then cooled to room temperature, and neutralized by addition of 8 mL of 1N hydrochloric acid solution. The resulting solids were filtered and washed with distilled water, followed by drying under vacuum to obtain the title compound (1.1 g, yield: 89%).

$^1$H NMR (CDCl$_3$) δ: 8.18(d, 1H, J=2.0 Hz), 7.79(dd, 1H, J=7.8, 1.5 Hz), 7.50(dd, 1H, J=8.2, 1.6 Hz), 7.40(dd, 1H, J=8.5, 2.3 Hz), 7.09(d, 1H, J=8.4 Hz), 6.98(t, 1H, J=8.0 Hz), 4.53(t, 2H, J=4.5 Hz), 4.14(t, 2H, J=4.5 Hz), 2.28(s, 3H)

(25-6) Preparation of 4-(5-methyl-pyridin-2-yl)-8-(6-trifluoromethyl-1H-benzimidazol-2-yl)-3,4-dihydro-2H-benzo[1,4]oxazine (compound 1c)

To 2.7 g (10 mmol) of 4-(5-methylpyridin-2-yl)-3,4-dihydro-2H-benzo[b][1,4]oxazin-8-carboxylic acid obtained in (25-5) were added 1.9 g (11 mmol) of 4-(trifluoromethyl)benzene-1,2-diamine, 3.5 mL (20 mmol) of diisopropylethylamine and 5.7 g (15 mmol) of O-(7-azabenzotriazole-1-yl)-N,N,N',N'-tetramethyluronium hexafluorophosphate, and stirred at room temperature for 3 hr. The reaction mixture was diluted with ethyl acetate, washed with saturated sodium bicarbonate solution and saturated sodium chloride solution, followed by drying over magnesium sulfate and concentrating under reduced pressure. The resulting residue was dissolved in acetate/toluene (90 mL/10 mL) and stirred at 75° C. for 4 hr, followed by cooling to room temperature and concentrating under reduced pressure. The concentrate was dissolved in ethyl acetate, washed with saturated sodium bicarbonate solution and saturated sodium chloride solution, followed by drying over magnesium sulfate and concentrating under reduced pressure. The resulting residue was subjected to column chromatography (ethyl acetate/hexane=2/3) to obtain the title compound (3.9 g, yield: 94%).

$^1$H NMR (CDCl$_3$) δ: 8.23-8.18(m, 2H), 7.43-7.38(m, 2H), 7.16(d, 1H, J=8.4 Hz), 7.03(t, 1H, J=8.0 Hz), 4.58(t, 2H, J=4.5 Hz), 4.20(t, 2H, J=4.5 Hz), 2.29(s, 3H)

EXAMPLE 26

Preparation of 8-(6-bromo-1H-benzimidazol-2-yl)-4-(5-methyl-pyridin-2-yl)-3,4-dihydro-2H-benzo[1,4]oxazine (compound 1d)

The procedure of Example 25 was repeated except for using 4-bromobenzene-1,2-diamine instead of 4-(trifluoromethyl)benzene-1,2-diamine in (25-6) to obtain the title compound (3.7 g, yield: 88%).

$^1$H NMR (CD$_3$OD): 8.20-8.15(m, 2H), 7.40-7.36(m, 3H), 7.15(d, 1H, J=8.4 Hz), 7.00(t, 1H, J=8.0 Hz), 4.55(t, 2H, J=4.5 Hz), 4.18(t, 2H, J=4.5 Hz), 2.28(s, 3H)

EXAMPLE 27

Preparation of 8-(5-chloro-1H-benzimidazol-2-yl)-4-(5-methyl-pyridin-2-yl)-3,4-dihydro-2H-benzo[1,4]oxazine (compound 1d)

The procedure of Example 25 was repeated except for using 4-chlorobenzene-1,2-diamine instead of 4-(trifluoromethyl)benzene-1,2-diamine in (25-6) to obtain the title compound (3.6 g, yield: 96%).

$^1$H NMR (CD$_3$OD): 8.19-8.16(m, 2H), 7.49-7.37(m, 2H), 7.16(d, 1H, J=8.5 Hz), 7.01(t, 1H, J=8.0 Hz), 4.56(t, 2H, J=4.5 Hz), 4.19(t, 2H, J=4.5 Hz), 2.28(s, 3H)

EXAMPLE 28

Preparation of 8-(5,6-dichloro-1H-benzimidazol-2-yl)-4-(5-methyl-pyridin-2-yl)-3,4-dihydro-2H-benzo[1,4]oxazine (compound 1d)

The procedure of Example 25 was repeated except for using 4,5-dichlorobenzene-1,2-diamine instead of 4-(trifluoromethyl)benzene-1,2-diamine in (25-6) to obtain the title compound (3.7 g, yield: 91%).
$^1$H NMR (CD$_3$OD): 8.18(s, 1H), 8.15(d, 1H, J=8.0 Hz), 7.89(s, 1H), 7.61(s, 1H), 7.40(d, 1H, J=8.2 Hz), 7.15(d, 1H, J=8.4 Hz), 7.02(t, 1H, J=7.9 Hz), 4.57(t, 2H, J=4.5 Hz), 4.19(t, 2H, J=4.5 Hz), 2.28(s, 3H)

EXAMPLE 29

Preparation of 8-(4-chloro-6-trifluoromethyl-1H-benzimidazol-2-yl)-4-(5-methyl-pyridin-2-yl)-3,4-dihydro-2H-benzo[1,4]oxazine (compound 1d)

The procedure of Example 25 was repeated except for using 3-chloro-5-trifluoromethylbenzene-1,2-diamine instead of 4-(trifluoromethyl)benzene-1,2-diamine in (25-6) to obtain the title compound (3.9 g, yield: 87%).
$^1$H NMR (CD$_3$OD): 9.52(s, 1H), 8.18(d, 1H, J=2.1 Hz), 7.88(dd, 1H, J=7.7, 1.6 Hz), 7.57(s, 1H), 7.48-7.37(m, 3H), 7.10(d, 1H, J=8.4 Hz), 6.99(t, 1H, J=8.0 Hz), 4.52(t, 2H, J=4.5 Hz), 4.20(t, 2H, J=4.5 Hz), 2.28(s, 3H)

EXAMPLE 30

Preparation of 8-(4,6-bis-trifluoromethyl-1H-benzimidazol-2-yl)-4-(5-methyl-pyridin-2-yl)-3,4-dihydro-2H-benzo[1,4]oxazine (compound 1d)

The procedure of Example 25 was repeated except for using 3,5-bis-5-trifluoromethylbenzene-1,2-diamine instead of 4-(trifluoromethyl)benzene-1,2-diamine in (25-6) to obtain the title compound (4.5 g, yield: 95%).
$^1$H NMR (CD$_3$OD): 9.37(s, 1H), 8.20-8.17(m, 2H), 7.88 (dd, 1H, J=7.9, 1.6 Hz), 7.85(s, 1H), 7.64(s, 1H), 7.48(dd, 1H, J=8.1, 1.6 Hz), 7.40(dd, 1H, J=8.7, 2.7 Hz), 7.11(d, 1H, J=8.4 Hz), 7.01(t, 1H, J=8.0 Hz), 4.52(t, 2H, J=4.5 Hz), 4.17(t, 2H, J=4.5 Hz), 2.28(s, 3H)

EXAMPLE 31

Preparation of 8-(4-bromo-6-trifluoromethyl-1H-benzimidazol-2-yl)-4-(5-methyl-pyridin-2-yl)-3,4-dihydro-2H-benzo[1,4]oxazine (compound 1d)

The procedure of Example 25 was repeated except for using 3-bromo-5-trifluoromethylbenzene-1,2-diamine instead of 4-(trifluoromethyl)benzene-1,2-diamine in (25-6) to obtain the title compound (4.4 g, yield: 89%).
$^1$H NMR (CD$_3$OD): 9.50(s, 1H), 8.18(s, 1H), 7.89(d, 1H, J=7.9 Hz), 7.62(s, 2H), 7.49-7.38(m, 3H), 7.10(d, 1H, J=8.5 Hz), 7.00(t, 1H, J=7.1 Hz), 4.52(t, 2H, J=4.5 Hz), 4.17(t, 2H, J=4.5 Hz), 2.29(s, 3H)

EXAMPLE 32

Preparation of 8-(4,6-dibromo-1H-benzimidazol-2-yl)-4-(5-methyl-pyridin-2-yl)-3,4-dihydro-2H-benzo[1,4]oxazine (compound 1d)

The procedure of Example 25 was repeated except for using 3,5-dibromobenzene-1,2-diamine instead of 4-(trifluoromethyl)benzene-1,2-diamine in (25-6) to obtain the title compound (4.7 g, yield: 93%).
$^1$H NMR (CD$_3$OD): 8.18(s, 1H), 7.42-7.38(m, 2H), 7.12(d, 1H, J=8.7 Hz), 7.00(t, 1H, J=8.0 Hz), 4.57(t, 2H, J=4.5 Hz), 4.19(t, 2H, J=4.5 Hz), 2.28(s, 3H)

EXAMPLE 33

Preparation of 8-(6-bromo-4-fluoro-1H-benzimidazol-2-yl)-4-(5-methyl-pyridin-2-yl)-3,4-dihydro-2H-benzo[1,4]oxazine (compound 1d)

The procedure of Example 25 was repeated except for using 5-bromo-3-fluorobenzene-1,2-diamine instead of 4-(trifluoromethyl)benzene-1,2-diamine in (25-6) to obtain the title compound (4.1 g, yield: 94%).
$^1$H NMR (CD$_3$OD): 8.24(dd, 1H, J=7.9, 1.5 Hz), 8.18(s, 1H), 7.46-7.38(m, 2H), 7.17-7.12(m, 2H), 7.01(t, 1H, J=8.0 Hz), 4.56(t, 2H, J=4.5 Hz), 4.19(t, 2H, J=4.5 Hz), 2.32(s, 3H)

EXAMPLE 34

Preparation of [(S)-8-(6-tert-butyl-1H-benzimidazol-2-yl)-4-(5-methyl-pyridin-2-yl)-3,4-dihydro-2H-benzo[1,4]oxazin-3-yl]-methanol (compound 1e)

(34-1) Preparation of 2-((2-methoxyethoxy)methoxy)-3-nitrobenzoic acid methyl ester (compound 16)

9.9 g (50 mmol) of 2-hydroxy-3-nitrobenzoic acid methyl ester was dissolved in 100 mL of dimethylformamide. 7.6 g (55 mmol) of K$_2$CO$_3$ and 6.3 mL (55 mmol) of chloromethoxyethoxymethane were added thereto and stirred at room temperature for 2 hr. The reaction mixture was concentrated under reduced pressure, followed by dilution with ethyl acetate and washing with distilled water and saturated sodium chloride solution. The resulting residue was dried over magnesium sulfate and concentrated under reduced pressure to obtain the title compound (14.0 g, yield: 98%).
$^1$H NMR (CDCl$_3$) δ: 8.03(dd, 1H, J=7.9, 1.8 Hz), 7.88(dd, 1H, J=8.1, 1.8 Hz), 7.29(t, 1H, J=8.0 Hz), 5.25(s, 2H), 3.92(s, 3H), 3.84(t, 2H, J=4.5 Hz), 3.53(t, 2H, J=4.5 Hz), 3.36(s, 3H)

(34-2) Preparation of 3-amino-2((2-methoxyethoxy)methoxy)benzoic acid methyl ester (compound 17)

5.0 g (17.5 mmol) of 2-((2-methoxyethoxy)methoxy)-3-nitrobenzoic acid methyl ester obtained in (34-1) was dissolved in 50 mL of methanol, 0.5 g of 5% Pd/C was added thereto, hydrogen gas was filled and stirred at room temperature for 24 hr. The reaction mixture was filtered through diatomite to remove the catalyst, followed by concentration under reduced pressure. The resulting residue was subjected to column chromatography (ethyl acetate/hexane=1/1) to obtain the title compound (4.2 g, yield: 95%)
$^1$H NMR (CDCl$_3$) δ: 7.16(dd, 1H, J=7.6, 1.7 Hz), 6.95(t, 1H, J=7.8 Hz), 6.88(dd, 1H, J=7.9, 1.7 Hz), 5.17(s, 2H), 4.20(bs, 2H), 3.94(t, 2H, J=4.5 Hz), 3.87(s, 3H), 3.60(t, 2H, J=4.5 Hz), 3.39(s, 3H)

(34-3) Preparation of 2-((2-methoxyethoxy)methoxy-3-(5-methylpyridin-2-ylamino)benzoic acid methyl ester (compound 18)

1.25 g (4.9 mmol) of 3-amino-2((2-methoxyethoxy)methoxy)benzoic acid methyl ester obtained in (34-2) was dissolved in 10 mL of 1,4-dioxane. 0.54 mL (4.9 mmol) of 2-chloro-5-methylpyridine, 0.11 g (0.49 mmol) of Pd(OAc)$_2$, 0.31 g (0.49 mmol) of 2,2'-bis(diphenylphosphino)-1,1'-binaphthyl and 3.85 g (9.8 mmol) of Cs$_2$CO$_3$ were added thereto, and stirred at 90° C. for 12 hr. The reaction mixture was cooled to room temperature and concentrated under reduced pressure, followed by dilution with ethyl acetate and washing with saturated sodium bicarbonate solution and saturated sodium chloride solution. The washed material was dried over magnesium sulfate and concentrated at reduced pressure. Then, the resulting residue was subjected to column chromatography (ethyl acetated/hexane=1/2) to obtain the title compound (1.6 g, yield: 92%).

$^1$H NMR (CDCl$_3$) δ: 8.51(dd, 1H, J=6.6, 1.3 Hz), 8.06(s, 1H), 7.39-7.33(m, 2H), 7.14(t, 1H, J=8.0 Hz), 6.80(d, 1H, J=8.4 Hz), 5.22(s, 2H), 3.93(t, 2H, J=4.5 Hz), 3.89(s, 3H), 3.61(t, 2H, J=4.5 Hz), 3.36(s, 3H), 2.24(s, 3H)

(34-4) Preparation of 2-hydroxy-3-(5-methylpyridin-2-ylamino)benzoic methyl ester (compound 19)

1.3 g (3.7 mmol) of 2-((2-methoxyethoxy)methoxy-3-(5-methylpyridin-2-ylamino)benzoic acid methyl ester obtained (34-3) was dissolved in 20 mL of methanol 2 mL of 6N hydrochloric acid solution was added thereto and stirred at 40° C. for 30 min. The reaction mixture was cooled to room temperature and concentrated at reduced pressure, then diluted with ethyl acetate and washed with distilled water and saturated sodium chloride solution, followed by drying over magnesium sulfate and concentration under reduced pressure. The resulting residue was subjected to column chromatography (ethyl acetate/hexane=1/2) to obtain the title compound (0.90 g, yield: 90%).

$^1$H NMR (CDCl$_3$) δ: 8.45(dd, 1H, J=8.0, 1.5 Hz), 8.08(s, 1H), 7.39(dd, 1H, J=8.1, 1.4 Hz), 7.35(dd, 1H, J=8.4, 2.3 Hz), 6.88(t, 1H, J=8.0 Hz), 7.24(d, 1H, J=8.4 Hz), 3.97(s, 3H), 2.24(s, 3H)

(34-5) Preparation of (R)-3-(5-methylpyridin-2-ylamino)-2-(oxirane-2-ylmethoxy)benzoic acid methyl ester (compound 21)

0.85 g (3.3 mmol) of 2-hydroxy-3-(5-methylpyridin-2-ylamino)benzoic methyl ester obtained in (34-4) was dissolved in 10 mL of dimethylformamide. 1.0 g (4 mmol) of (R)-glycidyl nosylate and 0.5 g (3.6 mmol) of K$_2$CO$_3$ were added thereto and stirred at room temperature for 12 hr. The reaction mixture was concentrated under reduced pressure, then diluted with ethyl acetate and washed with distilled water and saturated sodium chloride solution, followed by drying over magnesium sulfate and concentration under reduced temperature. The resulting residue was subjected to column chromatography (ethyl acetate/hexane=1/2) to obtain the title compound (0.90 g, yield: 85%).

$^1$H NMR (CDCl$_3$) δ: 7.69(dd, 1H, J=8.2, 1.6 Hz), 8.07(d, 1H, J=2.0 Hz), 7.81(s, 1H), 7.38-7.30(m, 2H), 7.15(t, 1H, J=8.0 Hz), 6.87(d, 1H, J=8.4 Hz), 4.32-4.22(m, 2H), 3.91(s, 3H), 3.43-3.39(m, 1H), 3.07-3.04(m, 1H), 2.97(t, 1H, J=9.1 Hz), 2.24(s, 3H)

(34-6) Preparation (S)-3-(hydroxymethyl)-4-(5-methylpyridin-2-yl)-3,4-dihydro-2H-benzo[b][1,4]oxazin-8-carboxylic acid methyl ester (compound 22)

0.50 g (1.6 mmol) of (R)-3-(5-methylpyridin-2-ylamino)-2-(oxirane-2-ylmethoxy)benzoic acid methyl ester obtained in (34-5) was dissolved in 5 mL of dimethylformamide. 0.28 g (2.0 mmol) of K$_2$CO$_3$ was added thereto and stirred at 100° C. for 5 hr. The reaction mixture was cooled to room temperature and concentrated under reduced pressure, then diluted with ethyl acetate and washed with distilled water and saturated sodium chloride solution, followed by drying over magnesium sulfate and concentration under reduced temperature. The resulting residue was subjected to column chromatography (ethyl acetate/hexane=1/1) to obtain the title compound (0.50 g, yield: 91%).

$^1$H NMR (CDCl$_3$) δ: 8.15(d, 1H, J=2.0 Hz), 7.45(dd, 1H, J=8.4, 2.2 Hz), 7.37-7.24(m, 3H), 6.81(t, 1H, J=8.0 Hz), 4.49(dd, 1H, J=11.1, 1.5 Hz), 4.43-4.37(m, 1H), 4.27(dd, 1H, J=11.1, 1.5 Hz), 3.89(s, 3H), 3.85-3.79(m, 2H), 2.30(s, 3H)

(34-7) Preparation of (S)-3(hydroxymethyl)-4-(5-methylpyridin-2-yl)-3,4-dihydro-2H-benzo[b][1,4] oxazin-8-carboxylic acid (compound 23)

3.5 g (11 mmol) of (S)-3-(hydroxymethyl)-4-(5-methylpyridin-2-yl)-3,4-dihydro-2H-benzo[b][1,4]oxazin-8-carboxylic acid methyl ester obtained in (34-6) was dissolved in 40 mL of methanol, 10 mL of 4N sodium hydroxide solution was added dropwise thereto, stirred at 60° C. for 3 hr and cooled to room temperature. The reaction mixture was neutralized with 40 mL of 1N hydrochloric acid and the resulting solids were filtered. The filtered material was washed with distilled water and dried under vacuum to obtain the title compound (2.9 g, yield: 87%).

$^1$H NMR (CDCl$_3$) δ: 8.18(d, 1H, J=2.0 Hz), 7.70(dd, 1H, J=7.9, 1.5 Hz), 7.50(dd, 1H, J=8.4, 2.3 Hz), 7.39(dd, 1H, J=8.2, 1.3 Hz), 7.27(d, 1H, J=8.8 Hz), 6.93(t, 1H, J=8.0 Hz), 4.66(dd, 1H, J=10.8, 1.4 Hz), 4.51-4.45(m, 1H), 4.40(dd, 1H, 10.8, 3.1 Hz), 3.87-3.79(m, 2H), 2.31(s, 3H)

(34-8) Preparation of [(S)-8-(6-tert-butyl-1H-benzimidazol-2-yl)-4-(5-methylpyridin-2-yl)-3,4-dihydro-2H-benzo[1,4]oxazin-3-yl]-methanol (compound 1e)

3.0 g (10 mmol) of (S)-3-(hydroxymethyl)-4-(5-methylpyridin-2-yl)-3,4-dihydro-2H-benzo[b][1,4]oxazin-8-carboxylic acid obtained in (34-7) was dissolved in 50 mL of dimethylformamide. 1.8 g (11 mmol) of 4-tert-butylbenzene-1,2-diamine, 3.5 mL (20 mmol) of diisopropylethylamine and 5.7 g (15 mmol) of O-(7-azabenzotriazole-1-yl)-N,N,N',N'-tetramethyluronium hexafluorophosphate were added thereto and stirred at a room temperature for 3 hr. The reaction mixture was diluted with ethyl acetate and washed with saturated sodium bicarbonate solution and saturated sodium chloride solution, followed by drying over magnesium sulfate and concentration under reduced pressure. The resulting residue was dissolved in acetate/toluene (90 mL/10 mL) and stirred at 75° C. for 4 hr, followed by cooling to room temperature and concentration under reduced pressure. The concentrate was dissolved in ethyl acetate and washed with saturated sodium bicarbonate solution and saturated sodium chloride solution, followed by drying over magnesium sulfate and concentration under reduced pressure. The resulting residue was subjected to column chromatography (ethyl acetate/hexane=2/3) to obtain the title compound (3.9 g, yield: 92%).

$^1$H NMR (CDCl$_3$) δ: 8.17(s, 1H), 8.11(d, 1H, J=7.9 Hz), 7.68(s, 1H), 7.59(d, 1H, J=8.5 Hz), 7.49(dd, 1H, J=8.4, 2.3 Hz), 7.38-7.33(m, 2H), 7.26(m, 1H), 6.96(t, 1H, J=8.0 Hz), 4.69(dd, 1H, J=10.8, 1.4 Hz), 4.52-4.48(m, 1H), 4.33(dd, 1H, J=10.8, 3.0 Hz), 3.97-3.83(m, 2H), 2.31(s, 3H), 1.40(s, 9H)

EXAMPLE 35

Preparation of [(S)-4-(5-methyl-pyridin-2-yl)-8-(6-trifluoromethyl-1H-benzimidazol-2-yl)-3,4-dihydro-2H-benzo[1,4]oxazin-3-yl]-methanol (compound 1e)

The procedure of Example 34 was repeated except for using 4-(trifluoromethyl)benzene-1,2-diamine instead of 4-tert-butylbenzene-1,2-diamine in (34-8) to obtain the title compound (4.0 g, yield: 90%).
$^1$H NMR (CDCl$_3$) δ: 8.19(d, 1H, J=2.1 Hz), 8.13(dd, 1H, J=7.9, 1.5 Hz), 7.97(s, 1H), 7.73(s, 1H), 7.54-7.48(m, 2H), 7.36-7.28(m, 2H), 7.00(t, 1H, J=8.0 Hz), 4.72(dd, 1H, J=10.8, 1.4 Hz), 4.54-4.49(m, 1H), 4.45(dd, 1H, J=10.7, 3.1 Hz), 3.99-3.85(m, 2H), 2.32(s, 3H)

EXAMPLE 36

Preparation of [(S)-8-(6-bromo-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-bromobenzene-1,2-diamine instead of 4-tert-butylbenzene-1,2-diamine in (34-8) to obtain the title compound (4.0 g, yield: 88%).
$^1$H NMR (CDCl$_3$) δ: 8.18(s, 1H), 8.09(dd, 1H, J=7.9, 1.5 Hz), 7.80(s, 1H), 7.54-7.47(m, 2H), 7.39-7.26(m, 3H), 6.97(t, 1H, J=8.0 Hz), 4.70(dd, 1H, J=10.8, 1.4 Hz), 4.54-4.48(m, 1H), 4.43(dd, 1H, J=10.8, 3.1 Hz), 3.97-3.83(m, 2H), 2.32(s, 3H)

EXAMPLE 37

Preparation of [(S)-8-(6-chloro-1,1-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-chlorobenzene-1,2-diamine instead of 4-tert-butylbenzene-1,2-diamine in (34-8) to obtain the title compound (3.8 g, yield: 94%).
$^1$H NMR (CDCl$_3$) δ: 8.17(d, 1H, J=2.0 Hz), 8.07(dd, 1H, J=7.9, 1.5 Hz), 7.63(d, 1H, J=1.7 Hz), 7.55(d, 1H, J=8.6 Hz), 7.48(dd, 1H, J=8.4, 2.3 Hz), 7.33(d, 1H, J=8.4 Hz), 7.28-7.20(m, 2H), 6.95(t, 1H, J=8.0 Hz), 4.68(dd, 1H, J=10.8, 1.4 Hz), 4.54-4.46(m, 1H), 4.41(dd, 1H, J=10.8, 3.1 Hz), 3.96-3.81(m, 2H), 2.31(s, 3H)

EXAMPLE 38

Preparation of [(S)-8-(5,6-dichloro-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4,5-dichlorobenzene-1,2-diamine instead of 4-tert-butylbenzene-1,2-diamine in (34-8) to obtain the title compound (4.1 g, yield: 93%).
$^1$H NMR (CDCl$_3$) δ: 8.18(d, 1H, J=2.0 Hz), 8.07(dd, 1H, J=7.9, 1.5 Hz), 7.74(s, 1H), 7.49(dd, 1H, J=8.4, 2.3 Hz), 7.34(d, 1H, J=8.3 Hz), 7.29(dd, 1H, J=8.3, 1.6 Hz), 6.98(t, 1H, J=8.0 Hz), 4.71(dd, 1H, J=10.8, 1.4 Hz), 4.55-4.48(m, 1H), 4.44(dd, 1H, J=10.7, 3.1 Hz), 3.97-3.84(m, 2H), 2.32(s, 3H)

EXAMPLE 39

Preparation of [(S)-8-(4-chloro-6-trifluoromethyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 3-chloro-5-trifluoromethylbenzene-1,2-diamine instead of 4-tert-butylbenzene-1,2-diamine in (34-8) to obtain the title compound (4.3 g, yield: 91%).
$^1$H NMR (CDCl$_3$) δ: 9.44(s, 1H), 8.18(s, 1H), 7.80(dd, 1H, J=7.9, 1.5 Hz), 7.56(s, 1H), 7.52-7.47(m, 2H), 7.38-7.27(m, 2H), 6.96(t, 1H, J=8.0 Hz), 4.64(dd, 1H, J=10.8, 1.4 Hz), 4.51-4.46(m, 1H), 4.42(dd, 1H, J=10.7, 3.1 Hz), 3.94-3.81(m, 2H), 2.32(s, 3H)

EXAMPLE 40

Preparation of [(S)-8-(4,6-bis-trifluoromethyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 3,5-bis-trifluoromethylbenzene-1,2-diamine instead of 4-tert-butylbenzene-1,2-diamine in (34-8) to obtain the title compound (4.5 g, yield: 89%).
$^1$H NMR (CDCl$_3$) δ: 9.29(s, 1H), 8.19(s, 1H), 7.84(s, 1H), 7.80(dd, 1H, J=7.9, 1.6 Hz), 7.74(s, 1H), 7.50(dd, 1H, J=8.4, 2.3 Hz), 7.40-7.28(m, 2H), 6.98(t, 1H, J=8.0 Hz), 4.65(dd, 1H, J=10.8, 1.4 Hz), 4.54-4.47(m, 1H), 4.43(dd, 1H, J=10.7, 3.1 Hz), 3.96-3.83(m, 2H), 2.33(s, 3H)

EXAMPLE 41

Preparation of [(S)-8-(4-bromo-6-trifluoromethyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 3-bromo-5-trifluoromethylbenzene-1,2-diamine instead of 4-tert-butylbenzene-1,2-diamine in (34-8) to obtain the title compound (4.7 g, yield: 90%).
$^1$H NMR (CDCl$_3$) δ: 9.43(s, 1H), 8.17(s, 1H), 7.79(dd, 1H, J=7.9, 1.5 Hz), 7.62(s, 2H), 7.49(dd, 1H, J=8.4, 2.3 Hz), 7.36(dd, 1H, J=8.1, 1.5 Hz), 7.28(d, 1H, J=8.6 Hz), 6.95(t, 1H, J=8.0 Hz), 4.64(dd, 1H, J=10.8, 1.4 Hz), 4.51-4.46(m, 1H), 4.41(dd, 1H, J=10.7, 3.1 Hz), 3.94-3.81(m, 2H), 2.31(s, 3H)

EXAMPLE 42

Preparation of [(S)-8-(4,6-dibromo-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 3,5-dibromobenzene-1,2-diamine instead of 4-tert-butylbenzene-1,2-diamine in (34-8) to obtain the title compound (4.7 g, yield: 89%).
$^1$H NMR (CDCl$_3$) δ: 8.18(d, 1H, J=2.0 Hz), 7.56(s, 1H), 7.49(dd, 1H, J=8.4, 2.0 Hz), 7.34(d, 1H, J=8.4 Hz), 7.30(dd, 1H, J=8.1, 1.6 Hz), 6.98(t, 1H, J=8.0 Hz), 4.71(dd, 1H, J=10.8, 1.4 Hz), 4.56-4.44(m, 2H), 3.97-3.85(m, 2H), 2.32(s, 3H)

EXAMPLE 43

Preparation of [(S)-8-(6-bromo-4-fluoro-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 5-bromo-3-fluorobenzene-1,2-diamine instead of 4-tert-butylbenzene-1,2-diamine in (34-8) to obtain the title compound (3.9 g, yield: 83%).

$^1$H NMR (CDCl$_3$) δ: 8.17(s, 1H), 8.11(d, 1H, J=8.4 Hz), 7.49(dd, 1H, J=8.4, 2.0 Hz), 7.35-7.26(m, 2H), 7.14(dd, 1H, J=9.8, 1.5 Hz), 6.97(t, 1H, J=8.0 Hz), 4.71(dd, 1H, J=10.8, 1.4 Hz), 4.56-4.48(m, 1H), 4.43(dd, 1H, J=10.7, 3.1 Hz), 3.96-3.80(m, 2H), 2.32(s, 3H)

EXAMPLE 44

Preparation of [(S)-8-(5,6-difluoro-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4,5-difluorobenzene-1,2-diamine instead of 4-tert-butylbenzene-1,2-diamine in (34-8) to obtain the title compound (3.9 g, yield: 95%).

$^1$H NMR (CD$_3$OD) δ: 8.17(s, 1H), 7.79(dd, 1H, J=7.8, 1.5 Hz), 7.58(dd, 1H, J=8.4, 2.3 Hz), 7.49(dd, 2H, J=10.4, 7.3 Hz), 7.30(d, 2H, J=8.3 Hz), 6.99(t, 1H, J=8.0 Hz), 4.85(d, 1H, J=10.7 Hz), 4.50(m, 1H), 4.25(dd, 1H, J=11.0, 2.7 Hz), 3.86 (d, 1H, J=10.9, 6.9 Hz), 3.67(dd, 1H, J=10.9, 8.1 Hz), 2.31(s, 3H)

EXAMPLE 45

Preparation of [(S)-8-(6-chloro-5-fluoro-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-chloro-5-fluorobenzene-1,2-diamine instead of 4-tert-butylbenzene-1,2-diamine in (34-8) to obtain the title compound (3.7 g, yield: 88%).

$^1$H NMR (CD$_3$OD) δ: 8.16(s, 1H), 7.80(dd, 1H, J=7.8, 1.4 Hz), 7.71(d, 1H, J=6.7 Hz), 7.58(dd, 1H, J=8.4, 2.4 Hz), 7.47(d, 1H, J=9.4 Hz), 7.30(m, 2H), 6.99(t, 1H, J=8.0 Hz), 4.85(dd, 1H, J=11.5, 2.0 Hz), 4.50(m, 1H), 4.25(dd, 1H, J=11.0, 2.7 Hz), 3.86(d, 1H, J=10.8, 6.9 Hz), 3.67(dd, 1H, J=10.9, 8.1 Hz), 2.30(s, 3H)

EXAMPLE 46

Preparation of [(S)-8-(6-bromo-4-methyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 5-bromo-3-methylbenzene-1,2-diamine instead of 4-tert-butylbenzene-1,2-diamine in (34-8) to obtain the title compound (3.9 g, yield: 84%).

$^1$H NMR (CD$_3$OD) δ: 8.16(s, 1H), 7.83(s, 1H), 7.58(m, 2H), 7.30(dd, 2H, J=8.1, 1.8 Hz), 7.19(s, 1H), 6.99(t, 1H, J=4.3 Hz), 4.80(m, 1H), 4.49(m, 1H), 4.23(dd, 1H, J=11.0, 2.6 Hz), 3.87(dd, 1H, J=10.8, 6.9 Hz), 3.67(dd, 1H, J=10.9, 8.2 Hz), 2.63(s, 3H), 2.31(s, 3H)

EXAMPLE 47

Preparation of [(S)-4-(5-methyl-pyridin-2-yl)-8-(6-trifluoromethoxy-1H-benzimidazol-2-yl)-3,4-dihydro-2H-benzo[1,4]oxazin-3-yl]-methanol (compound 1e)

The procedure of Example 34 was repeated except for using 4-(trifluoromethoxy)benzene-1,2-diamine instead of 4-tert-butylbenzene-1,2-diamine in (34-8) to obtain the title compound (4.3 g, yield: 94%).

$^1$H NMR (CD$_3$OD) δ: 8.16(d, 1H, J=2.3 Hz), 7.81(dd, 1H, J=7.8, 1.5 Hz), 7.70(d, 1H, J=8.8 Hz), 7.58(m, 2H), 7.32(dd, 1H, J=8.1, 1.5 Hz), 7.30(d, 1H, J=2.4 Hz), 7.20(dd, 1H, J=8.8, 1.4 Hz), 7.0(t, 1H, J=7.3 Hz), 4.85(dd, 1H, J=11.1, 1.4 Hz), 4.50(m, 1H), 4.26(dd, 1H, J=11.0, 2.7 Hz), 3.87(dd, 1H, J=10.9, 7.0 Hz), 3.86(s, 3H), 3.67(dd, 1H, J=10.9, 8.1 Hz), 2.30(s, 3H)

EXAMPLE 48

Preparation of [(S)-8-(6-methoxy-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-methoxybenzene-1,2-diamine instead of 4-tert-butylbenzene-1,2-diamine in (34-8) to obtain the title compound (3.7 g, yield: 92%).

$^1$H NMR (CD$_3$OD) δ: 8.16(d, 1H, J=2.3 Hz), 7.81(dd, 1H, J=7.8, 1.5 Hz), 7.70(d, 1H, J=8.8 Hz), 7.58(m, 2H), 7.32(dd, 1H, J=8.1, 1.5 Hz), 7.30(d, 1H, J=2.4 Hz), 7.20(dd, 1H, J=8.8, 1.4 Hz), 7.0(t, 1H, J=7.3 Hz), 4.85(dd, 1H, J=11.1, 1.4 Hz), 4.50(m, 1H), 4.26(dd, 1H, J=11.0, 2.7 Hz), 3.87(dd, 1H, J=10.9, 7.0 Hz), 3.67(dd, 1H, J=10.9, 8.1 Hz), 2.30(s, 3H)

EXAMPLE 49

Preparation of [(S)-8-(6-fluoro-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-fluorobenzene-1,2-diamine instead of 4-tert-butylbenzene-1,2-diamine in (34-8) to obtain the title compound (3.5 g, yield: 90%).

$^1$H NMR (CD$_3$OD) δ: 8.16(d, 1H, J=2.2 Hz), 7.79(dd, 1H, J=7.8, 1.5 Hz), 7.61(dd, 1H, J=8.8, 4.7 Hz), 7.58(dd, 1H, 8.2, 2.0 Hz), 7.34(dd, 1H, J=9.3, 2.6 Hz), 7.30(dd, 2H, J=8.2, 1.6 Hz), 7.06(dt, 1H, J=9.3, 2.2 Hz), 6.99(t, 1H, J=4.3 Hz), 4.84 (dd, 1H, J=11.0, 1.4 Hz), 4.50(m, 1H), 4.25(dd, 1H, J=11.0, 2.7 Hz), 3.86(dd, 1H, J=10.9, 6.9 Hz), 3.67(dd, 1H, J=10.9, 8.2 Hz), 2.30(s, 3H)

EXAMPLE 50

Preparation of [(S)-8-(4-methyl-1H-benzimidazol-2-yl)-4-(5-methyl-pyridine-2-yl)-3,4-dihydro-2H-benzo[1,4]oxazin-3-yl]-methanol (compound 1e)

The procedure of Example 34 was repeated except for using 3-methylbenzene-1,2-diamine instead of 4-tert-butylbenzene-1,2-diamine in (34-8) to obtain the title compound (3.4 g, yield: 87%).

¹H NMR (CD₃OD) δ: 8.17(d, 1H, J=2.2 Hz), 7.75(dd, 1H, J=7.8, 1.5 Hz), 7.59(dd, 1H, J=8.5, 2.4 Hz), 7.48(d, 1H, 8.0 Hz), 7.32(dd, 1H, J=8.2, 1.5 Hz), 7.31(d, 1H, J=8.5 Hz), 7.19(t, 1H, J=7.7 Hz), 7.10(d, 1H, J=7.32 Hz), 7.02(t, 1H, J=8.0 Hz), 4.81(dd, 1H, J=11.0, 1.3 Hz), 4.50(m, 1H), 4.24 (dd, 1H, J=11.0, 2.7 Hz), 3.88(dd, 1H, J=11.0, 6.9 Hz), 3.68 (dd, 1H, J=11.0, 8.2 Hz), 2.65(s, 3H), 2.30(s, 3H)

EXAMPLE 51

Preparation of [(S)-8-(5-methyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 4-methylbenzene-1,2-diamine instead of 4-tert-butylbenzene-1,2-diamine in (34-8) to obtain the title compound (3.5 g, yield: 91%).
¹H NMR (CD₃OD) δ: 8.16(d, 1H, J=2.1 Hz), 7.77(dd, 1H, J=9.9, 2.0 Hz), 7.57(dd, 1H, J=8.5, 2.3 Hz), 7.54(d, 1H, 8.3 Hz), 7.45(s, 1H), 7.29(d, 2H, J=8.3 Hz), 7.13(dd, 1H, J=8.3, 1.4 Hz), 6.99(t, 1H, J=8.0 Hz), 4.84(dd, 1H, J=11.0, 1.4 Hz), 4.51(m, 1H), 4.24(dd, 1H, J=11.0, 2.7 Hz), 3.86(dd, 1H, J=10.9, 6.9 Hz), 3.67(dd, 1H, J=10.9, 8.1 Hz), 2.49(s, 3H), 2.30(s, 3H)

EXAMPLE 52

Preparation of [(S)-8-(4,5-dimethyl-1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using 3,4-dimethylbenzene-1,2-diamine instead of 4-tert-butylbenzene-1,2-diamine in (34-8) to obtain the title compound (3.5 g, yield: 87%).
¹H NMR (CD₃OD) δ: 8.16(d, 1H, J=1.9 Hz), 7.73(dd, 1H, J=7.89, 1.5 Hz), 7.58(dd, 1H, J=8.4, 2.3 Hz), 7.37(d, 1H, 8.2 Hz), 7.31(m, 2H), 7.11(d, 1H, J=8.0 Hz), 7.00(t, 1H, J=8.0 Hz), 4.80(dd, 1H, J=11.0, 1.3 Hz), 4.50(m, 1H), 4.23(dd, 1H, J=11.0, 2.7 Hz), 3.88(dd, 1H, J=11.0, 6.9 Hz), 3.67(dd, 1H, J=11.0, 8.2 Hz), 2.57(s, 3H), 2.41(s, 3H), 2.31(s, 3H)

EXAMPLE 53

Preparation of [(S)-8-(1H-benzimidazol-2-yl)-4-(5-methyl-pyridin-2-yl)-3,4-dihydro-2H-benzo[1,4]oxazin-3-yl]-methanol (compound 1e)

The procedure of Example 34 was repeated except for using benzene-1,2-diamine instead of 4-tert-butylbenzene-1,2-diamine in (34-8) to obtain the title compound (3.5 g, yield: 93%).
¹H NMR (CD₃OD) δ: 8.15(d, 1H, J=2.2 Hz), 7.80(dd, 1H, J=7.8, 1.5 Hz), 7.65(dd, 2H, J=6.1, 3.1 Hz), 7.57(dd, 1H, J=8.4, 2.3 Hz), 7.28(m, 4H), 6.99(t, 1H, J=8.0 Hz), 4.84(dd, 1H, J=11.0, 1.4 Hz), 4.50(m, 1H), 4.24(dd, 1H, J=11.1, 2.9 Hz), 3.87(dd, 1H, J=10.9, 6.9 Hz), 3.67(dd, 1H, J=12.8, 10.1 Hz), 2.30(s, 3H)

EXAMPLE 54

Preparation of [(S)-8-(4-bromo-6-trifluoromethoxy-1H-benzimidazol-2-yl)-4-(5-methyl-pyridine-2-yl)-3,4-dihydro-2H-benzo[1,4]oxazin-3-yl]-methanol (compound 1e)

The procedure of Example 34 was repeated except for using 3-bromo-5-(trifluoromethoxy)benzene-1,2-diamine instead of 4-tert-butylbenzene-1,2-diamine in (34-8) to obtain the title compound (5.0 g, yield: 94%).
¹H NMR (CD₃OD) δ: 8.17(s, 1H), 7.92(d, 1H, J=7.6 Hz), 7.58(dd, 1H, J=11.9, 5.9 Hz), 7.55(s, 1H), 7.41(s, 1H), 7.23(t, 2H, J=9.1 Hz), 7.01(t, 1H, J=8.0 Hz), 4.85(d, 1H, J=10.7 Hz), 4.51(m, 1H), 4.26(dd, 1H, J=11.0, 2.7 Hz), 3.87(dd, 1H, J=10.8, 6.9 Hz), 3.68(dd, 1H, J=10.7, 8.3 Hz), 2.31(s, 3H)

EXAMPLE 55

Preparation of [(S)-8-(4,6-difluoro-1H-benzo[d]imidazol-2-yl)-4-(5-methyl-pyridin-2-yl)-3,4-dihydro-2H-benzo[b][1,4]oxazin-3-yl]-methanol The procedure of Example 34 was repeated except for using 3,5-difluorobenzene-1,2-diamine instead of 4-tert-butylbenzene-1,2-diamine in (34-8) to obtain the title compound (3.6 g, yield: 89%).
¹H NMR (CD₃OD) δ: 8.16(d, 1H, J=2.2 Hz), 7.81(d, 1H, J=7.1 Hz), 7.59(dd, 1H, J=8.4, 2.4 Hz), 7.32(m, 2H), 7.19(dd, 1H, J=8.6, 2.1 Hz), 6.99(t, 1H, J=8.0 Hz), 6.88(dt, 1H, J=10.5, 2.2 Hz), 4.85(d, 1H, J=10.7 Hz), 4.50(m, 1H), 4.25(dd, 1H, J=11.0, 2.7 Hz), 3.86(dd, 1H, J=10.9, 6.9 Hz), 3.67(dd, 1H, J=10.9, 8.1 Hz), 2.31(s, 3H)

EXAMPLE 56

Preparation of (S)-2-(3-(hydroxymethyl)-4-(5-methyl-pyridin-2-yl)-3,4-dihydro-2H-benzo[b][1,4]oxazin-8-yl)-1H-benzo[d]imidazol-6-carbonitrile The procedure of Example 34 was repeated except for using 3,4-diaminobenzonitrile instead of 4-tert-butylbenzene-1,2-diamine in (34-8) to obtain the title compound (3.7 g, yield: 93%).
¹H NMR (CD₃OD) δ: 8.16(d, 1H, J=2.2 Hz), 7.71(d, 1H, J=1.9 Hz), 7.58(dd, 1H, J=8.4, 2.2 Hz), 7.49(dd, 1H, J=7.8, 1.5 Hz), 7.34(m, 2H), 7.26(d, 1H, J=8.4 Hz), 6.94(m, 2H), 4.75(dd, 1H, J=10.9, 1.3 Hz), 4.53(m, 1H), 4.24(dd, 1H, J=11.0, 2.7 Hz), 3.85(dd, 1H, J=11.0, 6.7 Hz), 3.67(dd, 1H, J=11.2, 8.1 Hz), 2.30(s, 3H)

EXAMPLE 57

Preparation of [(S)-8-(6-tert-butyl-1H-benzimidazol-2-yl)-4-(5-vinyl-pyridin-2-yl)-3,4-dihydro-2H-benzo[1,4]oxazin-3-yl]-methanol (compound 1e)

(57-1) Preparation of methyl 3-amino-2-hydroxybenzoic acid (compound 11)

10 g (51 mmol) of 2-hydroxy-3-nitrobenzoic acid methyl ester was dissolved in 100 mL of methanol, 1.0 g of 5% Pd/C was added thereto, hydrogen gas was filled and stirred at room temperature for 24 hr. The reaction mixture was filtered through diatomite to remove the catalyst, followed by concentration under reduced pressure to obtain the title compound (8.4 g, yield: 99%).
¹H NMR (CDCl₃) δ: 7.29(d, 1H, J=7.7 Hz), 6.93(d, 1H, J=7.7 Hz), 6.71(t, 1H, J=7.9 Hz), 3.88(s, 3H)

(57-2) Preparation of 2-hydroxy-3-(5-vinylpyridin-2-ylamino)benzoic acid methyl ester (compound 19)

8.4 g (50 mmol) of 3-amino-2-hydroxybenzoic acid methyl ester obtained in (57-1) was dissolved in 250 mL of 1,4-dioxane. 7.0 g (50 mmol) of 2-chloro-5-vinylpyridine, 1.1 g (5 mmol) of Pd(OAc)$_2$, 3.1 g (5 mmol) of 2,2'-bis (diphenylphosphino)-1,1'-binaphtyl and 32.7 g (100 mmol) of Cs$_2$CO$_3$ were added thereto and stirred at 90° C. for 12 hr. The reaction mixture was cooled to room temperature and concentrated under reduced temperature, followed by dilution with ethyl acetate and washing with saturated sodium bicarbonate solution and saturated sodium chloride solution. The washed material was dried over magnesium sulfate, concentrated under reduced pressure, and subjected to column chromatography (ethyl acetate/hexane=1/4) to obtain the title compound (10.9 g, yield: 80%).

$^1$H NMR (CDCl$_3$) δ: 8.54(d, 1H, J=7.9 Hz), 8.24(s, 1H), 7.66(d, 1H, J=8.5 Hz), 7.44(d, 1H, J=7.9 Hz), 7.12(s, 1H), 6.91(t, 1H, J=8.0 Hz), 6.77(d, 1H, J=8.0 Hz), 6.64(dd, 1H, J=17.6, 11.0 Hz), 5.63(d, 1H, J=17.6 Hz), 5.18(d, 1H, J=11.0 Hz), 3.97(s, 3H)

(57-3) Preparation of (S)-3-(hydroxymethyl)-4-(5-vinylpyridin-2-yl)-3,4-dihydro-2H-benzo[b][1,4]oxazin-8-carboxylic acid methyl ester (compound 22)

8.0 g (29.6 mmol) of 2-hydroxy-3-(5-vinylpyridin-2-ylamino)benzoic acid methyl ester obtained in (57-2) was dissolved in 98 mL of dimethylformamide. 8.4 g (32.6 mmol) of (R)-glycidyl nosylate and 8.2 g (59.2 mmol) of K$_2$CO$_3$ were added thereto and stirred at room temperature for 12 hr. 4.1 g (29.6 mmol) of K$_2$CO$_3$ was added thereto and stirred at 100° C. for 5 hr. The reaction mixture was cooled to room temperature and concentrated under reduced pressure, followed by dilution with ethyl acetate and washing with distilled water and saturated sodium hydrochloride. The washed material was dried over magnesium sulfate, concentrated under reduced pressure and subjected to column chromatography (ethyl acetate/hexane=1/1) to obtain the title compound (8.6 g, yield: 89%).

$^1$H NMR (CDCl$_3$) δ: 8.29(d, 1H, J=2.3 Hz), 7.71(dd, 1H, J=8.6, 2.4 Hz), 7.40-7.38(m, 2H), 7.32(d, 1H, J=8.6 Hz), 6.84(t, 1H, J=8.0 Hz), 6.65(dd, 1H, J=17.6, 11.0 Hz), 5.71(d, 1H, J=17.6 Hz), 5.30(d, 1H, J=11 Hz), 5.06(br, 1H), 4.51(dd, 2H, J=11.3, 1.2 Hz), 4.28(dd, 1H, J=11.3, 3.4 Hz), 3.89(s, 3H), 3.83(d, 2H, J=8.1 Hz)

(57-4) Preparation of (S)-3-(hydroxymethyl)-4-(5-vinylpyridin-2-yl)-3,4-dihydro-2H-benzo[b][1,4]oxazin-8-carboxylic acid (compound 23)

7.0 g (21.4 mmol) of (S)-3-(hydroxymethyl)-4-(5-vinylpyridin-2-yl)-3,4-dihydro-2H-benzo[b][1,4]oxazin-8-carboxylic acid methyl ester obtained in (57-3) was dissolved in 70 mL of methanol 8.0 mL of 4N sodium hydroxide solution was added dropwise thereto, stirred at 60° C. for 3 hr and cooled to room temperature. The reaction mixture was neutralized with 32 mL of 1N hydrochloric acid and the resulting solids were filtered. The filtered material was washed with distilled water and dried under vacuum to obtain the title compound (5.9 g, yield: 88%).

$^1$H NMR (CD$_3$OD) δ: 8.28(d, 1H, J=2.2 Hz), 7.89(dd, 1H, J=8.8, 2.3 Hz), 7.45(m, 2H), 7.34(d, 1H, J=8.8 Hz), 6.91(t, 1H, J=7.9 Hz), 6.72(dd, 1H, J=17.7, 11.0 Hz), 5.79(d, 1H, J=17.6 Hz), 5.28(d, 1H, J=11.0 Hz), 4.65(dd, 1H, J=8.1, 4.1 Hz), 4.57(m, 1H), 4.15(dd, 1H, J=11.1, 2.8 Hz), 3.78(dd, 1H, J=11.0, 7.1 Hz), 3.64(dd, 1H, J=11.0, 7.9 Hz)

(57-5) Preparation of [(S)-8-(6-tert-butyl-1H-benzimidazol-2-yl)-4-(5-vinyl-pyridin-2-yl)-3,4-dihydro-2H-benzo[1,4]oxazin-3-yl]-methanol (compound 1e)

5.0 g (16.0 mmol) of (S)-3-(hydroxymethyl)-4-(5-vinylpyridin-2-yl)-3,4-dihydro-2H-benzo[b][1,4]oxazin-8-carboxylic acid obtained in (57-4) was dissolved in 20 mL of dimethylformamide. 26.3 g (16.0 mmol) of 4-tert-butylbenzene-1,2-diamine, 4.6 mL (32.0 mmol) of diisopropylethylamine and 7.3 g (19.2 mmol) of O-(7-azabenzotriazole-1-yl))-N,N,N',N'-tetramethyluronium hexafluorophosphate were added thereto and stirred at room temperature for 4 hr. The reaction mixture was diluted with ethyl acetate and washed with saturated sodium bicarbonate solution and saturated sodium hydrochloride, followed by drying over magnesium sulfate and concentration under reduced pressure. The resulting residue was dissolved in 240 mL of acetic acid and stirred at 75° C. for 4 hr, followed by cooling to room temperature and concentration at reduced pressure. The concentrate was dissolved in ethyl acetate, washed with saturated sodium bicarbonate solution and saturated sodium chloride solution, dried over magnesium sulfate and concentrated under reduced pressure. The resulting residue was subjected to column chromatography (ethyl acetate/hexane=2/3) to obtain the title compound (6.3 g, yield: 89%).

$^1$H NMR (CDCl$_3$) δ: 8.31(d, 1H, J=2.3 Hz), 7.87(m, 2H), 7.64(m, 2H), 7.43(dd, 1H, J=8.2, 1.4 Hz), 7.37(d, 1H, J=8.7 Hz), 7.26(d, 1H, J=8.6 Hz), 7.03(t, 1H, J=8.0 Hz), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz), 1.40(s, 9H)

EXAMPLE 58

Preparation of [(S)-8-(6-trifluoromethyl-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-(trifluoromethyl)benzene-1,2-diamine instead of 4-tert-butylbenzene-1,2-diamine in (57-5) to obtain the title compound (4.0 g, yield: 89%).

$^1$H NMR (CD$_3$OD) δ: 8.31(d, 1H, J=2.3 Hz), 7.87(m, 2H), 7.64(m, 2H), 7.43(dd, 1H, J=8.2, 1.4 Hz), 7.37(d, 1H, J=8.7 Hz), 7.26(d, 1H, J=8.6 Hz), 7.03(t, 1H, J=8.0 Hz), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 59

Preparation of [(S)-8-(6-chloro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-chlorobenzene-1,2-diamine instead of 4-tert-butylbenzene-1,2-diamine in (57-5) to obtain the title compound (3.8 g, yield: 91%).

$^1$H NMR (CD$_3$OD) δ: 8.31(d, 1H, J=2.3 Hz), 7.87(m, 2H), 7.64(m, 2H), 7.43(dd, 1H, J=8.2, 1.4 Hz), 7.37(d, 1H, J=8.7 Hz), 7.26(d, 1H, J=8.6 Hz), 7.03(t, 1H, J=8.0 Hz), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 60

Preparation of [(S)-8-(6-bromo-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-bromobenzene-1,2-diamine instead of 4-tert-butylbenzene-1,2-diamine in (57-5) to obtain the title compound (4.3 g, yield: 92%).

$^1$H NMR (CD$_3$OD) δ: 8.31(d, 1H, J=2.3 Hz), 7.87(m, 2H), 7.80(s, 1H), 7.53(m, 1H), 7.40(m, 3H), 7.03(t, 1H, J=8.0 Hz), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 61

Preparation of [(S)-8-(6-fluoro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-fluorobenzene-1,2-diamine instead of 4-tert-butylbenzene-1,2-diamine in (57-5) to obtain the title compound (3.5 g, yield: 88%).

$^1$H NMR (CD$_3$OD) δ: 8.31(d, 1H, J=2.3 Hz), 7.87(m, 2H), 7.61(m, 1H), 7.42(dd, 1H, J=8.2, 1.5 Hz), 7.37(d, 1H, J=8.8 Hz), 7.31(m, 1H), 7.04(m, 2H), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 62

Preparation of [(S)-8-(6-bromo-4-fluoro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 5-bromo-3-fluorobenzene-1,2-diamine instead of 4-tert-butylbenzene-1,2-diamine in (57-5) to obtain the title compound (4.5 g, yield: 94%).

$^1$H NMR (CD$_3$OD) δ: 8.32(d, 1H, J=2.3 Hz), 7.87(m, 2H), 7.63(s, 1H), 7.45(dd, 1H, J=8.1, 1.5 Hz), 7.37(d, 1H, J=8.7 Hz), 7.19(m, 1H), 7.03(t, 1H, J=8.0 Hz), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 63

Preparation of [(S)-8-(4,6-difluoro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 3,5-difluorobenzene-1,2-diamine instead of 4-tert-butylbenzene-1,2-diamine in (57-5) to obtain the title compound (3.8 g, yield: 91%).

$^1$H NMR (CD$_3$OD) δ: 8.31(d, 1H, J=2.3 Hz), 7.87(m, 2H), 7.47(dd, 1H, J=8.1, 1.4 Hz), 7.37(d, 1H, J=8.8 Hz), 7.19(m, 1H), 7.03(t, 1H, J=8.0 Hz), 6.88(m, 1H), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 64

Preparation of [(S)-8-(4-bromo-6-trifluoromethyl-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 3-bromo-5-trifluoromethylbenzene-1,2-diamine instead of 4-tert-butylbenzene-1,2-diamine in (57-5) to obtain the title compound (4.6 g, yield: 87%).

$^1$H NMR (CD$_3$OD) δ: 8.31(d, 1H, J=2.2 Hz), 7.87(m, 1H), 7.66(s, 1H), 7.55(dd, 1H, J=7.8, 1.6 Hz), 7.47(m, 2H), 7.33(d, 1H, J=8.6 Hz), 7.03(t, 1H, J=8.0 Hz), 6.73(dd, 1H, J=17.7, 11.0 Hz), 5.79(d, 1H, J=17.7 Hz), 5.27(d, 1H, J=11.0 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 65

Preparation of [(S)-8-(4-chloro-6-trifluoromethyl-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 3-chloro-5-trifluoromethylbenzene-1,2-diamine instead of 4-tert-butylbenzene-1,2-diamine in (57-5) to obtain the title compound (4.6 g, yield: 94%).

$^1$H NMR (CD$_3$OD) δ: 8.31(d, 1H, J=2.2 Hz), 7.87(m, 1H), 7.66(s, 1H), 7.55(dd, 1H, J=7.8, 1.6 Hz), 7.47(m, 2H), 7.33(d, 1H, J=8.6 Hz), 7.03(t, 1H, J=8.0 Hz), 6.73(dd, 1H, J=17.7, 11.0 Hz), 5.79(d, 1H, J=17.7 Hz), 5.27(d, 1H, J=11.0 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 66

Preparation of [(S)-8-(6-bromo-4-methyl-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 5-bromo-3-methylbenzene-1,2-diamine instead of 4-tert-butylbenzene-1,2-diamine in (57-5) to obtain the title compound (4.2 g, yield: 88%).

$^1$H NMR (CD$_3$OD) δ: 8.31(d, 1H, J=2.2 Hz), 7.87(m, 2H), 7.60(m, 1H), 7.43(dd, 1H, J=8.1, 1.3 Hz), 7.37(d, 1H, J=8.7 Hz), 7.20(s, 1H), 7.03(t, 1H, J=8.0 Hz), 6.73(dd, 1H, J=17.7, 11.0 Hz), 5.79(d, 1H, J=17.7 Hz), 5.27(d, 1H, J=11.0 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz), 2.64(s, 3H)

EXAMPLE 67

Preparation of [(S)-8-(6-trifluoromethoxy-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-(trifluoromethoxy)benzene-1,2-diamine instead of 4-tert-butylbenzene-1,2-diamine in (57-5) to obtain the title compound (4.5 g, yield: 96%).

¹H NMR (CD₃OD) δ: 8.32(d, 1H, J=2.2 Hz), 7.87(m, 2H), 7.70(m, 1H), 7.56(s, 1H), 7.44(dd, 1H, J=8.1, 1.5 Hz), 7.38(d, 1H, J=8.7 Hz), 7.20(d, 1H, J=8.9 Hz), 7.04(t, 1H, J=8.0 Hz), 6.73(dd, 1H, J=17.7, 11.0 Hz), 5.79(d, 1H, J=17.6 Hz), 5.27 (d, 1H, J=11.3 Hz), 4.90(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 68

Preparation of [(S)-8-(5,6-dichloro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4,5-dichlorobenzene-1,2-diamine instead of 4-tert-butylbenzene-1,2-diamine in (57-5) to obtain the title compound (4.1 g, yield: 91%).

¹H NMR (CD₃OD) δ: 8.31(d, 1H, J=2.3 Hz), 7.87(m, 2H), 7.79(s, 2H), 7.44(dd, 1H, J=8.1, 1.5 Hz), 7.37(d, 1H, J=8.7 Hz), 7.04(t, 1H, J=8.0 Hz), 6.73(dd, 1H, J=17.7, 11.0 Hz), 5.79(d, 1H, J=17.6 Hz), 5.27(d, 1H, J=11.0 Hz), 4.90(m, 1H), 4.69(m, 1H), 4.29(dd, 1H, J=11.0, 2.7 Hz), 3.87(dd, 1H, J=11.0, 6.8 Hz), 3.67(dd, 1H, J=10.9, 8.3 Hz)

EXAMPLE 69

Preparation of [(S)-8-(5,6-difluoro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4,5-difluorobenzene-1,2-diamine instead of 4-tert-butylbenzene-1,2-diamine in (57-5) to obtain the title compound (3.7 g, yield: 87%).

¹H NMR (CD₃OD) δ: 8.31(d, 1H, J=2.3 Hz), 7.87(m, 2H), 7.79(s, 2H), 7.44(dd, 1H, J=8.1, 1.5 Hz), 7.37(d, 1H, J=8.7 Hz), 7.04(t, 1H, J=8.0 Hz), 6.73(dd, 1H, J=17.7, 11.0 Hz), 5.79(d, 1H, J=17.6 Hz), 5.27(d, 1H, J=11.0 Hz), 4.90(m, 1H), 4.69(m, 1H), 4.29(dd, 1H, J=11.0, 2.7 Hz), 3.87(dd, 1H, J=11.0, 6.8 Hz), 3.67(dd, 1H, J=10.9, 8.3 Hz)

EXAMPLE 70

Preparation of [(S)-8-(6-chloro-5-fluoro-1H-benzimidazol-2-yl)-4-(5-vinyl-pyridin-2-yl)-3,4-dihydro-2H-benzo[1,4]oxazin-3-yl]-methanol (compound 1e)

The procedure of Example 57 was repeated except for using 4-chloro-5-fluorobenzene-1,2-diamine instead of 4-tert-butylbenzene-1,2-diamine in (57-5) to obtain the title compound (4.2 g, yield: 95%).

¹H NMR (CD₃OD) δ: 8.31(d, 1H, J=2.3 Hz), 7.87(m, 2H), 7.72(m, 1H), 7.48(d, 1H, J=9.3 Hz), 7.43(dd, 1H, J=8.2, 1.5 Hz), 7.37(d, 1H, J=8.7 Hz), 7.03(t, 1H, J=8.0 Hz), 6.73(dd, 1H, J=17.7, 11.0 Hz), 5.79(d, 1H, J=17.6 Hz), 5.27(d, 1H, J=11.0 Hz), 4.90(m, 1H), 4.69(m, 1H), 4.29(dd, 1H, J=11.0, 2.7 Hz), 3.87(dd, 1H, J=11.0, 6.8 Hz), 3.67(dd, 1H, J=10.9, 8.3 Hz)

EXAMPLE 71

Preparation of ((S)-8-(4,6-bis(trifluoromethyl)-1H-benzo[d]imidazol-2-yl)-4-(5-vinyl-pyridin-2-yl)-3,4-dihydro-2H-benzo[b][1,4]oxazin-3-yl]-methanol (compound 1e)

The procedure of Example 57 was repeated except for using 3,5-bis-trifluoromethylbenzene-1,2-diamine instead of 4-tert-butylbenzene-1,2-diamine in (57-5) to obtain the title compound (4.6 g, yield: 89%).

¹H NMR (CD₃OD) δ: 8.32(d, 1H, J=2.3 Hz), 7.86(m, 2H), 7.46(dd, 1H, J=8.1, 1.4 Hz), 7.39(d, 1H, J=8.8 Hz), 7.20(m, 1H), 7.01(t, 1H, J=8.0 Hz), 6.88(m, 1H), 6.73(dd, 1H, J=17.7, 11.0 Hz), 5.79(d, 1H, J=17.8 Hz), 5.27(d, 1H, J=10.9 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 72

Preparation of (S)-(8-(6-methoxy-1H-benzo[d]imidazol-2-yl)-4-(5-vinyl-pyridin-2-yl)-3,4-dihydro-2H-benzo[b][1,4]oxazin-3-yl)methanol (compound 1e)

The procedure of Example 57 was repeated except for using 4-methoxybenzene-1,2-diamine instead of 4-tert-butylbenzene-1,2-diamine in (57-5) to obtain the title compound (3.7 g, yield: 90%).

¹H NMR (CD₃OD) δ: 8.31(d, 1H, J=2.3 Hz), 7.85(dt, 2H, J=8.1, 1.8 Hz), 7.52(d, 1H, J=8.8), 7.38(m, 2H), 7.15(d, 1H, J=2.3 Hz), 7.01(t, 1H, J=8.0 Hz), 6.91(dd, 1H, J=8.8, 2.5 Hz), 6.72(dd, 1H, J=17.7, 11.1 Hz), 5.79(d, 1H, J=17.6 Hz), 5.27 (d, 1H, J=11.3 Hz), 4.90(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 73

Preparation of (S)-2-(3-(hydroxymethyl)-4-(5-vinyl-pyridin-2-yl)-3,4-dihydro-2H-benzo[b][1,4]oxazin-8-yl)-1H-benzo[d]imidazol-6-carbonitrile (compound 1e)

The procedure of Example 57 was repeated except for using 3,4-diaminobenzonitrile instead of 4-tert-butylbenzene-1,2-diamine in (57-5) to obtain the title compound (3.8 g, yield: 94%).

¹H NMR (CD₃OD) δ: 8.32(d, 1H, J=2.2 Hz), 8.04(s, 1H), 7.90(m, 2H), 7.83(m, 1H), 7.59(dd, 1H, J=8.4, 1.5 Hz), 7.47 (dd, 1H, J=8.2, 1.5 Hz), 7.38(d, 1H, J=8.7 Hz), 7.06(t, 1H, J=8.0 Hz), 6.73(dd, 1H, J=17.6, 11.2 Hz), 5.79(d, 1H, J=17.8 Hz), 5.27(d, 1H, J=10.9 Hz), 4.85(m, 1H), 4.69(m, 1H), 4.29 (dd, 1H, J=11.0, 2.8 Hz), 3.88(dd, 1H, J=11.0, 6.8 Hz), 3.68 (dd, 1H, J=10.9, 8.3 Hz)

EXAMPLE 74

Preparation of (S)-(8-(6-methyl-1H-benzo[d]imidazol-2-yl)-4-(5-vinyl-pyridin-2-yl)-3,4-dihydro-2H-benzo[b][1,4]oxazin-3-yl)methanol (compound 1e)

The procedure of Example 57 was repeated except for using 4-methylbenzene-1,2-diamine instead of 4-tert-butylbenzene-1,2-diamine in (57-5) to obtain the title compound (3.5 g, yield: 89%).

¹H NMR (CD₃OD) δ: 8.30(d, 1H, J=2.2 Hz), 7.85(dd, 1H, J=8.7, 2.4 Hz), 7.81(dd, 1H, J=7.8, 1.5 Hz), 7.46(d, 1H, J=8.0 Hz), 7.41(dd, 1H, J=8.2, 1.5 Hz), 7.36(d, 1H, J=8.7 Hz), 7.16(t, 1H, J=7.7 Hz), 7.06(d, 1H, J=7.0 Hz), 7.02(t, 1H, J=8.0 Hz), 6.72(dd, 1H, J=17.7, 11.0 Hz), 5.78(d, 1H, J=17.6 Hz), 5.27(d, 1H, J=11.2 Hz), 4.85(m, 1H), 4.69(m, 1H), 4.29

(dd, 1H, J=11.0, 2.8 Hz), 3.88(dd, 1H, J=11.0, 6.8 Hz), 3.68 (dd, 1H, J=10.9, 8.3 Hz), 2.65(s, 3H)

EXAMPLE 75

Preparation of (S)-(8-(1H-benzo[d]imidazol-2-yl)-4-(5-vinyl-pyridin-2-yl)-3,4-dihydro-2H-benzo[b][1,4]oxazin-3-yl)methanol (compound 1e)

The procedure of Example 57 was repeated except for using benzene-1,2-diamine instead of 4-tert-butylbenzene-1,2-diamine in (57-5) to obtain the title compound (3.4 g, yield: 88%).

$^1$H NMR (CD$_3$OD) δ: 8.31(d, 1H, J=2.1 Hz), 7.86(dd, 2H, J=9.3, 1.7 Hz), 7.65(m, 2H), 7.39(m, 2H), 7.27(m, 2H), 7.03 (t, 1H, J=8.0 Hz), 6.73(dd, 1H, J=17.7, 11.0 Hz), 5.78(d, 1H, J=17.6 Hz), 5.27(d, 1H, J=11.2 Hz), 4.85(m, 1H), 4.69(m, 1H), 4.29(dd, 1H, J=11.0, 2.8 Hz), 3.88(dd, 1H, J=11.0, 6.8 Hz), 3.68(dd, 1H, J=10.9, 8.3 Hz)

EXAMPLE 76

Preparation of (S)-(8-(4-methyl-1H-benzo[d]imidazol-2-yl)-4-(5-vinyl-pyridin-2-yl)-3,4-dihydro-2H-benzo[b][1,4]oxazin-3-yl)methanol (compound 1e)

The procedure of Example 57 was repeated except for using 3-methylbenzene-1,2-diamine instead of 4-tert-butyl-benzene-1,2-diamine in (57-5) to obtain the title compound (3.5 g, yield: 87%).

$^1$H NMR (CD$_3$OD) δ: 8.30(d, 1H, J=2.2 Hz), 7.85(dd, 1H, J=8.7, 2.4 Hz), 7.81(dd, 1H, J=7.8, 1.5 Hz), 7.46(d, 1H, J=8.0 Hz), 7.41(dd, 1H, J=8.2, 1.5 Hz), 7.36(d, 1H, J=8.7 Hz), 7.16(t, 1H, J=7.7 Hz), 7.06(d, 1H, J=7.0 Hz), 7.02(t, 1H, J=8.0 Hz), 6.72(dd, 1H, J=17.7, 11.0 Hz), 5.78(d, 1H, J=17.6 Hz), 5.27(d, 1H, J=11.2 Hz), 4.85(m, 1H), 4.69(m, 1H), 4.29 (dd, 1H, J=11.0, 2.8 Hz), 3.88(dd, 1H, J=11.0, 6.8 Hz), 3.68 (dd, 1H, J=10.9, 8.3 Hz), 2.65(s, 3H)

EXAMPLE 77

Preparation of (S)-(8-(4,5-dimethyl-1H-benzo[d]imidazol-2-yl)-4-(5-vinyl-pyridin-2-yl)-3,4-dihydro-2H-benzo[b][1,4]oxazin-3-yl)methanol (compound 1e)

The procedure of Example 57 was repeated except for using 3,4-dimethylbenzene-1,2-diamine instead of 4-tert-butylbenzene-1,2-diamine in (57-5) to obtain the title compound (3.5 g, yield: 85%).

$^1$H NMR (CD$_3$OD) δ: 8.30(d, 1H, J=2.3 Hz), 7.85(dd, 1H, J=8.7, 2.4 Hz), 7.78(dd, 1H, J=7.8, 1.5 Hz), 7.40(dd, 1H, J=8.2, 1.5 Hz), 7.36(d, 1H, J=8.7 Hz), 7.09(d, 1H, J=8.3 Hz), 7.02(t, 1H, J=8.0 Hz), 6.72(dd, 1H, J=17.7, 11.0 Hz), 5.78(d, 1H, J=17.6 Hz), 5.27(d, 1H, J=11.2 Hz), 4.85(m, 1H), 4.69 (m, 1H), 4.29(dd, 1H, J=11.0, 2.8 Hz), 3.88(dd, 1H, J=11.0, 6.8 Hz), 3.68(dd, 1H, J=10.9, 8.3 Hz), 2.56(s, 3H), 2.41(s, 3H)

EXAMPLE 78

Preparation of [(S)-8-(6-tert-butyl-1H-benzimidazol-2-yl)-4-(5-ethyl-pyridin-2-yl)-3,4-dihydro-2H-benzo[1,4]oxazin-3-yl]-methanol (compound 1e)

(78-1) Preparation of methyl 3-amino-2-hydroxybenzoic acid (compound 11)

10 g (51 mmol) of 2-hydroxy-3-nitrobenzoic acid methyl ester was dissolved in 100 mL of methanol, 1.0 g of 5% Pd/C was added thereto, hydrogen gas was filled and stirred at room temperature for 24 hr. The reaction mixture was filtered through diatomite to remove the catalyst, followed by concentration under reduced pressure to obtain the title compound (8.4 g, yield: 99%).

$^1$H NMR (CDCl$_3$) δ: 7.29(d, 1H, J=7.7 Hz), 6.93(d, 1H, J=7.7 Hz), 6.71(t, 1H, J=7.9 Hz), 3.88(s, 3H)

(78-2) Preparation of 3-(5-ethylpyridin-2-ylamino)-2-hydroxybenzoic acid methyl ester (compound 19)

6.9 g (41.3 mmol) of 3-amino-2-hydroxybenzoic acid methyl ester obtained in (78-1) was dissolved in 206 mL of 1,4-dioxane. 5.8 g (41.3 mmol) of 2-chloro-5-ethylpyridine, 0.9 g (4.13 mmol) of Pd(OAc)$_2$, 2.6 g (4.13 mmol) of 2,2'-bis (diphenylphosphino)-1,1'-binaphtyl and 26.9 g (82.6 mmol) of Cs$_2$CO$_3$ were added thereto and stirred at 90° C. for 12 hr. The reaction mixture was cooled to room temperature and concentrated under reduced pressure, followed by dilution with ethyl acetate and washing saturated sodium bicarbonate solution and saturated sodium chloride solution. The washed material was dried over magnesium sulfate and concentrated under reduced pressure, followed by subjecting it to column chromatography (ethyl acetate/hexane=1/4) to obtain the title compound (9.5 g, yield: 85%).

$^1$H NMR (CDCl$_3$) δ: 8.19(d, 1H, J=1.4 Hz), 7.96(s, 1H), 7.49-7.43(m, 2H), 6.91-6.86(m, 2H), 3.96(s, 3H), 2.56 (q, 2H, J=7.6 Hz), 1.21(t, 3H, J=7.6 Hz)

(78-3) Preparation of (S)-4-(5-ethylpyridin-2-yl)-3-(hydroxymethyl)-3,4-dihydro-2H-benzo[b][1,4]oxazin-8-carboxylic acid methyl ester (compound 22)

8.2 g (30.1 mmol) of 3-(5-ethylpyridin-2-ylamino)-2-hydroxybenzoic acid methyl ester obtained in (78-2) was dissolved in 99 mL of dimethylformamide. 8.6 g (33.1 mmol) of (R)-glycidyl nosylate and 8.3 g (60.2 mmol) of K$_2$CO$_3$ were added thereto and stirred at room temperature for 12 hr. The reaction mixture was dissolved in 79 ml of dimethyl formamide and 4.2 g (30.1 mmol) of K$_2$CO$_3$ was further added thereto, followed by stirring at 100° C. for 5 hr. The reaction mixture was cooled to room temperature, concentrated under reduced pressure, diluted with ethyl acetate, and washed with distilled water and saturated sodium chloride solution. The washed material was dried over magnesium sulfate, concentrated under reduced pressure, and the resulting residue was subjected to column chromatography (ethyl acetate/hexane=1/1) to obtain the title compound (8.5 g, yield: 86%).

$^1$H NMR (CDCl$_3$) δ: 8.16(d, 1H, J=2.1 Hz), 7.47(dd, 1H, J=8.4, 2.4 Hz), 7.36-7.31(m, 2H), 7.28(d, 1H, J=8.6 Hz), 6.80(t, 1H, J=8.0 Hz), 5.54 (br, 1H), 4.49(dd, 1H, J=11.1, 1.4 Hz), 4.43-4.39(m, 1H), 4.26(dd, 1H, J=11.1, 3.2 Hz), 3.88(s, 3H), 3.84-3.80(m, 1H), 2.61(q, 2H, J=7.6 Hz), 1.29(t, 3H, J=7.6 Hz)

(78-4) Preparation (S)-4-(5-ethylpyridin-2-yl)-3-(hydroxymethyl)-3,4-dihydro-2H-benzo[b][1,4]oxazin-8-carboxylic acid (compound 23)

6.6 g (20.1 mmol) of (S)-4-(5-ethylpyridin-2-yl)-3-(hydroxymethyl)-3,4-dihydro-2H-benzo[b][1,4]oxazin-8-carboxylic acid methyl ester obtained in (78-3) was dissolved in 66 mL of methanol 7.5 mL of 4N sodium hydroxide solution was added dropwise thereto, stirred at 60° C. for 3 hr and cooled to room temperature. The reaction mixture was neutralized with 30 mL of 1N hydrochloric acid solution, and the resulting solids were filtered. The filtered material was washed with distilled water, followed by drying under vacuum to obtain the title compound (5.9 g, yield: 91%).

$^1$H NMR (CDCl$_3$) δ: 8.19(d, 1H, J=2.0 Hz), 7.66(dd, 1H, J=8.4, 2.5 Hz), 7.39(m, 2H), 6.99(d, 1H, J=8.6 Hz), 6.93(t, 1H, J=8.0 Hz), 4.63(dd, 1H, J=10.8, 1.2 Hz), 4.43-4.39(m, 1H), 4.32(dd, 1H, J=11.1, 2.8 Hz), 3.82(m, 2H), 2.62 (q, 2H, J=7.6 Hz), 1.32(t, 3H, J=7.6 Hz)

(78-5) Preparation of [(S)-8-(6-tert-butyl-1H-benzimidazol-2-yl)-4-(5-ethylpyridin-2-yl)-3,4-dihydro-2H-benzo[1,4]oxazin-3-yl]-methanol (compound 1e)

5.0 g (15.9 mmol) of (S)-4-(5-ethylpyridin-2-yl)-3-(hydroxymethyl)-3,4-dihydro-2H-benzo[b][1,4]oxazin-8-carboxylic acid obtained in (78-4) was dissolved in 240 mL of dimethylformamide. 2.6 g (15.9 mmol) of 4-tert-butylbenzene-1,2-diamine, 4.5 mL (31.8 mmol) of diisopropylethylamine and 7.3 g (19.1 mmol) of O-(7-azabenzotriazole-1-yl)-N,N,N',N'-tetramethyluronium hexafluorophosphate were added thereto and stirred at room temperature for 4 hr. The reaction mixture was diluted with ethyl acetate and washed with saturated sodium bicarbonate solution and saturated sodium chloride solution, followed by drying over magnesium sulfate and concentration under reduced pressure. The resulting residue was dissolved in 240 mL of acetic acid, stirred at 75° C. for 4 hr, followed by cooling to room temperature and concentration under reduced pressure. The concentrate was dissolved in ethyl acetate, washed with saturated sodium bicarbonate solution and saturated sodium chloride solution, dried over magnesium sulfate and concentrated under reduced pressure. The resulting residue was subjected to column chromatography (ethyl acetate/hexane=2/3) to obtain the title compound (6.1 g, yield: 86%).

$^1$H NMR (CDCl$_3$) δ: 12.56(d, 1H, J=5.2), 8.20(d, 1H, J=2.5 Hz), 7.99(d, 1H, J=15.7 Hz), 7.90(m, 1H), 7.82(m, 1H), 7.60 (dd, 2H, J=8.5, 2.5 Hz), 7.52(m, 1H), 7.38(m, 1H), 7.28(d, 1H, J=8.6 Hz), 6.97(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.33(s, 9H), 1.19(t, 3H, J=7.55 Hz)

EXAMPLE 79

Preparation of [(S)-4-(5-ethyl-pyridin-2-yl)-8-(6-trifluoromethyl-1H-benzimidazol-2-yl)-3,4-dihydro-2H-benzo[1,4]oxazin-3-yl]-methanol (compound 1e)

The procedure of Example 78 was repeated except for using 4-(trifluoromethyl)benzene-1,2-diamine instead of 4-tert-butylbenzene-1,2-diamine in (78-5) to obtain the title compound (4.3 g, yield: 94%).

$^1$H NMR (CD$_3$OD) δ: 12.56(d, 1H, J=5.2), 8.20(d, 1H, J=2.5 Hz), 7.99(d, 1H, J=15.7 Hz), 7.90(m, 1H), 7.82(m, 1H), 7.60(dd, 2H, J=8.5, 2.5 Hz), 7.52(m, 1H), 7.38(m, 1H), 7.28 (d, 1H, J=8.6 Hz), 6.97(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 80

Preparation of [(S)-8-(4-chloro-6-trifluoromethyl-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 3-chloro-5-trifluoromethylbenzene-1,2-diamine instead of 4-tert-butylbenzene-1,2-diamine in (78-5) to obtain the title compound (4.5 g, yield: 92%).

$^1$H NMR (CD$_3$OD) δ: 12.81(d, 1H, J=10.6), 8.21(d, 1H, J=2.3 Hz), 7.95(m, 2H), 7.82(s, 1H), 7.61(m, 2H), 7.57(m, 2H), 7.41(dd, 1H, J=8.1, 1.5 Hz), 7.00(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 81

Preparation of [(S)-8-(4-bromo-6-trifluoromethyl-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 3-bromo-5-trifluoromethylbenzene-1,2-diamine instead of 4-tert-butylbenzene-1,2-diamine in (78-5) to obtain the title compound (4.8 g, yield: 90%).

$^1$H NMR (CD$_3$OD) δ: 12.82(s, 1H), 8.20(d, 1H, J=2.1 Hz), 7.86(dd, 1H, J=7.9, 1.5 Hz), 7.63(d, 1H, J=1.6 Hz), 7.60(dd, 1H, J=8.1, 1.4 Hz), 7.28(m, 2H), 7.00(t, 1H, J=8.0 Hz), 5.18 (m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 82

Preparation of [(S)-4-(5-ethyl-pyridin-2-yl)-8-(6-trifluoromethoxy-1H-benzimidazol-2-yl)-3,4-dihydro-2H-benzo[1,4]oxazin-3-yl]-methanol (compound 1e)

The procedure of Example 78 was repeated except for using 4-(trifluoromethoxy)benzene-1,2-diamine instead of 4-tert-butylbenzene-1,2-diamine in (78-5) to obtain the title compound (4.1 g, yield: 88%).

$^1$H NMR (CD$_3$OD) δ: 12.28(d, 1H, J=10.6), 8.14(d, 1H, J=2.3 Hz), 7.82(dd, 1H, J=7.8, 1.4 Hz), 7.70(d, 1H, J=1.6 Hz), 7.57(m, 2H), 7.34(dd, 1H, J=8.1, 1.5 Hz), 6.95(t, 1H, J=8.0 Hz), 5.18(m, 1H), 4.83(d, 1H, J=10.6 Hz), 4.54(m, 1H), 4.22 (m, 1H), 3.69(m, 1H), 3.38-3.52(m, 2H), 2.55(m, 2H), 1.19(t, 3H, J=7.55 Hz)

EXAMPLE 83

Preparation of [(S)-8-(5,6-difluoro-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 4,5-difluorobenzene-1,2-diamine instead of 4-tert-butylbenzene-1,2-diamine in (78-5) to obtain the title compound (4.0 g, yield: 94%).

$^1$H NMR (CD$_3$OD) δ: 12.35(s, 1H), 8.14(d, 1H, J=2.3 Hz), 7.82(dd, 1H, J=7.8, 1.4 Hz), 7.70(d, 1H, J=1.6 Hz), 7.57(m, 2H), 7.34(dd, 1H, J=8.1, 1.5 Hz), 6.95(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 84

Preparation of [(S)-8-(6-chloro-5-fluoro-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 4-chloro-5-fluorobenzene-1,2-diamine instead of 4-tert-butylbenzene-1,2-diamine in (78-5) to obtain the title compound (4.1 g, yield: 93%).
¹H NMR (CD₃OD) δ: 12.39(d, 1H, J=16.0), 8.20(d, 1H, J=2.3 Hz), 7.85(m, 2H), 7.71(m, 1H), 7.57(m, 2H), 7.34(m, 1H), 7.27(d, 1H, J=8.6), 6.96(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 85

Preparation of [(S)-8-(6-bromo-4-fluoro-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 5-bromo-3-fluorobenzene-1,2-diamine instead of 4-tert-butylbenzene-1,2-diamine in (78-5) to obtain the title compound (4.4 g, yield: 91%).
¹H NMR (CD₃OD) δ: 12.63(d, 1H, J=6.6 Hz), 8.20(d, 1H, J=2.1 Hz), 7.86(dd, 1H, J=7.9, 1.5 Hz), 7.63(d, 1H, J=1.6 Hz), 7.60(dd, 1H, J=8.1, 1.4 Hz), 7.28(m, 2H), 6.97(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 86

Preparation of [(S)-8-(4,6-difluoro-1H-benzimidazol-2-yl)-4-(5-ethyl-pyridin-2-yl)-3,4-dihydro-2H-benzo[1,4]oxazin-3-yl]-methanol (compound 1e)

The procedure of Example 78 was repeated except for using 3,5-difluorobenzene-1,2-diamine instead of 4-tert-butylbenzene-1,2-diamine in (78-5) to obtain the title compound (3.8 g, yield: 89%).
¹H NMR (CD₃OD) δ: 12.52(d, 1H, J=6.6 Hz), 8.20(d, 1H, J=2.1 Hz), 7.86(dd, 1H, J=7.9, 1.5 Hz), 7.63(d, 1H, J=1.6 Hz), 7.60(dd, 1H, J=8.1, 1.4 Hz), 7.28(m, 2H), 6.97(t, 1H, J=8.0 Hz), 5.18(m, 1H), 4.83(d, 1H, J=10.6 Hz), 4.54(m, 1H), 4.22(m, 1H), 3.69(m, 1H), 3.38-3.52(m, 2H), 2.55(m, 2H), 1.19(t, 3H, J=7.55 Hz)

EXAMPLE 87

Preparation of 2-[(S)-4-(5-ethyl-pyridin-2-yl)-3-hydroxymethyl-3,4-dihydro-2H-benzo[1,4]oxazin-8-yl]-3H-benzimidazol-5-carbonitrile (compound 1e)

The procedure of Example 78 was repeated except for using 3,4-diaminobenzonitrile instead of 4-tert-butylbenzene-1,2-diamine in (78-5) to obtain the title compound (3.7 g, yield: 90%).
¹H NMR (CD₃OD) δ: 12.63(d, 1H, J=6.6 Hz), 8.20(d, 1H, J=2.5 Hz), 7.88(dt, 1H, J=7.9, 1.4 Hz), 7.80(dd, 1H, J=15.1, 8.3 Hz), 7.59(m, 2H), 7.38(m, 1H), 7.28(d, 1H, J=8.5 Hz), 6.98(m, 1H), 5.19(m, 1H), 4.83(dd, 1H, J=10.6, 3.9 Hz), 4.54(m, 2H), 4.22(m, 1H), 3.69(m, 1H), 3.38-3.52(m, 2H), 2.55(m, 2H), 1.19(t, 3H, J=7.55 Hz)

EXAMPLE 88

Preparation of (S)-8-(6-tert-butyl-1H-benzimidazol-2-yl)-3-methoxymethyl-4-(5-methyl-pyridin-2-yl)-3,4-dihydro-2H-benzo[1,4]oxazine (compound 1f)

(88-1) Preparation of (S)-3-(methoxymethyl)-4-(5-methylpyridin-2-yl)-3,4-dihydro-2H-benzo[b][1,4]oxazin-8-carboxylic acid methyl ester (compound 24)

3.0 g (9.5 mmol) of (S)-3-(hydroxymethyl)-4-(5-methylpyridin-2-yl)-3,4-dihydro-2H-benzo[b][1,4]oxazin-8-carboxylic acid methyl ester (compound 22) obtained in (34-6) were dissolved in 50 mL of THF. The solution was cooled to 0° C. and 1.1 g (28.6 mmol) of NaH was added slowly. The solution was stirred at 0° C. for 10 min and then at room temperature for 5 min. The solution was re-cooled to 0° C. and 120 uL (19.1 mmol) of MeI was added slowly. The mixture was placed at the same temperature for 1-2 hr and stirred while heating to room temperature. When the reaction terminated, the reaction mixture was neutralized by slow addition of 1N HCl solution, and dissolved in ethyl acetate and washed with distilled water and saturated sodium chloride solution, followed by drying over magnesium sulfate and concentration under reduced pressure. The resulting residue was subjected to column chromatography (ethyl acetate/hexane=1/2) to obtain the title compound (2.7 g, yield: 85%).
¹H NMR (CDCl₃) δ: 8.16(d, 1H, J=2.1 Hz), 7.36(m, 3H), 7.41(d, 1H, J=8.4), 6.82(t, 1H, J=8.0 Hz), 4.68(m, 1H), 4.61(dd, 1H, J=10.9, 1.3 Hz), 4.09(dd, 1H, J=10.8, 2.8 Hz), 3.89(s, 3H), 3.62(dd, 1H, J=9.3, 6.2 Hz), 3.48(t, 1H, J=9.0 Hz), 3.39(s, 3H), 2.25(s, 3H)

(88-2) Preparation of (S)-3-(methoxymethyl)-4-(5-methylpyridin-2-yl)-3,4-dihydro-2H-benzo[b][1,4]oxazin-8-carboxylic acid (compound 25)

2.5 g (7.6 mmol) of (S)-3-(methoxymethyl)-4-(5-methylpyridin-2-yl)-3,4-dihydro-2H-benzo[b][1,4]oxazin-8-carboxylic acid methyl ester obtained in (88-1) was dissolved in 25 mL of methanol, 2.9 mL of 4N sodium hydroxide was added dropwise thereto, stirred at 60° C. for 3 hr and cooled to room temperature. The reaction mixture was neutralized with 11 mL of 1N hydrochloric acid and the resulting solids were filtered. The filtered material was washed with distilled water and dried under vacuum to obtain the title compound (2.1 g, yield: 89%).
¹H NMR (CDCl₃) δ: 8.19(d, 1H, J=2.0 Hz), 7.74(dd, 1H, J=7.8, 1.6 Hz), 7.42(m, 2H), 7.12(d, 1H, J=8.4 Hz), 6.95(t, 1H, J=8.0 Hz), 4.80(dd, 1H, 1.4 Hz), 4.72(m, 1H), 4.23(dd, 1H, J=10.5, 2.6 Hz), 3.68(dd, 1H, 5.8 Hz), 3.46(t, 1H, J=9.5 Hz), 3.40(s, 3H), 2.28(s, 3H)

(88-3) Preparation of (S)-8-(6-tert-butyl-1H-benzimidazol-2-yl)-3-methoxymethyl-4-(5-methyl-pyridin-2-yl)-3,4-dihydro-2H-benzo[1,4]oxazine (compound 1f)

2.0 g of (S)-3-(methoxymethyl)-4-(5-methylpyridin-2-yl)-3,4-dihydro-2H-benzo[b][1,4]oxazin-8-carboxylic acid obtained in (88-2) was dissolved in 95 mL of dimethylformamide. 1.0 g (6.4 mmol) of 4-tert-butylbenzene-1,2-diamine, 1.8 mL (12.7 mmol) of diisopropylethylamine and 2.9 g (7.6 mmol) of O-(7-azabenzotriazole-1-yl)-N,N,N',N'-tetramethyluronium hexafluorophosphate were added thereto and stirred at room temperature for 3 hr. The reaction mixture was diluted with ethyl acetate and washed with saturated sodium bicarbonate solution and saturated sodium chloride solution, followed by drying over magnesium sulfate and concentration under reduced pressure. The resulting residue was dissolved in 95 mL of acetic acid and stirred at 75° C. for 4 hr, followed by cooling to room temperature and concentration under reduced pressure. The concentrate was dissolved in ethyl acetate and washed with saturated sodium bicarbonate solution and saturated sodium hydrochloride solution, followed by drying over magnesium sulfate and concentration under reduced pressure. The resulting residue was subjected to column chromatography (ethyl acetate/hexane=2/3) to obtain the title compound (2.3 g, yield: 83%).

¹H NMR (CD₃OD) δ: 8.15(d, 1H, J=2.2 Hz), 7.83(dd, 1H, J=7.8, 1.5 Hz), 7.68(d, 1H, J=1.7 Hz), 7.58(d, 1H, J=8.6 Hz), 7.56(dd, 1H, J=8.3, 2.3 Hz), 7.39(dd, 1H, J=8.6, 1.8 Hz), 7.27(m, 2H), 6.99(t, 1H, J=8.0 Hz), 4.82(dd, 1H, J=10.9, 1.4 Hz), 4.64(m, 1H), 4.22(dd, 1H, J=10.9, 2.6 Hz), 3.69(dd, 1H, J=9.5, 6.1 Hz), 3.56(t, 1H, J=9.3 Hz), 3.41(s, 3H), 2.30(s, 3H), 1.42(s, 9H)

EXAMPLE 89

Preparation of (S)-8-(6-bromo-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 4-bromobenzene-1,2-diamine instead of 4-tert-butylbenzene-1,2-diamine in (88-3) to obtain the title compound (2.3 g, 83%).
¹H NMR (CD₃OD) δ: 8.15(d, 1H, J=2.2 Hz), 7.83(dd, 1H, J=7.8, 1.5 Hz), 7.65(d, 1H, J=1.9 Hz), 7.62(d, 1H, J=8.6 Hz), 7.57(dd, 1H, J=8.5, 2.3 Hz), 7.28(m, 3H), 7.00(t, 1H, J=8.0 Hz), 4.82(dd, 1H, J=11.0, 1.4 Hz), 4.63(m, 1H), 4.22(dd, 1H, J=10.9, 2.6 Hz), 3.68(dd, 1H, J=9.5, 6.0 Hz), 3.56(t, 1H, J=9.2 Hz), 3.41(s, 3H), 2.30(s, 3H)

EXAMPLE 90

Preparation of (S)-3-methoxymethyl-4-(5-methyl-pyridin-2-yl)-8-(6-trifluoromethyl-1H-benzimidazol-2-yl)-3,4-dihydro-2H-benzo[1,4]oxazine (compound 1f)

The procedure of Example 88 was repeated except for using 4-(trifluoromethyl)benzene-1,2-diamine instead of 4-tert-butylbenzene-1,2-diamine in (88-3) to obtain the title compound (2.1 g, yield: 88%).
¹H NMR (CD₃OD) δ: 8.16(d, 1H, J=2.3 Hz), 7.83(dd, 1H, J=7.8, 1.5 Hz), 7.81(d, 1H, J=1.8 Hz), 7.57(dd, 1H, J=8.5, 1.9 Hz), 7.38(dd, 1H, J=8.6, 1.8 Hz), 7.29(m, 2H), 7.00(t, 1H, J=8.0 Hz), 4.82(dd, 1H, J=10.9, 1.4 Hz), 4.63(m, 1H), 4.22(dd, 1H, J=10.9, 2.6 Hz), 3.68(dd, 1H, J=9.5, 6.0 Hz), 3.56(t, 1H, J=9.2 Hz), 3.41(s, 3H), 2.30(s, 3H)

EXAMPLE 91

Preparation of (S)-3-methoxymethyl-4-(5-methyl-pyridin-2-yl)-8-(6-chloro-1H-benzimidazol-2-yl)-3,4-dihydro-2H-benzo[1,4]oxazine (compound 1f)

The procedure of Example 88 was repeated except for using 4-chlorobenzene-1,2-diamine instead of 4-tert-butylbenzene-1,2-diamine in (88-3) to obtain the title compound (1.8 g, yield: 84%).
¹H NMR (CD₃OD) δ: 8.16(d, 1H, J=2.2 Hz), 7.97(s, 1H), 7.88(dd, 1H, J=5.8, 2.0 Hz), 7.81(d, 1H, J=8.5 Hz), 7.57(m, 2H), 7.33(dd, 1H, J=8.2, 1.5 Hz), 7.28(d, 1H, J=8.5), 7.00(t, 1H, J=8.0 Hz), 4.82(dd, 1H, J=10.9, 1.4 Hz), 4.63(m, 1H), 4.25(dd, 1H, J=10.9, 2.7 Hz), 3.69(dd, 1H, J=9.5, 6.1 Hz), 3.57(t, 1H, J=9.2 Hz), 3.41(s, 3H), 2.30(s, 3H)

EXAMPLE 92

Preparation of (S)-8-(4-chloro-6-trifluoromethyl-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3-chloro-5-trifluoromethylbenzene-1,2-diamine instead of 4-tert-butylbenzene-1,2-diamine in (88-3) to obtain the title compound (2.4 g, yield: 94%).
¹H NMR (CD₃OD) δ: 8.16(d, 1H, J=2.0 Hz), 7.94(d, 1H, J=8.0 Hz), 7.91(s, 1H), 7.60(dd, 1H, J=8.5, 2.3 Hz), 7.57(d, 1H, J=1.3 Hz), 7.36(dd, 1H, J=8.2, 1.5 Hz), 7.30(d, 1H, J=8.5 Hz), 7.04(t, 1H, J=8.0 Hz), 4.82(dd, 1H, J=10.9, 1.4 Hz), 4.63(m, 1H), 4.25(dd, 1H, J=10.9, 2.7 Hz), 3.69(dd, 1H, J=9.5, 6.2 Hz), 3.58(t, 1H, J=9.1 Hz), 3.40(s, 3H), 2.31(s, 3H)

EXAMPLE 93

Preparation of (S)-8-(4-bromo-6-trifluoromethyl-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3-bromo-5-(trifluoromethoxy)benzene-1,2-diamine instead of 4-tert-butylbenzene-1,2-diamine in (88-3) to obtain the title compound (2.6 g, yield: 92%).
¹H NMR (CD₃OD) δ: 8.16(d, 1H, J=2.2 Hz), 8.00(d, 1H, J=7.2 Hz), 7.94(s, 1H), 7.71(s, 1H), 7.57(dd, 1H, J=8.4, 2.2 Hz), 7.34(dd, 1H, J=8.1, 1.3 Hz), 7.27(d, 1H, J=8.4 Hz), 7.03(t, 1H, J=8.0 Hz), 4.82(d, 1H, J=10.9), 4.63(m, 1H), 4.24(dd, 1H, J=10.9, 2.7 Hz), 3.69(dd, 1H, J=9.5, 6.1 Hz), 3.56(t, 1H, J=9.4 Hz), 3.40(s, 3H), 2.30(s, 3H)

EXAMPLE 94

Preparation of (S)-8-(6-bromo-4-fluoro-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 5-bromo-3-fluorobenzene-1,2-diamine instead of 4-tert-butylbenzene-1,2-diamine in (88-3) to obtain the title compound (2.3 g, yield: 90%).
¹H NMR (CD₃OD) δ: 8.16(d, 1H, J=2.0 Hz), 7.86(dd, 1H, J=7.9, 1.5 Hz), 7.64(m, 2H), 7.34(m, 2H), 7.23(dd, 1H, J=10.2, 1.5 Hz), 7.03(t, 1H, J=8.0 Hz), 4.82(dd, 1H, J=10.9, 1.3 Hz), 4.63(m, 1H), 4.25(dd, 1H, J=11.0, 2.8 Hz), 3.68(dd, 1H, J=9.5, 6.3 Hz), 3.57(t, 1H, J=9.0 Hz), 3.40(s, 3H), 2.32(s, 3H)

EXAMPLE 95

Preparation of (S)-8-(5,6-dichloro-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 4,5-dichlorobenzene-1,2-diamine instead of 4-tert-butylbenzene-1,2-diamine in (88-3) to obtain the title compound (2.1 g, yield: 87%).
¹H NMR (CD₃OD) δ: 8.16(d, 1H, J=2.2 Hz), 7.82(m, 3H), 7.89(dd, 1H, J=8.4, 2.3 Hz), 7.34(dd, 1H, J=8.2, 1.5 Hz), 7.28(d, 1H, J=8.4 Hz), 7.02(t, 1H, J=8.0 Hz), 4.82(dd, 1H, J=10.9, 1.3 Hz), 4.63(m, 1H), 4.25(dd, 1H, J=11.0, 2.8 Hz), 3.68(dd, 1H, J=9.5, 6.3 Hz), 3.57(t, 1H, J=9.0 Hz), 3.40(s, 3H), 2.31(s, 3H)

EXAMPLE 96

Preparation of (S)-8-(4,6-bis-trifluoromethyl-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3,5-bis-trifluoromethylbenzene-1,2-diamine instead of 4-tert-butylbenzene-1,2-diamine in (88-3) to obtain the title compound (2.5 g, yield: 91%).

$^1$H NMR (CD$_3$OD) δ: 8.16(d, 1H, J=2.2 Hz), 8.04(d, 1H, J=7.7 Hz), 7.76(s, 1H), 7.56(dd, 2H, J=7.6, 1.9 Hz), 7.31(dd, 1H, J=8.2, 1.4 Hz), 7.26(d, 1H, J=8.5 Hz), 6.99(t, 1H, J=4.3 Hz), 4.80(d, 1H, J=10.7 Hz), 4.63(m, 1H), 4.21(dd, 1H, J=10.9, 2.6 Hz), 3.67(dd, 1H, J=9.5, 6.1 Hz), 3.55(t, 1H, J=9.2 Hz), 3.40(s, 3H), 2.30(s, 3H)

EXAMPLE 97

Preparation of (S)-8-(4,6-dibromo-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3,5-dibromobenzene-1,2-diamine instead of 4-tert-butylbenzene-1,2-diamine in (88-3) to obtain the title compound (2.5 g, yield: 87%).

$^1$H NMR (CD$_3$OD) δ: 8.15(d, 1H, J=2.2 Hz), 7.93(d, 1H, J=7.5 Hz), 7.76(s, 1H), 7.56(dd, 2H, J=7.6, 1.9 Hz), 7.31(dd, 1H, J=8.2, 1.4 Hz), 7.26(d, 1H, J=8.5 Hz), 6.99(t, 1H, J=4.3 Hz), 4.80(d, 1H, J=10.7 Hz), 4.63(m, 1H), 4.21(dd, 1H, J=10.9, 2.6 Hz), 3.67(dd, 1H, J=9.5, 6.1 Hz), 3.55(t, 1H, J=9.2 Hz), 3.40(s, 3H), 2.30(s, 3H)

EXAMPLE 98

Preparation of (S)-8-(6-fluoro-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 4-fluorobenzene-1,2-diamine instead of 4-tert-butylbenzene-1,2-diamine in (88-3) to obtain the title compound (2.0 g, yield: 93%).

$^1$H NMR (CD$_3$OD) δ: 8.16(d, 1H, J=2.2 Hz), 7.83(dd, 1H, J=7.9, 1.5 Hz), 7.62(dd, 1H, J=8.9, 4.8 Hz), 7.57(dd, 1H, J=8.5, 2.4 Hz), 7.34(dd, 1H, J=9.2, 2.5 Hz), 7.29(dd, 1H, J=6.6, 1.5 Hz), 7.27(d, 1H, J=8.3 Hz), 7.04(m, 1H), 6.99(t, 1H, J=4.3 Hz), 4.82(dd, 1H, J=10.9, 1.4 Hz), 4.64(m, 1H), 4.22(dd, 1H, J=10.9, 2.7 Hz), 3.69(dd, 1H, J=9.5, 6.1 Hz), 3.56(t, 1H, J=9.2 Hz), 3.41(s, 3H), 2.30(s, 3H)

EXAMPLE 99

Preparation of (S)-3-methoxymethyl-4-(5-methyl-pyridin-2-yl)-8-(6-trifluoromethoxy-1H-benzimidazol-2-yl)-3,4-dihydro-2H-benzo[1,4]oxazine (compound 1f)

The procedure of Example 88 was repeated except for using 4-(trifluoromethoxy)benzene-1,2-diamine instead of 4-tert-butylbenzene-1,2-diamine in (88-3) to obtain the title compound (2.3 g, yield: 94%).

$^1$H NMR (CD$_3$OD) δ: 8.16(d, 1H, J=2.3 Hz), 7.83(dd, 1H, J=7.8, 1.5 Hz), 7.81(d, 1H, J=1.8 Hz), 7.57(dd, 1H, J=8.5, 1.9 Hz), 7.38(dd, 1H, J=8.6, 1.8 Hz), 7.29(m, 2H), 7.00(t, 1H, J=8.0 Hz), 4.82(dd, 1H, J=10.9, 1.4 Hz), 4.63(m, 1H), 4.22 (dd, 1H, J=10.9, 2.6 Hz), 3.68(dd, 1H, J=9.5, 6.0 Hz), 3.56(t, 1H, J=9.2 Hz), 3.41(s, 3H), 2.30(s, 3H)

EXAMPLE 100

Preparation of (S)-8-(6,7-dimethyl-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3,4-dimethylbenzene-1,2-diamine instead of 4-tert-butylbenzene-1,2-diamine in (88-3) to obtain the title compound (2.0 g, yield: 91%).

$^1$H NMR (CD$_3$OD) δ: 8.15(d, 1H, J=2.1 Hz), 7.77(dd, 1H, J=7.5, 1.5 Hz), 7.55(dd, 1H, J=8.5, 2.3 Hz), 7.35(d, 1H, J=8.2 Hz), 7.27(dd, 1H, J=8.1, 1.5 Hz), 7.26(d, 1H, J=7.8 Hz), 7.07(d, 1H, J=8.2 Hz), 6.98(t, 1H, J=4.3 Hz), 4.75(dd, 1H, J=10.9, 1.4 Hz), 4.63(m, 1H), 4.20(dd, 1H, J=10.9, 2.6 Hz), 3.68(dd, 1H, J=9.6, 6.1 Hz), 3.56(t, 1H, J=9.2 Hz), 3.41(s, 3H), 2.56(s, 3H), 2.40(s, 3H), 2.30(s, 3H)

EXAMPLE 101

Preparation of 2-[(S)-3-methoxymethyl-4-(5-methyl-pyridin-2-yl)-3,4-dihydro-2H-benzo[1,4]oxazin-8-yl]-3H-benzimidazol-5-carbonitrile (compound 1f)

The procedure of Example 88 was repeated except for using 3,4-diaminobenzonitrile instead of 4-tert-butylbenzene-1,2-diamine in (88-3) to obtain the title compound (1.9 g, yield: 89%).

$^1$H NMR (CD$_3$OD) δ: 8.16(d, 1H, J=2.2 Hz), 8.03(s, 1H), 7.88(d, 1H, J=7.5 Hz), 7.79(d, 1H, J=8.3 Hz), 7.57(dd, 2H, J=8.4, 1.5 Hz), 7.33(dd, 1H, J=8.1, 1.5 Hz), 7.27(d, 1H, J=8.5 Hz), 7.02(t, 1H, J=8.0 Hz), 4.83(dd, 1H, J=10.9, 1.4 Hz), 4.64(m, 1H), 4.24(dd, 1H, J=10.9, 2.6 Hz), 3.69(dd, 1H, J=9.5, 6.0 Hz), 3.56(t, 1H, J=9.2 Hz), 3.41(s, 3H), 2.30(s, 3H)

EXAMPLE 102

Preparation of (S)-8-(5,6-difluoro-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 4,5-difluorobenzene-1,2-diamine instead of 4-tert-butylbenzene-1,2-diamine in (88-3) to obtain the title compound (2.0 g, yield: 91%).

$^1$H NMR (CD$_3$OD) δ: 8.15(d, 1H, J=2.1 Hz), 7.82(dd, 1H, J=7.8, 1.5 Hz), 7.56(dd, 1H, J=8.5, 2.3 Hz), 7.48(m, 2H), 7.27(m, 2H), 6.98(t, 1H, J=8.0 Hz), 4.81(dd, 1H, J=10.9, 1.4 Hz), 4.63(m, 1H), 4.21(dd, 1H, J=10.9, 2.6 Hz), 3.68(dd, 1H, J=9.5, 6.0 Hz), 3.55(t, 1H, J=9.3 Hz), 3.40(s, 3H), 2.30(s, 3H)

EXAMPLE 103

Preparation of (S)-8-(5-chloro-6-fluoro-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 4-chloro-5-fluorobenzene-1,2-diamine instead of 4-tert-butylbenzene-1,2-diamine in (88-3) to obtain the title compound (2.1 g, yield: 92%).

¹H NMR (CD₃OD) δ: 8.15(d, 1H, J=2.2 Hz), 7.81(dd, 1H, J=7.8, 1.5 Hz), 7.70(d, 1H, J=6.7), 7.56(dd, 1H, J=8.5, 2.3 Hz), 7.47(d, 1H, J=9.4 Hz), 7.28(m, 2H), 6.98(t, 1H, J=8.0 Hz), 4.82(dd, 1H, J=10.9, 1.4 Hz), 4.62(m, 1H), 4.22(dd, 1H, J=10.9, 2.7 Hz), 3.67(dd, 1H, J=9.5, 6.2 Hz), 3.54(t, 1H, J=9.3 Hz), 3.40(s, 3H), 2.30(s, 3H)

EXAMPLE 104

Preparation of (S)-8-(6-bromo-4-methyl-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 5-bromo-3-methylbenzene-1,2-diamine instead of 4-tert-butylbenzene-1,2-diamine in (88-3) to obtain the title compound (2.2 g, yield: 88%).
¹H NMR (CD₃OD) δ: 8.15(d, 1H, J=2.2 Hz), 7.8 s (s, 1H), 7.61(s, 1H), 7.57(dd, 1H, J=8.5, 2.3 Hz), 7.28(m, 2H), 7.19(s, 1H), 7.00(t, 1H, J=8.0 Hz), 4.82(dd, 1H, J=10.9, 1.4 Hz), 4.63(m, 1H), 4.21(dd, 1H, J=10.9, 2.6 Hz), 3.68(dd, 1H, J=9.4, 6.2 Hz), 3.57(t, 1H, J=9.2 Hz), 3.41(s, 3H), 2.64(s, 3H), 2.30(s, 3H)

EXAMPLE 105

Preparation of (S)-8-(4-bromo-6-trifluoromethoxy-1H-benzimidazol-2-yl)-3-methoxymethyl-4-(5-methyl-pyridin-2-yl)-3,4-dihydro-2H-benzo[1,4]oxazine (compound 1f)

The procedure of Example 88 was repeated except for using 3-bromo-5-(trifluoromethoxy)benzene-1,2-diamine instead of 4-tert-butylbenzene-1,2-diamine in (88-3) to obtain the title compound (2.7 g, yield: 94%).
¹H NMR (CD₃OD) δ: 8.15(d, 1H, J=2.2 Hz), 7.95(d, 1H, J=7.6 Hz), 7.56(m, 2H), 7.40(s, 1H), 7.32(dd, 1H, J=8.1, 1.2 Hz), 7.26(d, 1H, J=8.4 Hz), 7.00(t, 1H, J=8.0 Hz), 4.81(d, 1H, J=10.8 Hz), 4.63(m, 1H), 4.22(dd, 1H, J=10.9, 2.6 Hz), 3.68 (dd, 1H, J=9.5, 6.0 Hz), 3.55(t, 1H, J=9.1 Hz), 3.40(s, 3H), 2.30(s, 3H)

EXAMPLE 106

Preparation of (S)-8-(6-methoxy-1H-benzo[d]imidazol-2-yl)-3-(methoxymethyl)-4-(5-methyl-pyridin-2-yl)-3,4-dihydro-2H-benzo[b][1,4]oxazine (compound 1f)

The procedure of Example 88 was repeated except for using 4-methoxybenzene-1,2-diamine instead of 4-tert-butylbenzene-1,2-diamine in (88-3) to obtain the title compound (3.6 g, yield: 87%).
¹H NMR (CD₃OD) δ: 8.15(d, 1H, J=2.2 Hz), 7.81(dd, 1H, J=7.8, 1.5 Hz), 7.54(m, 2H), 7.25(m, 2H), 7.16(d, 1H, J=2.4 Hz), 6.98(t, 1H, J=8.0 Hz), 6.91(dd, 1H, J=8.8, 2.5 Hz), 4.82(dd, 1H, J=11.0, 1.4 Hz), 4.63(m, 1H), 4.22(dd, 1H, J=10.9, 2.6 Hz), 3.86(s, 3H), 3.68(dd, 1H, J=9.5, 6.0 Hz), 3.56(t, 1H, J=9.2 Hz), 3.41(s, 3H), 2.30(s, 3H)

EXAMPLE 107

Preparation of (S)-8-(4,6-difluoro-1H-benzo[d]imidazol-2-yl)-3-(methoxymethyl)-4-(5-methyl-pyridin-2-yl)-3,4-dihydro-2H-benzo[b][1,4]oxazine (compound 1f)

The procedure of Example 88 was repeated except for using 3,5-difluorobenzene-1,2-diamine instead of 4-tert-butylbenzene-1,2-diamine in (88-3) to obtain the title compound (3.7 g, yield: 88%).
¹H NMR (CD₃OD) δ: 8.15(d, 1H, J=2.2 Hz), 7.58(m, 1H), 7.35(dd, 1H, J=8.2, 1.6 Hz), 7.25(m, 1H), 6.97(m, 2H), 4.79 (dd, 1H, J=10.9, 1.3 Hz), 4.61(m, 1H), 4.20(dd, 1H, J=10.9, 2.7 Hz), 3.67(dd, 1H, J=9.5, 6.0 Hz), 3.55(t, 1H, J=9.2 Hz), 3.40(s, 3H), 2.30(s, 3H)

EXAMPLE 108

Preparation of (S)-3-(methoxymethyl)-8-(4-methyl-1H-benzo[d]imidazol-2-yl)-4-(5-methyl-pyridin-2-yl)-3,4-dihydro-2H-benzo[b][1,4]oxazine (compound 1f)

The procedure of Example 88 was repeated except for using 3-methylbenzene-1,2-diamine instead of 4-tert-butylbenzene-1,2-diamine in (88-3) to obtain the title compound (3.7 g, yield: 92%).
¹H NMR (CD₃OD) δ: 8.14(d, 1H, J=2.1 Hz), 7.79(dd, 1H, J=7.8, 1.5 Hz), 7.54(dd, 1H, J=8.4, 2.3 Hz), 7.45(d, 1H, J=7.9 Hz), 7.26(m, 2H), 7.15(t, 1H, J=7.7 Hz), 7.04(d, 1H, J=7.7 Hz), 6.98(t, 1H, J=8.0 Hz), 4.75(dd, 1H, J=10.9, 1.4 Hz), 4.62(m, 1H), 4.20(dd, 1H, J=10.9, 2.6 Hz), 3.67(dd, 1H, J=9.5, 6.0 Hz), 3.56(t, 1H, J=9.2 Hz), 3.40(s, 3H), 2.64(s, 3H), 2.29(s, 3H)

EXAMPLE 109

Preparation of (S)-3-(methoxymethyl)-8-(5-methyl-1H-benzo[d]imidazol-2-yl)-4-(5-methyl-pyridin-2-yl)-3,4-dihydro-2H-benzo[b][1,4]oxazine (compound 1f)

The procedure of Example 88 was repeated except for using 4-methylbenzene-1,2-diamine instead of 4-tert-butylbenzene-1,2-diamine in (88-3) to obtain the title compound (3.6 g, yield: 90%).
¹H NMR (CD₃OD) δ: 8.14(d, 1H, J=2.0 Hz), 7.81(dd, 1H, J=7.8, 1.5 Hz), 7.54(m, 2H), 7.44(s, 1H), 7.25(m, 2H), 7.10 (dd, 1H, J=8.3, 1.3 Hz), 6.98(t, 1H, J=8.0 Hz), 4.75(dd, 1H, J=10.9, 1.4 Hz), 4.62(m, 1H), 4.20(dd, 1H, J=10.9, 2.6 Hz), 3.67(dd, 1H, J=9.5, 6.0 Hz), 3.56(t, 1H, J=9.2 Hz), 3.40(s, 3H), 2.48(s, 3H), 2.29(s, 3H)

EXAMPLE 110

Preparation of (S)-8-(1H-benzo[d]imidazol-2-yl)-3-(methoxymethyl)-4-(5-methyl-pyridin-2-yl)-3,4-dihydro-2H-benzo[b][1,4]oxazine (compound 1f)

The procedure of Example 88 was repeated except for using benzene-1,2-diamine instead of 4-tert-butylbenzene-1,2-diamine in (88-3) to obtain the title compound (3.4 g, yield: 89%).
¹H NMR (CD₃OD) δ: 8.15(d, 1H, J=2.1 Hz), 7.84(dd, 1H, J=7.8, 1.5 Hz), 7.64(m, 2H), 7.55(dd, 1H, J=8.4, 2.3 Hz), 7.27(m, 4H), 6.99(t, 1H, J=8.0 Hz), 4.82(dd, 1H, J=10.9, 1.4 Hz), 4.62(m, 1H), 4.20(dd, 1H, J=10.9, 2.6 Hz), 3.67(dd, 1H, J=9.5, 6.0 Hz), 3.56(t, 1H, J=9.2 Hz), 3.40(s, 3H), 2.29(s, 3H)

EXPERIMENTAL EXAMPLE 1

Inhibitory Effect on Calcium Influx Via a Vanilloid Receptor

In order to confirm the antagonistic activities of the inventive compounds, inhibitory effects of the compounds on calcium influx were examined as follows.

1) Cell Culture hVR-1-HEK293 cell line is a human embryonic kidney (HEK) cell 293 Tet-on strain transformed with a human vanilloid-1 gene (pTRE2hyg-hVR-1 7.8 kb). The cell line can modulate the expression of VR-1, depending on whether doxycycline, a derivative of tetracycline, is present or not.

In order to elucidate the inhibitory effect on calcium influx, the expression of VR-1 was induced by culturing hVR-1-HEK293 cell line in a medium containing doxycycline for 2 days.

Specifically, hVR-1-HEK293 cells were cultured in a T75 flask to about 80% confluency, separated from the flask by treating with trypsin solution, and then collected by centrifugation. The cells were suspended in a medium containing 1 μg/mL of doxycycline, and the resulting suspension was diluted to a concentration of $2 \sim 4 \times 10^5$ cells/mL 100μ, of the cell suspension was placed in each well of a 96-well black plate. The cells were cultured in 5% $CO_2$ incubator at 37° C. for 2 days, and used for the following procedure.

2) Preparation of Compound Samples

The compounds, prepared in the Examples of the present invention, were dissolved in dimethyl sulfoxide (DMSO) to obtain compound samples.

3) Measurement of Calcium Influx

The cells prepared in 1) above were cultured at 37° C. for 90 min in a solution containing Fluo-3/AM, a fluorescent dye, as a calcium indicator so that the fluorescent dye was permeated into the cells. Then the cells were washed three times with D-PBS (Dulbecco's phosphate buffered saline) containing 10 mM HEPES (4-(2-hydroxyethyl)-1-piperazine ethanesulfonic acid) to remove the residual fluorescent dye. 193 μ, of D-PBS was added to each well, followed by addition of various concentrations (0.015~2000 nM) of the compounds. In order to stimulate calcium influx through a vanilloid receptor, the cells were treated with 1 μM of capsaicin. The inhibitory effect of various concentrations (0.015~2000 nM) of compounds on intracellular calcium influx was measured by using a fluorimeter. Equivalent amounts of N-(4-tert-butylphenyl)-4-(3-chloropyridin-2-yl)piperazin-1-carboxyamide (also, referred to BCTC) was used as a control group. The obtained data were input to the Hill equation represented by the following formula I and the values were analyzed:

Intracellular calcium influx=

[(fluorescent intensity of experimental group−fluorescent intensity of background)/(fluorescent intensity of positive control−fluorescent intensity of background)]*100    [Formula I]

The inhibitory activities were evaluated from the obtained intracellular calcium influx values according to the following criteria. The results are shown in the following Table 1.

−: $IC_{50}$>1000 nM; +: $IC_{50}$=501~1000 nM; ++: $IC_{50}$=101~500 nM; +++: $IC_{50}$=20~100 nM; ++++: $IC_{50}$<20 nM

TABLE 1

| Example | I.A.* |
|---------|-------|
| 6 | ++ |
| 7 | − |
| 8 | ++ |
| 9 | ++ |
| 10 | ++++ |
| 11 | +++ |
| 12 | ++ |
| 13 | +++ |
| 14 | +++ |
| 15 | ++ |
| 16 | ++ |
| 17 | − |
| 18 | +++ |
| 19 | +++ |
| 20 | +++ |
| 21 | ++ |
| 22 | − |
| 25 | +++ |
| 26 | ++ |
| 27 | ++ |
| 28 | +++ |
| 29 | ++ |
| 30 | ++ |
| 31 | +++ |
| 32 | ++ |
| 33 | +++ |
| 34 | ++++ |
| 35 | ++++ |
| 36 | ++++ |
| 37 | +++ |
| 38 | ++++ |
| 39 | ++++ |
| 40 | +++ |
| 41 | ++++ |
| 42 | +++ |
| 43 | ++++ |
| 44 | ++++ |
| 45 | ++++ |
| 46 | ++++ |
| 47 | ++++ |
| 48 | +++ |
| 49 | ++++ |
| 50 | ++++ |
| 51 | ++++ |
| 52 | ++++ |
| 53 | ++++ |
| 54 | ++++ |
| 55 | ++++ |
| 56 | ++ |
| 57 | +++ |
| 58 | +++ |
| 59 | ++++ |
| 60 | ++++ |
| 61 | +++ |
| 62 | ++++ |
| 63 | +++ |
| 64 | ++++ |
| 65 | ++++ |
| 66 | ++++ |
| 67 | ++++ |
| 68 | ++++ |
| 69 | +++ |
| 70 | +++ |
| 71 | ++ |
| 72 | + |
| 73 | ++ |
| 74 | ++ |
| 75 | ++ |
| 76 | +++ |
| 77 | +++ |
| 78 | +++ |
| 79 | +++ |
| 80 | ++++ |
| 81 | ++++ |
| 82 | +++ |
| 83 | +++ |
| 84 | +++ |
| 85 | +++ |
| 86 | ++++ |
| 87 | ++++ |
| 88 | ++++ |
| 89 | ++++ |
| 90 | ++++ |
| 91 | ++++ |
| 92 | ++++ |
| 93 | ++++ |
| 94 | ++++ |

TABLE 1-continued

| Example | I.A.* |
|---|---|
| 95 | ++++ |
| 96 | ++++ |
| 97 | ++++ |
| 98 | +++ |
| 99 | +++ |
| 100 | +++ |
| 101 | +++ |
| 102 | ++++ |
| 103 | ++++ |
| 104 | ++++ |
| 105 | ++++ |
| 106 | ++ |
| 107 | + |
| 108 | ++ |
| 109 | ++ |
| 110 | ++ |

*I.A.: inhibitory activity

As shown in Table 1, the compounds of the present invention showed $IC_{50}$ ranging from 0.5 nM to 2.2 nM. In contrast, the control group administered with BCTC showed $IC_{50}$ ranging from 1.9 nM to 3.7 nM. These results demonstrate that the compounds of the present invention have excellent inhibitory activities on the calcium influx.

EXPERIMENTAL EXAMPLE 2

Effect on Pain

In order to evaluate the effect on pain of the compounds prepared in the Examples, behaviors such as twisting or writhing of body resulted from pain were verified by the phenyl-p-quinone (PBQ)-induced writhing experiment using mice.

5 week-old ICR male mice were used as experimental animals and PBQ (0.02%), as a chemical stimulator. The suspensions of 20 mg of the compounds of the present invention and an excipient such as Na—CMC (sodium carboxymethyl cellulose) in 10 mL of saline were used as test compounds. The test compounds were orally administered to the mice and after 1 hour, PBQ was intraperitoneally administrated in an amount of 10 mL per kg of body weight. Also, as a control group, equivalent amounts of BCTC were administered. The writhing number of each mouse was measured for 10 min starting from 5 min after the administration, and the analgesic effect was verified by counting the reduced number compared to the control group administered with only excipient and calculating the % inhibitory rate according to the following Formula 2.

% inhibition rate=(writhing # of control group−writhing # of test group)/writhing # of control group× 100   [Formula 2]

The inhibitory activity was evaluated from the obtained % inhibition rate, according to the following parameters.
+: <20%; ++: 20~50%; +++: 51-80%; ++++: >80%

TABLE 2

| Example | I.A.* |
|---|---|
| 18 | + |
| 19 | ++ |
| 20 | ++ |
| 25 | + |
| 28 | + |
| 31 | ++ |
| 33 | +++ |
| 34 | + |
| 35 | +++ |
| 36 | +++ |
| 37 | +++ |
| 38 | +++ |
| 39 | +++ |
| 40 | ++++ |
| 41 | ++ |
| 42 | +++ |
| 43 | ++ |
| 44 | ++++ |
| 45 | +++ |
| 46 | ++ |
| 47 | ++ |
| 48 | ++ |
| 49 | +++ |
| 50 | + |
| 51 | + |
| 52 | ++ |
| 53 | + |
| 59 | +++ |
| 60 | +++ |
| 66 | +++ |
| 67 | +++ |
| 68 | +++ |
| 69 | +++ |
| 80 | +++ |
| 81 | +++ |
| 82 | +++ |
| 85 | +++ |
| 86 | +++ |
| 87 | +++ |
| 88 | ++ |
| 89 | +++ |
| 90 | +++ |
| 91 | ++ |
| 92 | ++ |
| 93 | ++ |
| 94 | +++ |
| 95 | +++ |
| 96 | ++++ |
| 97 | ++ |
| 98 | ++ |
| 99 | ++++ |
| 100 | ++ |
| 101 | +++ |
| 102 | +++ |
| 103 | +++ |
| 104 | +++ |

*I.A.: inhibitory activity

As can be seen from Table 2, most compounds of the present invention showed inhibition rates of 50% or more (maximum 97%). In contrast, the control group showed 33% (++). These results demonstrate that the compounds of the present invention have excellent analgesic activities.

Accordingly, benzooxazine benzimidazole derivatives of the present invention may be used for the prevention or treatment of diseases associated with antagonistic activity of vanilloid receptors, e.g., pains such as acute pain, chronic pain, neuropathic pain, postoperative pain, migraines, arthralgia; neuropathy; neuronal damages; diabetic neuropathy; neurological disorders; neurodermatitis; stroke; bladder hypersensitivity; obesity; irritable bowel syndrome; respiratory disorders such as cough, asthma, chronic obstructive pulmonary diseases; glaucoma; burns; psoriasis; itching; vomiting; irritation to the skin, eye, and mucous membranes; and inflammatory diseases such as reflux esophagitis, gastricduodenal ulcers and inflammatory intestinal diseases.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (1) or a pharmaceutically acceptable salt, or isomer thereof:

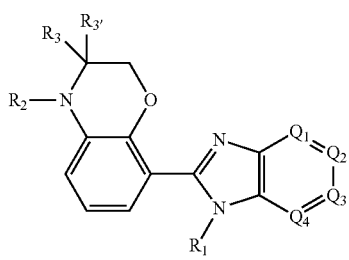

(1)

wherein,

R$^1$ is hydrogen or (CR$^a$R$^{a'}$)$_m$R$^b$, R$^a$ and R$^{a'}$ being each independently hydrogen; C$_1$-C$_8$ alkyl; C$_2$-C$_8$ alkenyl; halogen; nitro; hydroxy; cyano; azido; amino; phenyl; benzyl; C$_1$-C$_8$ alkoxy; C$_1$-C$_6$ alkylamino; or substituted C$_1$-C$_6$ alkyl, phenyl or benzyl having one or more R$^c$ groups; and R$^b$ being hydrogen; hydroxy; or substituted C$_1$-C$_6$ alkyl, phenyl or benzyl having one or more R$^c$ groups; in which R$^c$ is halogen; cyano; nitro; azido; phenyl; benzyl; C(=O)R$^d$; C(=O)OR$^d$;C(=O)NR$^d$R$^d$; OR$^d$; OC(=O)R$^e$; OC(=O) OR$^e$; OC(=O)NR$^d$R$^d$;OC$_1$-C$_6$alkylOR$^d$; OC$_1$-C$_6$alkylNR$^d$R$^d$; SR$^d$; S(=O)R$^e$; S(=O )$_2$R$^e$; S(=O)$_2$NR$^d$R$^d$; CR$^d$=NR$^d$; NR$^d$R$^d$; NR$^d$C(=O)R$^e$; NR$^d$C(=O)OR$^e$; NR$^d$C(=O)NR$^d$R$^d$; NR$^d$C(=NR$^d$)NR$^d$R$^d$; NR$^d$S(=O)$_2$R$^e$; NR$^d$OR$^d$; NR$^d$C$_1$-C$_6$alkylNR$^d$R$^d$; or NR$^d$C$_1$-C$_6$alkylOR$^d$; in which R$^d$ is hydrogen or R$^e$; R$^e$ being phenyl; benzyl; C$_1$-C$_6$ alkyl; phosphoryl; or substituted phenyl, benzyl or C$_1$-C$_6$ alkyl having one or more hydroxy, halogen, C$_1$-C$_4$ alkyl, C$_1$-C$_3$ haloalkyl, C$_1$-C$_4$ alkoxy, amino, C$_1$-C$_4$ alkylamino or di(C$_1$-C$_4$ alkyl)amino groups; and m is 0, 1, or 2;

R$^2$ is hydrogen; C$_1$-C$_8$ alkyl; C$_2$-C$_6$ alkenyl; C$_1$-C$_8$ alkoxy; C$_1$-C$_6$ haloalkyl; C$_1$-C$_6$ haloalkoxy; halogen; nitro; hydroxy; C$_1$-C$_6$ hydroxyalkyl; cyano; amino; amido; substituted amino or amido having one or two C$_1$-C$_6$ alkyl, C$_2$-C$_6$ alkenyl, C$_1$-C$_8$ alkoxy, C$_1$-C$_6$ haloalkyl, C$_1$-C$_6$ haloalkoxy, halogen, nitro, hydroxy, or cyano groups; non-substituted or substituted cycloalkyl, pyridinyl, pyrimidinyl, pyrazolyl, pyrazinyl, phenyl, benzyl, imidazolyl, morpholinyl, benzodioxolyl, benzothiazolyl, benzimidazolyl, indolyl, pyrazolonyl, thiophenyl, furanyl, thiazolyl, isothiazolyl, oxazolyl, isoxazolyl, triazolyl, oxodiazolyl, thiadiazolyl, indazolyl, pyrrolidinyl, chromonyl, piperidinyl, morpholinethyl, dihydropyrazolyl or (CH$_2$)pU having one, two or three sulfonamido groups, in which p is 0, 1, or 2; and U is morpholinyl,

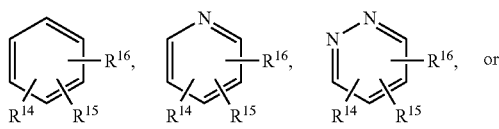

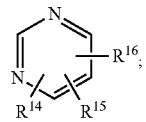

R$^{14}$, R$^{15}$ and R$^{16}$ are independently hydrogen; C$_1$-C$_8$ alkyl; cycloalkyl; C$_2$-C$_6$ alkenyl; C$_1$-C$_6$ haloalkyl; C$_1$-C$_6$ haloalkoxy; halogen; nitro; hydroxy; C$_1$-C$_6$hydroxyalkyl; cyano; sulfanyl; sulfonyl; sulfinyl; sulfonamido; urea; carbamate; carbonate; carbonyl; amino; amido; carboxyl; carboxylester; substituted amino, amido, carboxyl or carboxylester having one or two C$_1$-C$_3$ alkyl groups; or any two of R$^{14}$, R$^{15}$ and R$^{16}$ being fused together to form a saturated or unsaturated heteromonocyclic or heterobicyclic ring;

R$^3$ and R$^{3'}$ are independently hydrogen; C$_1$-C$_{10}$ alkyl; C$_2$-C$_{10}$ alkenyl; C$_2$-C$_{10}$ alkynyl; C$_3$-C$_{10}$ cycloalkyl; C$_8$-C$_{14}$ bicycloalkyl; C$_3$-C$_{10}$ cycloalkenyl; C$_8$-C$_{14}$ bicycloalkenyl; C$_3$-C$_7$ heterocycloalkyl; C$_7$-C$_{10}$ heterobicycloalkyl; C$_1$-C$_6$ hydroxyalkyl; C$_1$-C$_8$ alkoxy; C$_1$-C$_6$ haloalkyl; C$_1$-C$_6$ haloalkoxy; halogen; nitro; hydroxy; cyano; azido; amino; substituted C$_1$-C$_6$ hydroxyalkyl, C$_1$-C$_{10}$ alkyl, C$_2$-C$_{10}$ alkenyl, C$_2$-C$_{10}$ alkynyl, C$_3$-C$_{10}$ cycloalkyl, C$_8$-C$_{14}$ bicycloalkyl, C$_3$-C$_{10}$ cycloalkenyl, C$_8$-C$_{14}$ bicycloalkenyl, C$_3$-C$_7$ heterocycloalkyl or C$_7$-C$_{10}$ heterobicycloalkyl having one or more R$^f$substituents; phenyl; naphtyl; benzyl; C$_5$-C$_{10}$ heteroaryl; or substituted phenyl, naphtyl, benzyl or C$_5$-C$_{10}$ heteroaryl having one or more R$^f$ substituents; wherein Q$^1$ is N or CR$^4$;
Q$^2$ is N or CR$^5$;
Q$^3$ is N or CR$^6$;
Q$^4$ is N or CR$^7$;

R$^4$, R$^5$, R$^6$, and R$^7$ are independently hydrogen; C$_1$-C$_{10}$ alkyl; C$_2$-C$_{10}$ alkenyl; C$_2$-C$_{10}$ alkynyl; C$_3$-C$_{10}$ cycloalkyl; C$_8$-C$_{14}$ bicycloalkyl; C$_3$-C$_{10}$ cycloalkenyl; C$_8$-C$_{14}$ bicycloalkenyl; C$_3$-C$_7$ heterocycloalkyl; C$_7$-C$_{10}$ heterobicycloalkyl; C$_1$-C$_8$ alkoxy; C$_1$-C$_6$ haloalkyl; C$_1$-C$_6$ haloalkoxy; halogen; nitro; hydroxy; cyano; azido; amino; substituted C$_3$-C$_{10}$ alkyl, C$_2$-C$_{10}$ alkenyl, C$_2$-C$_{10}$ alkynyl, C$_3$-C$_{10}$ cycloalkyl, C$_8$-C$_{14}$ bicycloalkyl, C$_3$-C$_{10}$ cycloalkenyl, C$_8$-C$_{14}$ bicycloalkenyl, C$_3$-C$_7$ heterocycloalkyl or C$_7$-C$_{10}$ heterobicycloalkyl having one or more R$^h$ groups; phenyl; naphtyl; benzyl; C$_5$-C$_{10}$ heteroaryl; substituted phenyl, naphtyl, benzyl or C$_5$-C$_{10}$ heteroaryl having one or more R$^h$ substituents; C(=O)R$^i$; C(=O)OR$^i$; C(=O)NR$^i$R$^i$; OR$^i$; OC(=O)R$^j$; OC(=O)OR$^j$; OC(=O)NR$^i$R$^i$; OC$_1$-C$_6$alkylOR$^i$; OC$_1$-C$_6$alkylNR$^i$R$^i$; SR$^i$, S(=O)R$^j$; S(=O)$_2$R$^j$; S(=O)$_2$NR$^i$R$^i$; CR$^i$=NR$^i$; NR$^i$R$^i$; NR$^i$C(=O)R$^j$; NR$^i$C(=O)OR$^j$; NR$^i$C(=O)NR$^i$R$^i$; NR$^i$C(=NR$^i$)NR$^i$R$^i$; NR$^i$S(=O)$_2$R$^j$; NR$^i$OR$^i$; NR$^i$C$_1$-C$_6$alkylNR$^i$R$^i$; or NR$^i$C$_1$-C$_6$alkylOR$^i$; or any two of R$^4$, R$^5$, R$^6$ and R$^7$ are fused together to form a saturated, partially saturated or unsaturated 5-, 6- or 7-membered heteromonocyclic ring or a saturated, partially saturated, or unsaturated 6-, 7-, 8-, 9-, 10- or 11-membered heterobicyclic ring which is optionally mono-, di-, tri- or tetra-substituted with a nitrogen, an oxygen or a sulfur groups; in which R$^f$ and R$^h$ are each independently C$_1$-C$_6$ alkyl; C$_2$-C$_6$ alkenyl; C$_2$-C$_6$ alkynyl; C$_3$-C$_8$ cycloalkyl; C$_5$-C$_8$ cycloalkenyl; C$_3$-C$_5$ heterocycloalkyl; C$_1$-C$_6$ haloalkyl; C$_1$-C$_6$ haloalkoxy; halogen; azido; nitro; cyano; phenyl; benzyl; C(=O)R$^i$;

C(=O)OR$^i$, C(=O)NR$^i$R$^j$; OR$^i$; OC(=O)R$^j$; OC(=O) OR$^j$; OC(=O)NR$^i$R$^j$; OC$_1$-C$_6$alkylOR$^i$; OC$_1$-C$_6$alkylNR$^i$R$^j$; SR$^i$; S(=O)R$^j$; S(=O)$_2$R$^j$; S(=O)$_2$ R$^i$R$^j$; CR$^i$=NR$^i$; NR$^i$R$^j$; NR$^i$C(=O)R$^j$; NR$^i$C(=O)OR$^j$; NR$^d$C(=O)NR$^i$R$^j$; NR$^i$C(=NR$^i$)NR$^i$R$^j$; NR$^i$S(=O)$_2$R$^j$; NR$^i$OR$^i$; NR$^i$C$_1$-C$_6$alkylNR$^i$R$^j$; or NR$^i$C$_1$-C$_6$alkylOR$^i$; and R$^i$ is hydrogen or R$^j$; R$^j$; being phenyl; benzyl; C$_1$-C$_6$ alkyl; C$_2$-C$_6$ alkenyl; C$_2$-C$_6$ alkynyl; C$_3$-C$_8$ cycloalkyl; C$_5$-C$_8$ cycloalkenyl; C$_3$-C$_5$ heterocycloalkyl; phosphoryl; or substituted phenyl, benzyl or C$_1$-C$_6$ alkyl having one or more hydroxy, halogen, C$_1$-C$_4$ alkyl, C$_1$-C$_3$ haloalkyl, C$_1$-C$_4$ alkoxy, amino, C$_1$-C$_4$ alkylamino or di(C$_1$-C$_4$ alkyl)amino groups.

2. The compound according to claim 1, or the pharmaceutically acceptable salt, or isomer thereof, wherein,
R$^1$ is hydrogen;
R$^2$ is (CH$_2$)pU, in which p is 0, 1, or 2, and U is morpholinyl or

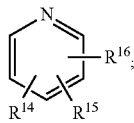

R$^{14}$, R$^{15}$ and R$^{16}$ are each independently hydrogen, C$_1$-C$_2$ alkyl, C$_2$-C$_3$ alkenyl, C$_1$-C$_2$ haloalkyl, C$_1$-C$_2$ haloalkoxy, halogen, hydroxy, or C$_1$-C$_6$ hydroxyalkyl;
R$^3$ and R$^{3'}$ are each independently hydrogen, C$_1$-C$_3$ hydroxyalkyl, or C$_1$-C$_3$ alkoxy; and
Q$^1$ is CR$^4$, Q$^2$ is CR$^5$, Q$^3$ is CR$^6$, and Q$^4$ is CR$^7$, wherein R$^4$, R$^5$, R$^6$, and R$^7$ are each independently hydrogen, C$_1$-C$_4$ alkyl, C$_1$-C$_2$ alkoxy, C$_1$-C$_2$ haloalkyl, C$_1$-C$_2$ haloalkoxy, halogen, hydroxy, or cyano.

3. The compound according to claim 2, or the pharmaceutically acceptable salt, or isomer thereof, wherein
R$^1$ is hydrogen;
R$^2$ is (CH$_2$)pU, in which p is 0, and U is

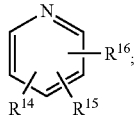

R$^{14}$, R$^{15}$ and R$^{16}$ are each independently hydrogen, C$_1$-C$_2$ alkyl, C$_2$-C$_3$ alkenyl, or halogen;
R$^3$ and R$^{3'}$ are each independently hydrogen, C$_1$-C$_3$ hydroxyalkyl, or C$_1$-C$_3$ alkoxy; and
Q$^1$ is CR$^4$, Q$^2$ is CR$^5$, Q$^3$ is CR$^6$, Q$^4$ is CR$^7$, wherein R$^4$, R$^5$, R$^6$, and R$^7$ are each independently hydrogen, C$_1$-C$_4$ alkyl, C$_1$-C$_2$ alkoxy, C$_1$-C$_2$ haloalkyl, C$_1$-C$_2$ haloalkoxy, halogen, hydroxy, or cyano.

4. The compound according to claim 1, or the pharmaceutically acceptable salt, or isomer thereof, which is selected from the group consisting of:
1) 8-(5-tert-butyl-1H-benzo[d]imidazol-2-yl)-3,4-dihydro-2H-benzo[b][1,4]oxazine,
2) 8-(6-(trifluoromethyl)-1H-benzo[d]imidazol-2-yl)-3,4-dihydro-2H-benzo[b][1,4]oxazine,
3) 8-(6-bromo-1H-benzo[d]imidazol-2-yl)-3,4-dihydro-2H-benzo[b][1,4]oxazine,
4) 8-(6-chloro-1H-benzo[d]imidazol-2-yl)-3,4-dihydro-2H-benzo[b][1,4]oxazine,
5) 8-(5,6-dichloro-1H-benzo[d]imidazol-2-yl)-3,4-dihydro-2H-benzo[b][1,4]oxazine,
6) 8-(6-tert-butyl-1H-benzimidazol-2-yl)-4-(3-chloro-pyridin-2-yl)-3,4-dihydro-2H-benzo[1,4]oxazine,
7) 8-(6-tert-butyl-1H-benzimidazol-2-yl)-4-(3-trifluoromethyl-pyridin-2-yl)-3,4-dihydro-2H-benzo[1,4]oxazine,
8) 8-(6-tert-butyl-1H-benzimidazol-2-yl)-4-(5-trifluoromethyl-pyridin-2-yl)-3,4-dihydro-2H-benzo[1,4]oxazine,
9) 8-(6-tert-butyl-1H-benzimidazol-2-yl)-4-(3-chloro-5-trifluoromethyl-pyridin-2-yl)-3,4-dihydro-2H-benzo[1,4]oxazine,
10) 8-(5-tert-butyl-1H-benzimidazol-2-yl)-4-(5-methyl-pyridin-2-yl)-3,4-dihydro-2H-benzo[1,4]oxazine,
11) 8-(5-tert-butyl-1H-benzimidazol-2-yl)-4-(3,5-dichloro-pyridin-2-yl)-3,4-dihydro-2H-benzo[1,4]oxazine,
12) 8-(5-tert-butyl-1H-benzimidazol-2-yl)-4-pyridin-2-yl)-3,4-dihydro-2H-benzo[1,4]oxazine,
13) 4-(5-bromo-pyridin-2-yl)-8-(5-tert-butyl-1H-benzimidazol-2-yl)-3,4-dihydro-2H-benzo[1,4]oxazine,
14) 8-(5-tert-butyl-1H-benzimidazol-2-yl)-4-(5-chloro-pyridin-2-yl)-3,4-dihydro-2H-benzo[1,4]oxazine,
15) 6-[8-(5-tert-butyl-1H-benzimidazol-2-yl)-2,3-dihydro-benzo[1,4]oxazin-4-yl]-pyridin-3-yl-methanol,
16) 4-(3-chloro-pyridin-2-yl)-8-(6-trifluoromethyl-1H-benzimidazol-2-yl)-3,4-dihydro-2H-benzo[1,4]oxazine,
17) 8-(6-trifluoromethyl-1H-benzimidazol-2-yl)-4-(3-triflurormethyl-pyridin-2-yl)-3,4-dihydro-2H-benzo[1,4]oxazine,
18) 4-(3,5-dichloro-pyridin-2-yl)-8-(6-trifluoromethyl-1H-benzimidazol-2-yl)-3,4-dihydro-2H-benzo[1,4]oxazine,
19) 4-(5-bromo-pyridin-2-yl)-8-(6-trifluoromethyl-1H-benzimidazol-2-yl)-3,4-dihydro-2H-benzo[1,4]oxazine,
20) 4-(5-chloro-pyridin-2-yl)-8-(6-trifluoromethyl-1H-benzimidazol-2-yl)-3,4-dihydro-2H-benzo[1,4]oxazine,
21) 8-(6-bromo-1H-benzimidazol-2-yl)-4-(3-chloro-pyridin-2-yl)-3,4-dihydro-2H-benzo[1,4]oxazine,
22) 8-(6-chloro-1H-benzimidazol-2-yl)-4-(3-chloro-pyridin-2-yl)-3,4-dihydro-2H-benzo[1,4]oxazine,
23) 8-(5,6-dichloro-1H-benzimidazol-2-yl)-4-(2-morpholine-4-yl-ethyl)-3,4-dihydro-2H-benzo[1,4]oxazine,
24) 8-(5,6-dichloro-1H-benzimidazol-2-yl)-4-pyridin-3-yl-methyl-3,4-dihydro-2H-benzo[1,4]oxazine,
25) 4-(5-methyl-pyridin-2-yl)-8-(6-trifluoromethyl-1H-benzimidazol-2-yl)-3,4-dihydro-2H-benzo[1,4]oxazine,
26) 8-(6-bromo-1H-benzimidazol-2-yl)-4-(5-methyl-pyridin-2-yl)-3,4-dihydro-2H-benzo[1,4]oxazine,
27) 8-(5-chloro-1H-benzimidazol-2-yl)-4-(5-methyl-pyridin-2-yl)-3,4-dihydro-2H-benzo[1,4]oxazine,
28) 8-(5,6-dichloro-1H-benzimidazol-2-yl)-4-(5-methyl-pyridin-2-yl)-3,4-dihydro-2H-benzo[1,4]oxazine,
29) 8-(4-chloro-6-trifluoromethyl-1H-benzimidazol-2-yl)-4-(5-methyl-pyridin-2-yl)-3,4-dihydro-2H-benzo[1,4]oxazine,
30) 8-(4,6-bis-trifluoromethyl-1H-benzimidazol-2-yl)-4-(5-methyl-pyridin-2-yl)-3,4-dihydro-2H-benzo[1,4]oxazine,
31) 8-(4-bromo-6-trifluoromethyl-1H-benzimidazol-2-yl)-4-(5-methyl-pyridin-2-yl)-3,4-dihydro-2H-benzo[1,4]oxazine, 32) 8-(4,6-dibromo-1H-benzimidazol-2-yl)-4-(5-methyl-pyridin-2-yl)-3,4-dihydro-2H-benzo[1,4]oxazine,
33) 8-(6-bromo-4-fluoro-1H-benzimidazol-2-yl)-4-(5-methyl-pyridin-2-yl)-3,4-dihydro-2H-benzo[1,4]oxazine,
34) [(S)-8-(6-tert-butyl-1H-benzimidazol-2-yl)-4-(5-methyl-pyridin-2-yl)-3,4-dihydro-2H-benzo[1,4]oxazin-3-yl]-methanol,
35) [(S)-4-(5-methyl-pyridin-2-yl)-8-(6-trifluoromethyl-1H-benzimidazol-2-yl)-3,4-dihydro-2H-benzo[1,4]oxazin-3-yl]-methanol,
36) [(S)-8-(6 bromo-1H-benzimidazol-2-yl)-4-(5-methyl-pyridin-2-yl)-3,4-dihydro-2H-benzo[1,4]oxazin-3-yl]-methanol,
37) [(S)-8-(6-chloro-1H-benzimidazol-2-yl)-4-(5-methyl-pyridin-2-yl)-3,4-dihydro-2H-benzo[1,4]oxazin-3-yl]-methanol,
38) [(S)-8-(5,6-dichloro-1H-benzimidazol-2-yl)-4-(5-methyl-pyridin-2-yl)-3,4-dihydro-2H-benzo[1,4]oxazin-3-3yl]-methanol,
39) [(S)-8-(4-chloro-6-trifluoromethyl-1H-benzimidazol-2-yl)-4-(5-methyl -pyridin-2-yl)-3,4-dihydro-2H-benzo[1,4]oxazin-3-yl]-methanol,
40) [(S)-8-(4,6-bis-trifluoromethyl-1H-benzimidazol-2-yl)-4-(5-methyl-pyridin-2-yl)-3,4-dihydro-2H-benzo[1,4]oxazin-3-yl]-methanol,
41) [(S)-8-(4-bromo-6-trifluoromethyl-1H-benzimidazol-2-yl)-4-(5-methyl -pyridin-2-yl)-3,4-dihydro-2H-benzo[1,4]oxazin-3-yl]-methanol,
42) [(S)-8-(4,6-dibromo-1H-benzimidazol-2-yl)-4-(5-methyl-pyridin-2-yl)-3,4-dihydro-2H-benzo[1,4]oxazin-3yl]-methanol,
43) [(S)-8-(6-bromo-4-fluoro-1H-benzimidazol-2-yl)-4-(5-methyl-pyridin-2-yl)-3,4-dihydro-2H-benzo[1,4]oxazin-3-yl]-methanol,
44) [(S)-8-(5,6-difluoro-1H-benzimidazol-2-yl)-4-(5-methyl-pyridin-2-yl)-3,4-dihydro-2H-benzo[1,4]oxazin-3-yl]-methanol,
45) [(S)-8-(6-chloro-5-fluoro-1H-benzimidazol-2-yl)-4-(5-methyl-pyridin-2-yl)-3,4-dihydro-2H-benzo[1,4]oxazin-3yl]-methanol,
46) [(S)-8-(6-bromo-4-methyl-1H-benzimidazol-2-yl)-4-(5-methyl-pyridin-2-yl)-3,4-dihydro-2H-benzo[1,4]oxazin-3-yl]-methanol,
47) [(S)-4-(5-methyl-pyridin-2-yl)-8-(6-trifluoromethoxy-1H-benzimidazol-2-yl)-3,4-dihydro-2H-benzo[1,4]oxazin-3-yl]-methanol,
48) [(S)-8-(6-methoxy-1H-benzimidazol-2-yl)-4-(5-methyl-pyridin-2-yl)-3,4-dihydro-2H-benzo[1,4]oxazin-3-yl]-methanol,
49) [(S)-8-(6-fluoro-1H-benzimidazol-2-yl)-4-(5-methyl-pyridin-2-yl)-3,4-dihydro-2H-benzo[1,4]oxazin-3-yl]-methanol,
50) [(S)-8-(4-methyl-1H-benzimidazol-2-yl)-4-(5-methyl-pyridine-2-yl)-3,4-dihydro-2H-benzo[1,4]oxazin-3-3-yl]-methanol,
51) [(S)-8-(5-methyl-1H-benzimidazol-2-yl)-4-(5-methyl-pyridin-2-yl)-3,4-dihydro-2H-benzo[1,4]oxazin-3-yl]-methanol,
52) [(S)-8-(4,5-dimethyl-1H-benzimidazol-2-yl)-4-(5-methyl-pyridin-2-yl)-3,4-dihydro-2H-benzo[1,4]oxazin-3-yl]-methanol,
53) [(S)-8-(1H-benzimidazol-2-yl)-4-(5-methyl-pyridin-2-yl)-3,4-dihydro-2H -benzo[1,4]oxazin-3-yl]-methanol,
54) [(S)-8-(4-bromo-6-trifluoromethoxy-1H-benzimidazol-2-yl)-4-(5-methyl -pyridine-2-yl)-3,4-dihydro-2H-benzo[1,4]oxazin-3-yl]-methanol,
55) [(S)-8-(4,6-difluoro-1H-benzo[d]imidazol-2-yl)-4-(5-methyl-pyridin-2-yl)-3,4-dihydro-2H-benzo[b][1,4]oxazin-3-yl]-methanol,
56) (S)-2-(3-(hydroxymethyl)-4-(5-methyl-pyridin-2-yl)-3,4-dihydro-2H-benzo[b][1,4]oxazin-8-yl)-1H-benzo[d]imidazol-6-carbonitrile,
57) [(S)-8-(6-tert-butyl-1H-benzimidazol-2-yl)-4-(5-vinyl-pyridin-2-yl)-3,4-dihydro-2H-benzo[1,4]oxazin-3-yl]-methanol,
58) [(S)-8-(6-trifluoromethyl-1H-benzimidazol-2-yl)-4-(5-vinyl-pyridin-2-yl)-3,4-dihydro-2H-benzo[1,4]oxazin-3-yl]-methanol,
59) [(S)-8-(6-chloro-1H-benzimidazol-2-yl)-4-(5-vinyl-pyridin-2-yl)-3,4-dihydro-2H-benzo[1,4]oxazin-3-yl]-methanol,
60) [(S)-8-(6-bromo-1H-benzimidazol-2-yl)-4-(5-vinyl-pyridin-2-yl)-3,4-dihydro-2H-benzo[1,4]oxazin-3-yl]-methanol,
61) [(S)-8-(6-fluoro-1H-benzimidazol-2-yl)-4-(5-vinyl-pyridin-2-yl)-3,4-dihydro-2H-benzo[1,4]oxazin-3-yl]-methanol,
62) [(S)-8-(6-bromo-4-fluoro-1H-benzimidazol-2-yl)-4-(5-vinyl-pyridin-2-yl)-3,4-dihydro-2H-benzo[1,4]oxazin-3-yl]-methanol,
63) [(S)-8-(4,6-difluoro-1H-benzimidazol-2-yl)-4-(5-vinyl-pyridin-2-yl)-3,4-dihydro-2H-benzo[1,4]oxazin-3-yl]-methanol,
64) [(S)-8-(4-bromo-6-trifluoromethyl-1H-benzimidazol-2-yl)-4-(5-vinyl-pyridin-2-yl)-3,4-dihydro-2H-benzo[1,4]oxazin-3-yl]-methanol,
65) [(S)-8-(4-chloro-6-trifluoromethyl-1H-benzimidazol-2-yl)-4-(5-vinyl-pyridin-2-yl)-3,4-dihydro-2H-benzo[1,4]oxazin-3-yl]-methanol,
66) [(S)-8-(6-bromo-4-methyl-1H-benzimidazol-2-yl)-4-(5-vinyl-pyridin-2-yl)-3,4-dihydro-2H-benzo[1,4]oxazin-3-yl]-methanol,
67) [(S)-8-(6-trifluoromethoxy-1H-benzimidazol-2-yl)-4-(5-vinyl-pyridin-2-yl)-3,4-dihydro-2H-benzo[1,4]oxazin-3-yl]-methanol,
68) [(S)-8-(5,6-dichloro-1H-benzimidazol-2-yl)-4-(5-vinyl-pyridin-2-yl)-3,4-dihydro-2H-benzo[1,4]oxazin-3-yl]-methanol,
69) [(S)-8-(5,6-difluoro-1H-benzimidazol-2-yl)-4-(5-vinyl-pyridin-2-yl)-3,4-dihydro-2H-benzo[1,4]oxazin-3-yl]-methanol,
70) [(S)-8-(6-chloro-5-fluoro-1H-benzimidazol-2-yl)-4-(5-vinyl-pyridin-2-yl)-3,4-dihydro-2H-benzo[1,4]oxazin-3-yl]-methanol,
71) ((S)-8-(4,6-bis(trifluoromethyl)-1H-benzo[d]imidazol-2-yl)-4-(5-vinyl -pyridin-2-yl)-3,4-dihydro-2H-benzo[b][1,4]oxazin-3-yl) -methanol,
72) (S)-(8-(6-methoxy-1H-benzo[d]imidazol-2-yl)-4-(5-vinyl-pyridin-2-yl)-3,4-dihydro-2H-benzo[b][1,4]oxazin-3-yl)methanol,
73) (S)-2-(3-(hydroxymethyl)-4-(5-vinyl-pyridin-2-yl)-3,4-dihydro-2H-benzo[b][1,4]oxazin-8-yl)-1H-benzo[d]imidazol-6-carbonitrile,
74) (S)-(8-(6-methyl-1H-benzo[d]imidazol-2-yl)-4-(5-vinyl-pyridin-2-yl)-3,4-dihydro-2H-benzo[b][1,4]oxazin-3-yl)methanol,
75) (S)-(8-(1H-benzo[d]imidazol-2-yl)-4-(5-vinyl-pyridin-2-yl)-3,4-dihydro-2H-benzo[b][1,4]oxazin-3-yl)methanol, 76) (S)-(8-(4-methyl-1H-benzo[d]imidazol-2-yl)-4-(5-vinyl-pyridin-2-yl)-3,4-dihydro-2H-benzo[b][1,4]oxazin-3-yl)methanol,
77) (S)-(8-(4,5-dimethyl-1H-benzo[d]imidazol-2-yl)-4-(5-vinyl-pyridin-2-yl)-3,4-dihydro-2H-benzo[b][1,4]oxazin-3-yl)methanol,
78) [(S)-8-(6-tert-butyl-1H-benzimidazol-2-yl)-4-(5-ethyl-pyridin-2-yl)-3,4-dihydro-2H-benzo[1,4]oxazin-3-yl]-methanol,
79) [(S)-4-(5-ethyl-pyridin-2-yl)-8-(6-trifluoromethyl-1H-benzimidazol-2-yl)-3,4-dihydro-2H-benzo[1,4]oxazin-3-yl]-methanol,
80) [(S)-8-(4-chloro-6-trifluoromethyl-1H-benzimidazol-2-yl)-4-(5-ethyl-pyridin-2-yl)-3,4-dihydro-2H-benzo[1,4]oxazin-3-yl]-methanol,
81) [(S)-8-(4-bromo-6-trifluoromethyl-1H-benzimidazol-2-yl)-4-(5-ethyl-pyridin-2-yl)-3,4-dihydro-2H-benzo[1,4]oxazin-3-yl]-methanol,
82) [(S)-4-(5-ethyl-pyridin-2-yl)-8-(6-trifluoromethoxy-1H-benzimidazol-2-yl)-3,4-dihydro-2H-benzo[1,4]oxazin-3-yl]-methanol,
83) [(S)-8-(5,6-difluoro-1H-benzimidazol-2-yl)-4-(5-ethyl-pyridin-2-yl)-3,4-dihydro-2H-benzo[1,4]oxazin-3-yl]-methanol,
84) [(S)-8-(6-chloro-5-fluoro-1H-benzimidazol-2-yl)-4-(5-ethyl-pyridin-2-yl)-3,4-dihydro-2H-benzo[1,4]oxazin-3-yl]-methanol,
85) [(S)-8-(6-bromo-4-fluoro-1H-benzimidazol-2-yl)-4-(5-ethyl-pyridin-2-yl)-3,4-dihydro-2H-benzo[1,4]oxazin-3-yl]-methanol,
86) [(S)-8-(4,6-difluoro-1H-benzimidazol-2-yl)-4-(5-ethyl-pyridin-2-yl)-3,4-dihydro-2H-benzo[1,4]oxazin-3-yl]-methanol,
87) 2-[(S)-4-(5-ethyl-pyridin-2-yl)-3-hydroxymethyl-3,4-dihydro-2H-benzo[1,4]oxazin-8-yl]-3H-benzimidazol-5-carbonitrile,
88) (S)-8-(6-tert-butyl-1H-benzimidazol-2-yl)-3-methoxymethyl-4-(5-methyl-pyridin-2-yl)-3,4-dihydro-2H-benzo[1,4]oxazine,
89) (S)-8-(6-bromo-1H-benzimidazol-2-yl)-3-methoxymethyl-4-(5-methyl-pyridin-2-yl)-3,4-dihydro-2H-benzo[1,4]oxazine,
90) (S)-3-methoxymethyl-4-(5-methyl-pyridin-2-yl)-8-(6-trifluoromethyl-1H-benzimidazol-2-yl)-3,4-dihydro-2H-benzo[1,4]oxazine,
91) (S)-3-methoxymethyl-4-(5-methyl-pyridin-2-yl)-8-(6-trifluoromethylchloro-1H-benzimidazol-2-yl)-3,4-dihydro-2H-benzo[1,4]oxazine,
92) (S)-8-(4-chloro-6-trifluoromethyl-1H-benzimidazol-2-yl)-3-methoxymethyl-4-(5-methyl-pyridin-2-yl)-3,4-dihydro-2H-benzo[1,4]oxazine,
93) (S)-8-(4-bromo-6-trifluoromethyl-1H-benzimidazol-2-yl)-3-methoxymethyl-4-(5-methyl-pyridin-2-yl)-3,4-dihydro-2H-benzo[1,4]oxazine,
94) (S)-8-(6-bromo-4-fluoro-1H-benzimidazol-2-yl)-3-methoxymethyl-4-(5-methyl-pyridin-2-yl)-3,4-dihydro-2H-benzo[1,4]oxazine,
95) (S)-8-(5,6-dichloro-1H-benzimidazol-2-yl)-3-methoxymethyl-4-(5-methyl-pyridin-2-yl)-3,4-dihydro-2H-benzo[1,4]oxazine,
96) (S)-8-(4,6-bis-trifluoromethyl-1H-benzimidazol-2-yl)-3-methoxymethyl-4-(5-methyl-pyridin-2-yl)-3,4-dihydro-2H-benzo[1,4]oxazine,
97) (S)-8-(4,6-dibromo-1H-benzimidazol-2-yl)-3-methoxymethyl-4-(5-methyl-pyridin-2-yl)-3,4-dihydro-2H-benzo[1,4]oxazine,
98) (S)-8-(6-fluoro-1H-benzimidazol-2-yl)-3-methoxymethyl-4-(5-methyl-pyridin-2-yl)-3,4-dihydro-2H-benzo[1,4]oxazine,
99) (S)-3-methoxymethyl-4-(5-methyl-pyridin-2-yl)-8-(6-trifluoromethoxy-1H-benzimidazol-2-yl)-3,4-dihydro-2H-benzo[1,4]oxazine,
100) (S)-8-(6,7-dimethyl-1H-benzimidazol-2-yl)-3-methoxymethyl-4-(5-methyl-pyridin-2-yl)-3,4-dihydro-2H-benzo[1,4]oxazine,
101) 2-[(S)-3-methoxymethyl-4-(5-methyl-pyridin-2-yl)-3,4-dihydro-2H-benzo[1,4]oxazin-8-yl]-3H-benzimidazol-5-carbonitrile,
102) (S)-8-(5,6-difluoro-1H-benzimidazol-2-yl)-3-methoxymethyl-4-(5-methyl-pyridin-2-yl)-3,4-dihydro-2H-benzo[1,4]oxazine,
103) (S)-8-(5-chloro-6-fluoro-1H-benzimidazol-2-yl)-3-methoxymethyl-4-(5-methyl-pyridin-2-yl)-3,4-dihydro-2H-benzo[1,4]oxazine,
104) (S)-8-(6-bromo-4-methyl-1H-benzimidazol-2-yl)-3-methoxymethyl-4-(5-methyl-pyridin-2-yl)-3,4-dihydro-2H-benzo[1,4]oxazine,
105) (S)-8-(4-bromo-6-trifluoromethoxy-1H-benzimidazol-2-yl)-3-methoxymethyl-4-(5-methyl-pyridin-2-yl)-3,4-dihydro-2H-benzo[1,4]oxazine,
106) (S)-8-(6-methoxy-1H-benzo[d]imidazol-2-yl)-3-(methoxymethyl)-4-(5-methyl-pyridin-2-yl)-3,4-dihydro-2H-benzo[b][1,4]oxazine,
107) (S)-8-(4,6-difluoro-1H-benzo[d]imidazol-2-yl)-3-(methoxymethyl)-4-(5-methyl-pyridin-2-yl)-3,4-dihydro-2H-benzo[b][1,4]oxazine,
108) (S)-3-(methoxymethyl)-8-(4-methyl-1H-benzo[d]imidazol-2-yl)-4-(5-methyl-pyridin-2-yl)-3,4-dihydro-2H-benzo[b][1,4]oxazine,
109) (S)-3-(methoxymethyl)-8-(5-methyl-1H-benzo[d]imidazol-2-yl)-4-(5-methyl-pyridin-2-yl)-3,4-dihydro-2H-benzo[b][1,4]oxazine, and
110) (S)-8-(1H-benzo[d]imidazol-2-yl)-3-(methoxymethyl)-4-(5-methyl-pyridin-2-yl)-3,4-dihydro-2H-benzo[b][1,4]oxazine.

5. The compound according to claim 4, or the pharmaceutically acceptable salt, or isomer thereof, which is selected from the group consisting of:
[(S)-8-(6-bromo-1H-benzimidazol-2-yl)-4-(5-methyl-pyridin-2-yl)-3,4-dihydro-2H-benzo[1,4]oxazin-3-yl]-methanol;
[(S)-8-(4-bromo-6-trifluoromethyl-1H-benzimidazol-2-yl)-4-(5-methyl-pyridin-2-yl)-3,4-dihydro-2H-benzo[1,4]oxazin-3-yl]-methanol;
[(S)-8-(6-bromo-4-fluoro-1H-benzimidazol-2-yl)-4-(5-methyl-pyridin-2-yl)-3,4-dihydro-2H-benzo[1,4]oxazin-3-yl]-methanol;
(S)-8-(4-bromo-6-trifluoromethyl-1H-benzimidazol-2-yl)-3-methoxymethyl-4-(5-methyl-pyridin-2-yl)-3,4-dihydro-2H-benzo[1,4]oxazine;
[(S)-8-(5,6-difluoro-1H-benzimidazol-2-yl)-4-(5-methyl-pyridin-2-yl)-3,4-dihydro-2H-benzo[1,4]oxazin-3-yl]-methanol; and
[(S)-8-(6-chloro-5-fluoro-1H-benzimidazol-2-yl)-4-(5-methyl-pyridin-2-yl)-3,4-dihydro-2H-benzo[1,4]oxazin-3-yl]-methanol.

6. A pharmaceutical composition comprising the compound of formula (1) of claim 1, or the pharmaceutically acceptable salt, or isomer thereof as an active ingredient and a pharmaceutically acceptable carrier.

7. A method for treating a disease associated with antagonistic activity of vanilloid receptor in a mammal, which comprises administering the compound of formula (1) of claim 1, or the pharmaceutically acceptable salt, or isomer thereof to the mammal, wherein the disease is selected from the group consisting of acute pain, chronic pain, neuropathic pain, post-operative pain, migraines, arthralgia, neuropathy, neuronal damages, diabetic neuropathy, neurodermatitis, bladder hypersensitivity, obesity, irritable bowel syndrome, asthma, chronic obstructive pulmonary disease, glaucoma, psoriasis, irritation of the skin, eyes, or mucous membranes, reflux esophagitis, gastricduodenal ulcers, and combinations thereof.

* * * * *

UNITED STATES PATENT AND TRADEMARK OFFICE
CERTIFICATE OF CORRECTION

PATENT NO. : 8,362,012 B2
APPLICATION NO. : 12/934638
DATED : January 29, 2013
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

Page 1 of 2

PATENT NO. : 8,362,012 B2
APPLICATION NO. : 12/934638
DATED : January 29, 2013
INVENTOR(S) : Ji Duck Kim et al.

It is certified that error appears in the above-identified patent and that said Letters Patent is hereby corrected as shown below:

In the Claims

Column 63, Line 29, Claim 1:
"$NR^dR^d$; $OR^d$; $OC(=O)R^e$; $OC(=O)$ $OR^e$; $OC(=O)$" should read, --$NR^dR^d$; $OR^d$; $OC(=O)R^e$; $OC(=O)OR^e$; $OC(=O)$--.

Column 64, Line 29, Claim 1:
"one or more $R^f$ substituents; phenyl; naphtyl; benzyl;" should read, --one or more $R^f$ substituents; phenyl; naphtyl; benzyl;--.

Column 66, Lines 19-20, Claim 4:
"12) 8-(5-tert-butyl-1H-benzimidazol-2-yl)-4-pyridin-2-yl)-3,4-dihydro-2H-benzo[1,4]oxazine," should read, --12) 8-(5-tert-butyl-1H-benzimidazol-2-yl)-4-pyridin-2-yl-3,4-dihydro-2H-benzo[1,4]oxazine,--.

Column 67, Lines 12-14, Claim 4:
"36) [(S)-8-(6 bromo-1H-benzimidazol-2-yl)-4-(5-methyl-pyridin-2-yl)-3,4-dihydro-2H-benzo[1,4]oxazin-3-yl]-methanol," should read, --36) [(S)-8-(6-bromo-1H-benzimidazol-2-yl)-4-(5-methyl-pyridin-2-yl)-3,4-dihydro-2H-benzo[1,4]oxazin-3-yl]-methanol,--.

Column 67, Lines 39-41, Claim 4:
"45) [(S)-8-(6-chloro-5-fluoro-1H-benzimidazol-2-yl)-4-(5-methyl-pyridin-2-yl)-3,4-dihydro-2H-benzo[1,4]oxazin-3yl]-methanol," should read, --45) [(S)-8-(6-chloro-5-fluoro-1H-benzimidazol-2-yl)-4-(5-methyl-pyridin-2-yl)-3,4-dihydro-2H-benzo[1,4]oxazin-3-yl]-methanol,--.

Column 67, Lines 54-56, Claim 4:
"50) [(S)-8-(4-methyl-1H-benzimidazol-2-yl)-4-(5-methyl-pyridine-2-yl)-3,4-dihydro-2H-benzo[1,4]oxazin-3-3-yl]-methanol," should read, --50) [(S)-8-(4-methyl-1H-benzimidazol-2-yl)-4-(5-methyl-pyridine-2-yl)-3,4-dihydro-2H-benzo[1,4]oxazin-3-yl]-methanol,--.

Signed and Sealed this
Eighth Day of April, 2014

Michelle K. Lee
*Deputy Director of the United States Patent and Trademark Office*

Column 69, Lines 46-48, Claim 4:

"91) (S)-3-methoxymethyl-4-(5-methyl-pyridin-2-yl)-8-(6-trifluoromethylchloro-1H-benzimidazol-2-yl)-3,4-dihydro-2H-benzo[1,4]oxazine," should read, --91) (S)-3-methoxymethyl-4-(5-methyl-pyridin-2-yl)-8-(6-chloro-1H-benzimidazol-2-yl)-3,4-dihydro-2H-benzo[1,4]oxazine,--.